(12) United States Patent
Choi et al.

(10) Patent No.: US 10,160,724 B2
(45) Date of Patent: Dec. 25, 2018

(54) TETRAHYDROPYRIDINE DERIVATIVES AND THEIR USE AS ANTIBACTERIAL AGENTS

(71) Applicant: Dong-A St Co., Ltd., Seoul (KR)

(72) Inventors: Sun-Ho Choi, Seoul (KR); Weon-Bin Im, Gyeonggi-do (KR); Sung-Hak Choi, Gyeonggi-do (KR); Chong-Hwan Cho, Gyeonggi-do (KR); Ho-Sang Moon, Gyeonggi-do (KR); Jung-Sang Park, Gyeonggi-do (KR); Min-Jung Lee, Gyeonggi-do (KR); Hyun-Jung Sung, Gyeonggi-do (KR); Jun-Hwan Moon, Gyeonggi-do (KR); Seung-Hyun Song, Gyeonggi-do (KR); Hyung-Keun Lee, Seoul (KR); Ji-Hoon Choi, Gyeonggi-do (KR); Cheon-Hyoung Park, Seoul (KR); Yoon-Jung Kim, Gyeonggi-do (KR); Jin-Hyuk Kim, Gyeonggi-do (KR)

(73) Assignee: Dong-A St Co., Ltd., Seoul (KR)

( * ) Notice: Subject to any disclaimer, the term of this patent is extended or adjusted under 35 U.S.C. 154(b) by 0 days.

(21) Appl. No.: 15/718,474

(22) Filed: Sep. 28, 2017

(65) Prior Publication Data

US 2018/0086709 A1 Mar. 29, 2018

Related U.S. Application Data

(60) Provisional application No. 62/400,694, filed on Sep. 28, 2016.

(51) Int. Cl.
| | | |
|---|---|---|
| *C07D 211/70* | (2006.01) | |
| *C07D 401/04* | (2006.01) | |
| *C07D 401/10* | (2006.01) | |
| *C07D 405/10* | (2006.01) | |
| *C07D 409/10* | (2006.01) | |

(52) U.S. Cl.
CPC .......... *C07D 211/70* (2013.01); *C07D 401/04* (2013.01); *C07D 401/10* (2013.01); *C07D 405/10* (2013.01); *C07D 409/10* (2013.01)

(58) Field of Classification Search
CPC .. C07D 211/70; C07D 401/04; C07D 401/10; C07D 405/10; C07D 409/10
See application file for complete search history.

(56) References Cited

U.S. PATENT DOCUMENTS

2004/0229864 A1  11/2004  Bourrain et al.

FOREIGN PATENT DOCUMENTS

| WO | WO 2009-008905 | 1/2009 |
| WO | WO 2011-045703 | 4/2011 |
| WO | WO 2013-170165 | 11/2013 |
| WO | WO 2015-173329 | 11/2015 |

OTHER PUBLICATIONS

Raetz, et al., Lipid A Modification Systems in Gram-Negative Bacteria, Annu. Rev. Biochem. 76: 295-329 (2007). (Year: 2007).*
Raetz et al., *Lipid A Modification Systems in Gram-Negative Bacteria*, Annu. Rev. Biochem., 76:295-329 (2007).
Gao et al., *Overexpression of Pseudomonas aeruginosa LpxC with its inhibitors in an acrB-deficient Escherichia coli strain*, Protein Expression and Purification, 104:57-64 (2014).
International Search Report and Written Opinion for Intl App No. PCT/KR2017/010896 dated Jan. 11, 2018 (9 pages).

* cited by examiner

*Primary Examiner* — Erich A Leeser
(74) *Attorney, Agent, or Firm* — Fish & Richardson P.C.

(57) ABSTRACT

The present disclosure relates to a novel tetrahydropyridine derivative compound, a stereoisomer thereof, or a pharmaceutically acceptable salt thereof, methods for preparing the compounds, methods for inhibiting UDP-3-O—(R-3-hydroxymyristoyl)-N-acetylglucosamine deacetylase (LpxC), methods for treating Gram-negative bacterial infections, the use of the compounds for the preparation of therapeutic medicaments for treating Gram-negative bacterial infections, and pharmaceutical compositions for prevention or treatment of Gram-negative bacterial infections, which contain the compounds. The compounds represented by formula I, stereoisomers thereof or pharmaceutically acceptable salts thereof according to the present disclosure can exhibit excellent effects on the treatment bacterial infections.

8 Claims, No Drawings

TETRAHYDROPYRIDINE DERIVATIVES AND THEIR USE AS ANTIBACTERIAL AGENTS

This application claims the benefit of priority under U.S.C. § 119(e) to U.S. Provisional patent application Ser. No. 62/400,694 filed Sep. 28, 2016, which is incorporated herein by reference.

TECHNICAL FIELD

The present disclosure relates to novel tetrahydropyridine derivatives that are useful for the treatment of bacterial infection, especially Gram-negative infections. The present disclosure also relates to methods of using such compounds in the treatment of bacterial infections in mammals, to use thereof for the preparation of medicaments for treating bacterial infections, and to pharmaceutical compositions containing such compounds.

BACKGROUND ART

Infection by Gram-negative bacteria such as Extended Spectrum β-lactamase producing (ESBL) Enterobacteriaceae, *Pseudomonas aeruginosa*, and *Acinetobacter baumannii* is a major health problem, especially in the case of hospital-acquired infections. In addition, there is an increasing level of resistance to current antibiotic therapies, which severely limits treatment options.

Gram-negative bacteria are unique in that their outer membrane contains lipopolysaccharide (LPS), which is crucial for maintaining membrane integrity, and is essential for bacterial viability (Rev. Biochem 76: 295-329, 2007). The major lipid component of LPS is Lipid A and inhibition of Lipid A biosynthesis is lethal to bacteria. Lipid A synthesized on the cytoplasmic surface of the bacterial inner membrane via a pathway that consists of nine different enzymes. These enzymes are highly conserved in most Gram-negative bacteria. LpxC is the enzyme that catalyzes the first committed step in the Lipid A biosynthetic pathway, the removal of the N-acetyl group of UDP-3-O—(R-3-hydroxymyristoyl)-N-acetylglucosamine. LpxC is a $Zn^{2+}$ dependent enzyme that has no mammalian homologue, making it a good target for the development of novel antibiotics.

DISCLOSURE

Technical Problem

It is an object of the present disclosure to provide tetrahydropyridine derivatives capable of inhibiting UDP-3-O—(R-3-hydroxymyristoyl)-N-acetylglucosamine deacetylase (LpxC) and treating Gram-negative bacterial infections, stereoisomers thereof, or pharmaceutically acceptable salts thereof.

Another object of the present disclosure is to provide methods for preparing the compounds.

Still another object of the present disclosure is to provide methods for inhibiting UDP-3-O—(R-3-hydroxymyristoyl)-N-acetylglucosamine deacetylase (LpxC), which comprise administering a therapeutically effective amount of the compounds.

Still another object of the present disclosure is to provide methods for treating Gram-negative bacterial infections, which comprise administering a therapeutically effective amount of the compounds.

Still another object of the present disclosure is to provide the use of the compounds for the preparation of therapeutic medicaments for treating Gram-negative bacterial infections.

Still another object of the present disclosure is to provide pharmaceutical compositions for prevention or treatment of Gram-negative bacterial infections, which contain the compounds.

Technical Solution

The present inventors have discovered novel tetrahydropyridine derivatives, which have UDP-3-O—(R-3-hydroxymyristoyl)-N-acetylglucosamine deacetylase (LpxC) inhibitory activity, and have found that these compounds can be used for treating Gram-negative bacterial infections, thereby completing the present invention.

Tetrahydropyridine Derivative Compounds

To achieve the above objects, the present disclosure provides a tetrahydropyridine derivative compound represented by the following formula I, a stereoisomer thereof, or a pharmaceutically acceptable salt thereof:

[Formula I]

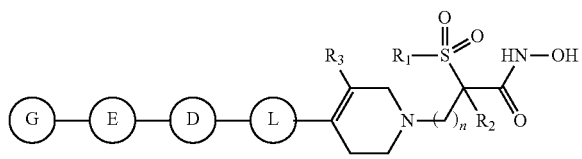

n is 1, 2 or 3;

$R_1$ is C1-C6 alkyl or C1-C6 haloalkyl;

$R_2$ is hydrogen or C1-C6 alkyl;

$R_3$ is hydrogen, C1-C6 alkyl, C1-C6 alkoxy, —OH or halogen;

L is C3-C7 cycloalkyl, aryl, heteroaryl or null, wherein at least one H of C3-C7 cycloalkyl, aryl or heteroaryl may be substituted with halogen, C1-C6 alkyl, C1-C6 haloalkyl, —$NR_AR_B$ or —OH;

D is C≡C, C3-C7 cycloalkyl, aryl, heteroaryl or null, wherein at least one H of C3-C7 cycloalkyl, aryl or heteroaryl may be substituted with halogen, C1-C6 alkyl, C1-C6 haloalkyl, —$NR_AR_B$ or —OH;

E is C≡C, C3-C7 cycloalkyl, aryl, heteroaryl or null, wherein at least one H of C3-C7 cycloalkyl, aryl or heteroaryl may be substituted with halogen, C1-C6 alkyl, C1-C6 haloalkyl, —$NR_AR_B$ or —OH;

G is C1-C6 alkyl, C3-C7 cycloalkyl, 4-6 membered heterocycloalkyl, aryl or heteroaryl, wherein at least one H of C1-C6 alkyl may be substituted with halogen, —$NR_AR_B$, —OH or —$OR_C$, at least one H of C3-C7 cycloalkyl or 4-6 membered heterocycloalkyl may be substituted with C1-C6 alkyl, C1-C6 alkyl-$NR_AR_B$, C1-C6 hydroxyalkyl, C1-C6 haloalkyl, C1-C6 alkoxy, C1-C6 alkyl-$OR_C$, —$NR_AR_B$, —OH, —(C=O)—C1-C6 alkyl or —S(=O)$_2$—C1-C6 alkyl, at least one H of aryl or heteroaryl may be substituted with C1-C6 alkyl, C1-C6 hydroxyalkyl, C1-C6 alkyl-$NR_AR_B$, halogen, nitro, cyano, —$NR_AR_B$, —OH, —$OR_C$, —S(=O)$_2$—C1-C6 alkyl, —S(=O)$_2$—$NR_AR_B$ or —N—S(=O)$_2$—C1-C6 alkyl;

$R_A$ and $R_B$ are each independently hydrogen or C1-C6 alkyl, or $R_A$ and $R_B$ may be linked together to form 4-6 membered ring, wherein the 4-6 membered ring may have O or S atom and at least one H of the 4-6 membered ring may be substituted with halogen, —OH or C1-C6 hydroxyalkyl;

$R_C$ is C1-C6 alkyl, C1-C6 hydroxyalkyl, —(C=O)—$NR_DR_E$ or —S(=O)$_2$—C1-C6 alkyl; and $R_D$ and $R_E$ are each independently hydrogen or C1-C6 alkyl.

In one aspect, n is 1 or 2;

$R_1$ is C1-C6 alkyl;

$R_2$ is C1-C6 alkyl;

$R_3$ is hydrogen;

L is aryl, heteroaryl or null, wherein at least one H of aryl or heteroaryl may be substituted with halogen, C1-C6 alkyl or C1-C6 haloalkyl;

D is C≡C or null;

E is C≡C or null;

G is C1-C6 alkyl, C3-C7 cycloalkyl, 4-6 membered heterocycloalkyl, aryl or heteroaryl, wherein at least one H of C1-C6 alkyl may be substituted with halogen, —$NR_AR_B$, —OH or —$OR_C$, at least one H of 4-6 membered heterocycloalkyl may be substituted with C1-C6 alkyl, —(C=O)—C1-C6 alkyl or —S(=O)$_2$—C1-C6 alkyl, at least one H of aryl or heteroaryl may be substituted with C1-C6 alkyl, C1-C6 hydroxyalkyl, C1-C6 alkyl-$NR_AR_B$, halogen, nitro, cyano, —$NR_AR_B$, —OH, —$OR_C$, —S(=O)$_2$—C1-C6 alkyl or —S(=O)$_2$—$NR_AR_B$;

$R_A$ and $R_B$ are each independently hydrogen or C1-C6 alkyl, or $R_A$ and $R_B$ may be linked together to form 4-6 membered ring, wherein the 4-6 membered ring may have O atom and at least one H of the 4-6 membered ring may be substituted with C1-C6 hydroxyalkyl;

$R_C$ is C1-C6 alkyl, C1-C6 hydroxyalkyl, —(C=O)—$NR_DR_E$ or —S(=O)$_2$—C1-C6 alkyl; and $R_D$ and $R_E$ are each independently hydrogen.

In another aspect, n is 1 or 2;

$R_1$ is C1-C6 alkyl;

$R_2$ is C1-C6 alkyl;

$R_3$ is hydrogen;

L is phenyl, pyridinyl or null, wherein at least one H of phenyl or pyridinyl may be substituted with halogen, C1-C6 alkyl or C1-C6 haloalkyl;

D is C≡C or null;

E is C≡C or null;

G is C1-C6 alkyl, C3-C6 cycloalkyl, 4-6 membered heterocycloalkyl, phenyl, pyridinyl, furanyl, thiophenyl or imidazolyl, wherein at least one H of C1-C6 alkyl may be substituted with halogen, —$NR_AR_B$, —OH or —$OR_C$, at least one H of 4-6 membered heterocycloalkyl may be substituted with C1-C6 alkyl, —(C=O)—C1-C6 alkyl or —S(=O)$_2$—C1-C6 alkyl, at least one H of phenyl, pyridinyl, furanyl, thiophenyl or imidazolyl may be substituted with C1-C6 alkyl, C1-C6 hydroxyalkyl, C1-C6 alkyl-$NR_AR_B$, halogen, nitro, cyano, —$NR_AR_B$, —OH, —$OR_C$, —S(=O)$_2$—C1-C6 alkyl or —S(=O)$_2$—$NR_AR_B$;

$R_A$ and $R_B$ are each independently hydrogen or C1-C6 alkyl, or $R_A$ and $R_B$ may be linked together to form 4-6 membered ring, wherein the 4-6 membered ring may have O atom and at least one H of the 4-6 membered ring may be substituted with C1-C6 hydroxyalkyl;

$R_C$ is C1-C6 alkyl, C1-C6 hydroxyalkyl, —(C=O)—$NR_DR_E$ or —S(=O)$_2$—C1-C6 alkyl; and $R_D$ and $R_E$ are each independently hydrogen.

As used herein, including the claims, the following terms have the meaning defined below, unless specifically indicated otherwise.

The term "alkyl" refers to a branched or straight chained hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl or n-decyl.

The term "alkoxy" refer to hydrogen atom of a hydroxyl group is substituted with alkyl. Representative examples of alkoxy include, but are not limited to, methoxy, ethoxy, propoxy, isopropoxy, butoxy, isobutoxy, tert-butoxy, pentyloxy, neopentyloxy or isopentyloxy.

The term "alkynyl" refers to straight chain hydrocarbon group containing from 2 to 10 carbon atoms and containing at least one carbon-carbon triple bond. Representative examples of alkynyl include, but are not limited to, acetylene, propynyl, butynyl, pentynyl, hexynyl or heptynyl.

The term "aryl" refer to mono-, bi- or other multicarbocyclic aromatic ring system. Representative examples of aryl include, but are not limited to, phenyl, biphenyl, naphthyl, as well as benzo-fused carbocyclic moieties.

The term "heteroaryl" refer to mono-, bi or other multicarbocyclic aromatic ring system containing one or more heteroatoms selected from O, N, or S. Representative examples of heteroaryl include, but are not limited to, pyrrolyl, imidazolyl, pyrazolyl, triazolyl, tetrazolyl, furyl, furanyl, thiophenyl, pyridinyl, pyrimidinyl, oxazolyl, oxadiazolyl, isoxazolyl, indolyl, quinolyl, isoquinolyl, benzimidazolyl, benzothienyl or benzofuryl.

The term "cycloalkyl" refer to a saturated cyclic hydrocarbon ring of 3 to 8 carbon atoms. Representative examples of cycloalkyl include, but are not limited to, cyclopropyl, cyclobutyl, cyclopentyl or cyclohexyl.

The term "heterocyclic" refer to a cyclic group containing one or more heteroatoms selected from O, N, or S. Representative examples of heterocyclic include, but are not limited to, azetidinyl, tetrahydrofuranyl, imidazolidinyl, pyrrolidinyl, piperidinyl, piperazinyl, oxazolidinyl, thiazolidinyl, pyrazolidinyl, morpholinyl, thio-morpholinyl, oxazinyl or tetrahydropyridinyl.

The term "pharmaceutically acceptable" means the substance or composition must be compatible chemically and/or toxicologically, with the other ingredients comprising a formulation, and/or the mammal being treated therewith.

The term "stereoisomer" means compounds that possess one or more chiral centers and each center may exist in the R or S configuration. Stereoisomers include all diastereomeric, enantiomeric and epimeric forms as well as racemates and mixtures thereof.

In some aspect, the novel tetrahydropyridine derivatives selective from the group consisting of the following compounds:

1) 4-(4-(4-((4-(dimethylamino)phenyl)ethynyl)phenyl)-3,6-dihydropyridin-1(2H)-yl)-N-hydroxy-2-methyl-2-(methylsulfonyl)butanamide;

2) N-hydroxy-2-methyl-2-(methylsulfonyl)-4-(4-(4-(phenylethynyl)phenyl)-3,6-dihydropyridin-1(2H)-yl)butanamide;

3) N-hydroxy-4-(4-(4-((4-methoxyphenyl)ethynyl)phenyl)-3,6-dihydropyridin-1(2H)-yl)-2-methyl-2-(methylsulfonyl)butanamide;

4) 4-(4-(4-(cyclopropylethynyl)phenyl)-3,6-dihydropyridin-1(2H)-yl)-N-hydroxy-2-methyl-2-(methylsulfonyl)butanamide;
5) N-hydroxy-4-(4-(4-(4-hydroxybut-1-yn-1-yl)phenyl)-3,6-dihydropyridin-1(2H)-yl)-2-methyl-2-(methylsulfonyl)butanamide;
6) 4-(4-(4-(hex-1-yn-1-yl)phenyl)-3,6-dihydropyridin-1(2H)-yl)-N-hydroxy-2-methyl-2-(methylsulfonyl)butanamide;
7) 4-(4-(4-(3-(dimethylamino)prop-1-yn-1-yl)phenyl)-3,6-dihydropyridin-1(2H)-yl)-N-hydroxy-2-methyl-2-(methylsulfonyl)butanamide;
8) N-hydroxy-4-(4-(4-(3-hydroxybut-1-yn-1-yl)phenyl)-3,6-dihydropyridin-1(2H)-yl)-2-methyl-2-(methylsulfonyl)butanamide;
9) 4-(4-(4-(cyclopentylethynyl)phenyl)-3,6-dihydropyridin-1(2H)-yl)-N-hydroxy-2-methyl-2-(methylsulfonyl)butanamide;
10) 4-(4-(4-(cyclohexylethynyl)phenyl)-3,6-dihydropyridin-1(2H)-yl)-N-hydroxy-2-methyl-2-(methylsulfonyl)butanamide;
11) N-hydroxy-2-methyl-2-(methylsulfonyl)-4-(4-(4-(pent-1-yn-1-yl)phenyl)-3,6-dihydropyridin-1(2H)-yl)butanamide;
12) 4-(4-(4-(3-cyclohexylprop-1-yn-1-yl)phenyl)-3,6-dihydropyridin-1(2H)-yl)-N-hydroxy-2-methyl-2-(methylsulfonyl)butanamide;
13) N-hydroxy-2-methyl-4-(4-(4-(4-methylpent-1-yn-1-yl)phenyl)-3,6-dihydropyridin-1(2H)-yl)-2-(methylsulfonyl)butanamide;
14) 4-(4-(4-(5-chloropent-1-yn-1-yl)phenyl)-3,6-dihydropyridin-1(2H)-yl)-N-hydroxy-2-methyl-2-(methylsulfonyl)butanamide;
15) N-hydroxy-2-methyl-2-(methylsulfonyl)-4-(4-(4-(3-(pyrrolidin-1-yl)prop-1-yn-1-yl)phenyl)-3,6-dihydropyridin-1(2H)-yl)butanamide;
16) 4-(4-(4-(3-(diethylamino)prop-1-yn-1-yl)phenyl)-3,6-dihydropyridin-1(2H)-yl)-N-hydroxy-2-methyl-2-(methylsulfonyl)butanamide;
17) N-hydroxy-4-(4-(4-(3-((S)-2-(hydroxymethyl)pyrrolidin-1-yl)prop-1-yn-1-yl)phenyl)-3,6-dihydropyridin-1(2H)-yl)-2-methyl-2-(methylsulfonyl)butanamide;
18) N-hydroxy-4-(4-(4-(5-hydroxypent-1-yn-1-yl)phenyl)-3,6-dihydropyridin-1(2H)-yl)-2-methyl-2-(methylsulfonyl)butanamide;
19) 5-(4-(1-(4-(hydroxyamino)-3-methyl-3-(methylsulfonyl)-4-oxobutyl)-1,2,3,6-tetrahydropyridin-4-yl)phenyl)pent-4-yn-1-yl methanesulfonate;
20) 4-(4-(4-(5-(dimethylamino)pent-1-yn-1-yl)phenyl)-3,6-dihydropyridin-1(2H)-yl)-N-hydroxy-2-methyl-2-(methylsulfonyl)butanamide;
21) 4-(4-(4-(5-aminopent-1-yn-1-yl)phenyl)-3,6-dihydropyridin-1(2H)-yl)-N-hydroxy-2-methyl-2-(methylsulfonyl)butanamide;
22) N-hydroxy-4-(4-(4-(3-hydroxyprop-1-yn-1-yl)phenyl)-3,6-dihydropyridin-1(2H)-yl)-2-methyl-2-(methylsulfonyl)butanamide;
23) N-hydroxy-4-(4-(4-(3-methoxyprop-1-yn-1-yl)phenyl)-3,6-dihydropyridin-1(2H)-yl)-2-methyl-2-(methylsulfonyl)butanamide;
24) N-hydroxy-4-(4-(4-(3-(3-hydroxypropoxy)prop-1-yn-1-yl)phenyl)-3,6-dihydropyridin-1(2H)-yl)-2-methyl-2-(methylsulfonyl)butanamide;
25) N-hydroxy-2-methyl-2-(methylsulfonyl)-4-(4-(4-(3-morpholinoprop-1-yn-1-yl)phenyl)-3,6-dihydropyridin-1(2H)-yl)butanamide;
26) 3-(4-(1-(4-(hydroxyamino)-3-methyl-3-(methylsulfonyl)-4-oxobutyl)-1,2,3,6-tetrahydropyridin-4-yl)phenyl)prop-2-yn-1-yl carbamate;
27) 5-(4-(1-(4-(hydroxyamino)-3-methyl-3-(methylsulfonyl)-4-oxobutyl)-1,2,3,6-tetrahydropyridin-4-yl)phenyl)pent-4-yn-1-yl carbamate;
28) N-hydroxy-4-(4-(4-(5-methoxypent-1-yn-1-yl)phenyl)-3,6-dihydropyridin-1(2H)-yl)-2-methyl-2-(methylsulfonyl)butanamide;
29) N-hydroxy-4-(4-(4-(6-hydroxyhex-1-yn-1-yl)phenyl)-3,6-dihydropyridin-1(2H)-yl)-2-methyl-2-(methylsulfonyl)butanamide;
30) N-hydroxy-2-methyl-2-(methylsulfonyl)-4-(4-(4-(6-morpholinohex-1-yn-1-yl)phenyl)-3,6-dihydropyridin-1(2H)-yl)butanamide;
31) 4-(4-(4-(3-(dimethylamino)prop-1-yn-1-yl)-3-fluorophenyl)-3,6-dihydropyridin-1(2H)-yl)-N-hydroxy-2-methyl-2-(methylsulfonyl)butanamide;
32) 4-(4-(4-(3-(dimethylamino)prop-1-yn-1-yl)-3,5-difluorophenyl)-3,6-dihydropyridin-1(2H)-yl)-N-hydroxy-2-methyl-2-(methylsulfonyl)butanamide;
33) 4-(4-(4-(3-(dimethylamino)prop-1-yn-1-yl)-2-fluorophenyl)-3,6-dihydropyridin-1(2H)-yl)-N-hydroxy-2-methyl-2-(methylsulfonyl)butanamide;
34) N-hydroxy-2-methyl-2-(methylsulfonyl)-4-(4-(4-(thiophen-2-ylethynyl)phenyl)-3,6-dihydropyridin-1(2H)-yl)butanamide;
35) N-hydroxy-2-methyl-2-(methylsulfonyl)-4-(4-(4-((4-nitrophenyl)ethynyl)phenyl)-3,6-dihydropyridin-1(2H)-yl)butanamide;
36) N-hydroxy-2-methyl-2-(methylsulfonyl)-4-(4-(4-(pyridin-3-ylethynyl)phenyl)-3,6-dihydropyridin-1(2H)-yl)butanamide;
37) N-hydroxy-4-(4-(4-((4-hydroxyphenyl)ethynyl)phenyl)-3,6-dihydropyridin-1(2H)-yl)-2-methyl-2-(methylsulfonyl)butanamide;
38) N-hydroxy-2-methyl-4-(4-(4-((1-methyl-1H-imidazol-4-yl)ethynyl)phenyl)-3,6-dihydropyridin-1(2H)-yl)-2-(methylsulfonyl)butanamide;
39) N-hydroxy-2-methyl-4-(4-(4-((1-methylazetidin-3-yl)ethynyl)phenyl)-3,6-dihydropyridin-1(2H)-yl)-2-(methylsulfonyl)butanamide;
40) 4-(4-(4-((1-acetylazetidin-3-yl)ethynyl)phenyl)-3,6-dihydropyridin-1(2H)-yl)-N-hydroxy-2-methyl-2-(methylsulfonyl)butanamide;
41) N-hydroxy-2-methyl-2-(methylsulfonyl)-4-(4-(4-((1-(methylsulfonyl)azetidin-3-yl)ethynyl)phenyl)-3,6-dihydropyridin-1(2H)-yl)butanamide;
42) 4-(4-(3-fluoro-4-(7-hydroxyhepta-1,3-diyn-1-yl)phenyl)-3,6-dihydropyridin-1(2H)-yl)-N-hydroxy-2-methyl-2-(methylsulfonyl)butanamide;
43) 4-(4-(3-fluoro-4-(6-hydroxyhexa-1,3-diyn-1-yl)phenyl)-3,6-dihydropyridin-1(2H)-yl)-N-hydroxy-2-methyl-2-(methylsulfonyl)butanamide;
44) 4-(4-(4-(cyclopropylbuta-1,3-diyn-1-yl)-3-fluorophenyl)-3,6-dihydropyridin-1(2H)-yl)-N-hydroxy-2-methyl-2-(methylsulfonyl)butanamide;
45) 4-(4-(4-(5-(dimethylamino)penta-1,3-diyn-1-yl)-3-fluorophenyl)-3,6-dihydropyridin-1(2H)-yl)-N-hydroxy-2-methyl-2-(methylsulfonyl)butanamide;
46) N-hydroxy-4-(4-(4-(7-hydroxyhepta-1,3-diyn-1-yl)phenyl)-3,6-dihydropyridin-1(2H)-yl)-2-methyl-2-(methylsulfonyl)butanamide;
47) N-hydroxy-4-(4-(4-(6-hydroxyhexa-1,3-diyn-1-yl)phenyl)-3,6-dihydropyridin-1(2H)-yl)-2-methyl-2-(methylsulfonyl)butanamide;

48) N-hydroxy-4-(4-(4-(5-hydroxypenta-1,3-diyn-1-yl)phenyl)-3,6-dihydropyridin-1(2H)-yl)-2-methyl-2-(methylsulfonyl)butanamide;
49) 4-(4-(4-(5-(dimethylamino)penta-1,3-diyn-1-yl)phenyl)-3,6-dihydropyridin-1(2H)-yl)-N-hydroxy-2-methyl-2-(methylsulfonyl)butanamide;
50) N-hydroxy-4-(4-(4-(5-methoxypenta-1,3-diyn-1-yl)phenyl)-3,6-dihydropyridin-1(2H)-yl)-2-methyl-2-(methylsulfonyl)butanamide;
51) N-hydroxy-2-methyl-2-(methylsulfonyl)-4-(4-(4-(phenylbuta-1,3-diyn-1-yl)phenyl)-3,6-dihydropyridin-1(2H)-yl)butanamide;
52) N-hydroxy-2-methyl-2-(methylsulfonyl)-4-(4-(pyridin-4-ylethynyl)-3,6-dihydropyridin-1(2H)-yl)butanamide;
53) 4-(4-((4-bromophenyl)ethynyl)-3,6-dihydropyridin-1(2H)-yl)-N-hydroxy-2-methyl-2-(methylsulfonyl)butanamide;
54) N-hydroxy-4-(4-(7-hydroxyhepta-1,3-diyn-1-yl)-3,6-dihydropyridin-1(2H)-yl)-2-methyl-2-(methylsulfonyl)butanamide;
55) N-hydroxy-2-methyl-2-(methylsulfonyl)-4-(4-(4-(pyridin-4-yl)phenyl)-3,6-dihydropyridin-1(2H)-yl)butanamide;
56) 4-(4-([1,1'-biphenyl]-4-yl)-3,6-dihydropyridin-1(2H)-yl)-N-hydroxy-2-methyl-2-(methylsulfonyl)butanamide;
57) 4-(4-(4'-chloro-[1,1'-biphenyl]-4-yl)-3,6-dihydropyridin-1(2H)-yl)-N-hydroxy-2-methyl-2-(methylsulfonyl)butanamide;
58) 4-(4-(4'-fluoro-[1,1'-biphenyl]-4-yl)-3,6-dihydropyridin-1(2H)-yl)-N-hydroxy-2-methyl-2-(methylsulfonyl)butanamide;
59) N-hydroxy-4-(4-(4'-hydroxy-[1,1'-biphenyl]-4-yl)-3,6-dihydropyridin-1(2H)-yl)-2-methyl-2-(methylsulfonyl)butanamide;
60) 4-(4-(3'-fluoro-4'-methoxy-[1,1'-biphenyl]-4-yl)-3,6-dihydropyridin-1(2H)-yl)-N-hydroxy-2-methyl-2-(methylsulfonyl)butanamide;
61) N-hydroxy-2-methyl-2-(methylsulfonyl)-4-(4-(4-(pyridin-3-yl)phenyl)-3,6-dihydropyridin-1(2H)-yl)butanamide;
62) 4-(4-(4-(6-fluoropyridin-3-yl)phenyl)-3,6-dihydropyridin-1(2H)-yl)-N-hydroxy-2-methyl-2-(methylsulfonyl)butanamide;
63) 4-(4-(4-(furan-3-yl)phenyl)-3,6-dihydropyridin-1(2H)-yl)-N-hydroxy-2-methyl-2-(methylsulfonyl)butanamide;
64) N-hydroxy-2-methyl-2-(methylsulfonyl)-4-(4-(4'-(methylsulfonyl)-[1,1'-biphenyl]-4-yl)-3,6-dihydropyridin-1(2H)-yl)butanamide;
65) N-hydroxy-4-(4-(4'-(hydroxymethyl)-[1,1'-biphenyl]-4-yl)-3,6-dihydropyridin-1(2H)-yl)-2-methyl-2-(methylsulfonyl) butanamide;
66) 4-(4-(4'-cyano-[1,1'-biphenyl]-4-yl)-3,6-dihydropyridin-1(2H)-yl)-N-hydroxy-2-methyl-2-(methylsulfonyl)butanamide;
67) N-hydroxy-2-methyl-2-(methylsulfonyl)-4-(4-(4'-pentyl-[1,1'-biphenyl]-4-yl)-3,6-dihydropyridin-1(2H)-yl)butanamide;
68) 4-(4-(4'-(azetidin-1-ylsulfonyl)-[1,1'-biphenyl]-4-yl)-3,6-dihydropyridin-1(2H)-yl)-N-hydroxy-2-methyl-2-(methylsulfonyl)butanamide;
69) 4'-(1-(4-(hydroxyamino)-3-methyl-3-(methylsulfonyl)-4-oxobutyl)-1,2,3,6-tetrahydropyridin-4-yl)-[1,1'-biphenyl]-4-yl methanesulfonate;
70) N-hydroxy-2-methyl-2-(methylsulfonyl)-4-(4-(4-(thiophen-3-yl)phenyl)-3,6-dihydropyridin-1(2H)-yl)butanamide;
71) N-hydroxy-4-(4-(4-(3-methoxythiophen-2-yl)phenyl)-3,6-dihydropyridin-1(2H)-yl)-2-methyl-2-(methylsulfonyl)butanamide;
72) N-hydroxy-2-methyl-2-(methylsulfonyl)-4-(4-(4-(4-methylthiophen-2-yl)phenyl)-3,6-dihydropyridin-1(2H)-yl)butanamide;
73) 4-(4-(4'-(ethylsulfonyl)-[1,1'-biphenyl]-4-yl)-3,6-dihydropyridin-1(2H)-yl)-N-hydroxy-2-methyl-2-(methylsulfonyl) butanamide;
74) N-hydroxy-2-methyl-2-(methylsulfonyl)-4-(4-(4'-(morpholinomethyl)-[1,1'-biphenyl]-4-yl)-3,6-dihydropyridin-1(2H)-yl)butanamide;
75) N-hydroxy-4-(6-(3-methoxyprop-1-yn-1-yl)-3',6'-dihydro-[3,4'-bipyridin]-1' (2'H)-yl)-2-methyl-2-(methylsulfonyl) butanamide;
76) 3-(4-([1,1'-biphenyl]-4-yl)-3,6-dihydropyridin-1(2H)-yl)-N-hydroxy-2-methyl-2-(methylsulfonyl)propanamide;
77) 4-(4-(4-(3-(dimethylamino)prop-1-yn-1-yl)-3-methylphenyl)-3,6-dihydropyridin-1(2H)-yl)-N-hydroxy-2-methyl-2-(methylsulfonyl) butanamide; and
78) 4-(4-(4-(3-(dimethylamino)prop-1-yn-1-yl)-3-(trifluoromethyl)phenyl)-3,6-dihydropyridin-1(2H)-yl)-N-hydroxy-2-methyl-2-(methylsulfonyl)butanamide.

In the present disclosure, the pharmaceutically acceptable salts are preferably acid addition salts formed with pharmaceutically acceptable free acids. Free acids that may be used in the present disclosure include organic acids and inorganic acids. The inorganic acids include hydrochloric acid, hydrobromic acid, sulfuric acid, phosphoric acid, etc, and the organic acids include citric acid, oxalic acid, acetic acid, lactic acid, maleic acid, coumaric acid, gluconic acid, methanesulfonic acid, glycolic acid, succinic acid, 4-toluenesulfonic acid, trifluoroacetic acid, glutamic acid, aspartic acid, etc.

In addition, the compounds of formula I or pharmaceutically acceptable salts thereof can show polymorphism, and can also exist as solvates (e.g., hydrates, etc.). Furthermore, the compounds of the present disclosure can also exist as individual stereoisomer of mixtures of stereoisomers.

Methods for Preparation of the Tetrahydropyridine Derivative Compounds

The present disclosure provides methods for the preparation of the tetrahydropyridine derivative compounds presented by formula I, stereoisomers thereof, or pharmaceutically acceptable salts thereof.

The compounds of the present disclosure can be prepared in accordance with one or more of schemes discussed below.

These methods can be used either directly or with obvious variations to trained chemists to prepare key intermediates and certain compounds of this invention Suitable synthetic sequence are readily selected per specific structures of this invention, but within the art known to individuals practicing organic synthesis, such as method summarized in available chemistry data bases, as in CAS Scifinder and Elesvier Reaxys. Based on these general methods, the enablement for making the compounds of the present disclosure is straightforward and can be practiced within a common professional knowledge.

Some general synthetic methods to prepare the compounds of the present disclosure are illustrated below.

[General Procedure 1]
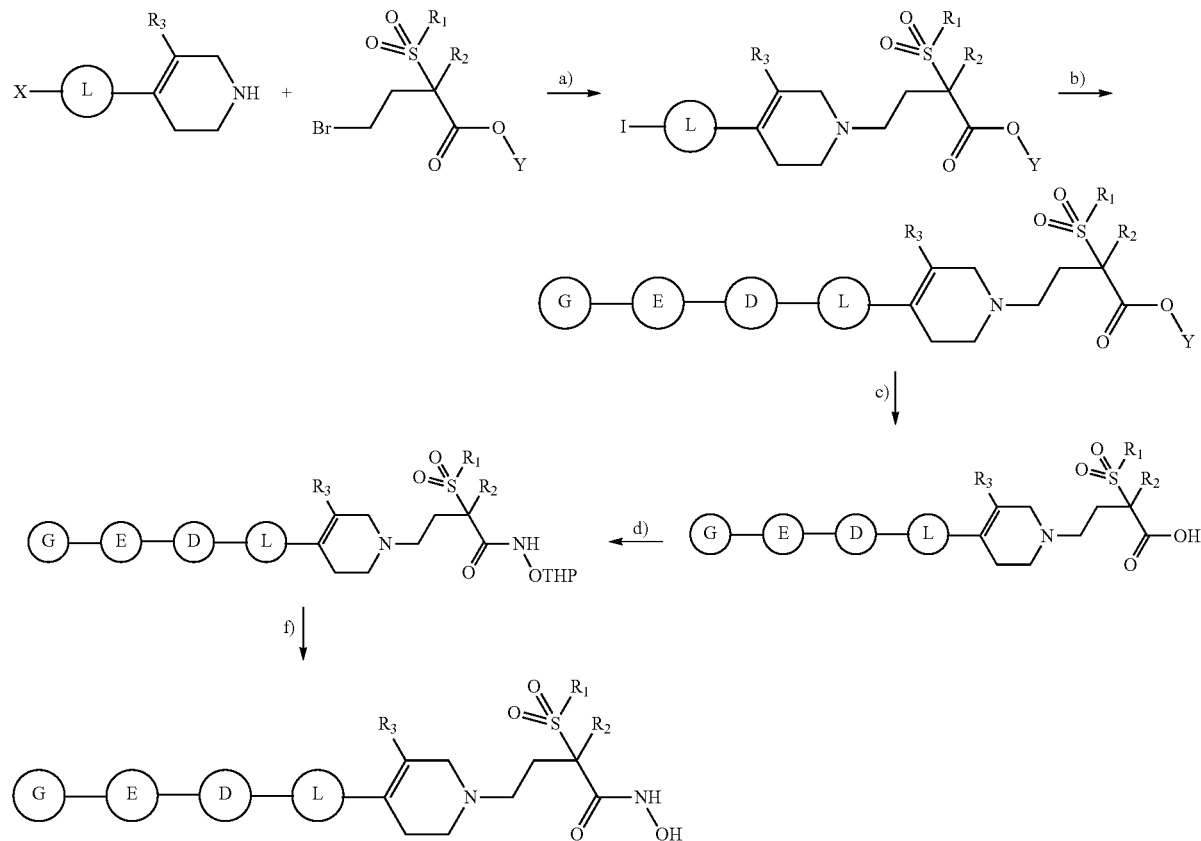
a) Et$_3$N, DMF; b) boronic acid, Pd(PPh$_3$)$_2$Cl$_2$, K$_2$CO$_3$, 1,4-Dioxane, H$_2$O, heat or Acetylene, Pd(PPh$_3$)$_2$Cl$_2$, Et$_3$N, CuI, DMF, heat; c) LiOH, THF, MeOH, H$_2$O;
e) HATU, HOBT, Et$_3$N, NH$_2$—OTHP, DMF; f) HCl, MeOH
[General Procedure 2]
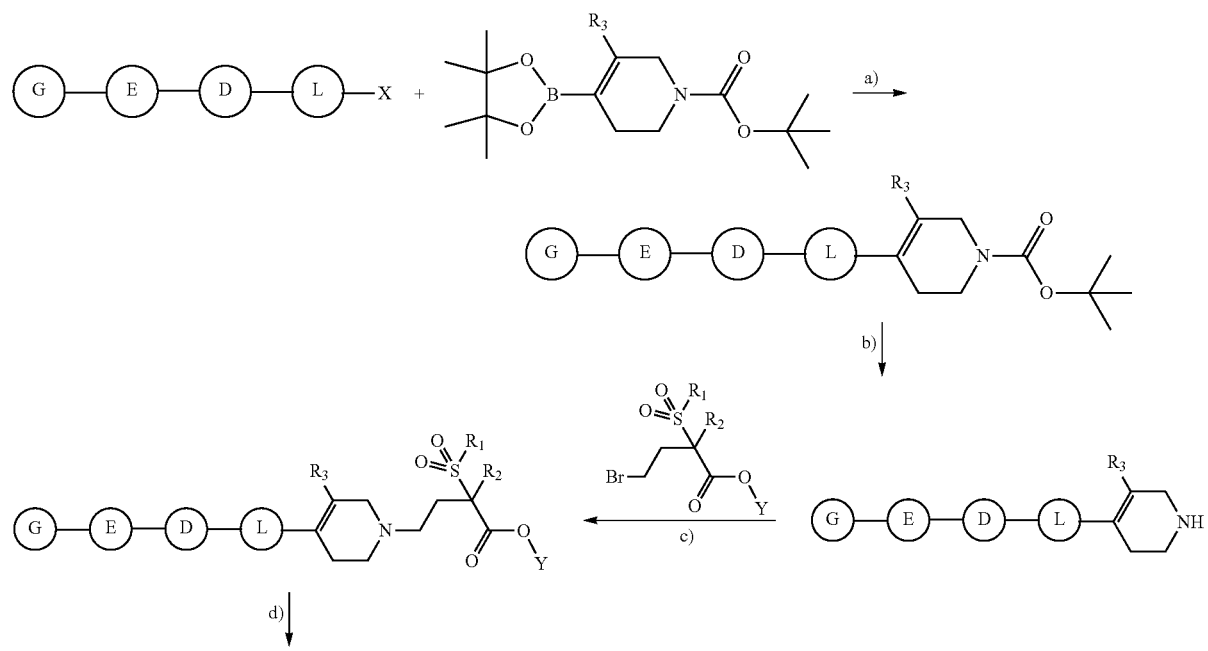

-continued

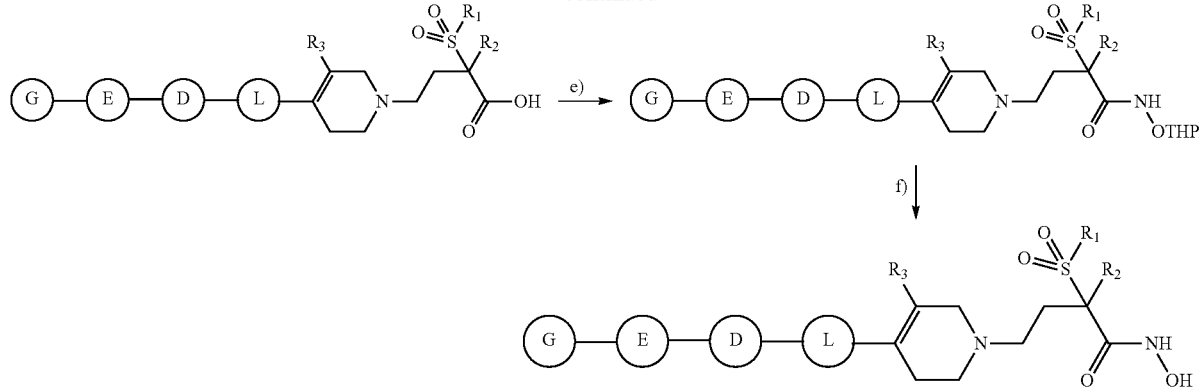

a) Pd(PPh₃)₂Cl₂, K₂CO₃, 1,4-Dioxane, H₂O, heat; b) TFA, Dichloromethane; c) Et₃N, DMF; d) LiOH, THF, MeOH, H₂O;
e) HATU, HOBT, Et₃N, NH₂—OTHP, DMF; f) HCl, MeOH Use of the Tetrahydropyidine Derivative Compounds The present invention provides a pharmaceutical composition for preventing or treating bacterial infections, which contains a pharmaceutically acceptable carrier and, as an active ingredient, a compound represented by the following formula I, a stereoisomer thereof or a pharmaceutically acceptable salt thereof:

[Formula I]

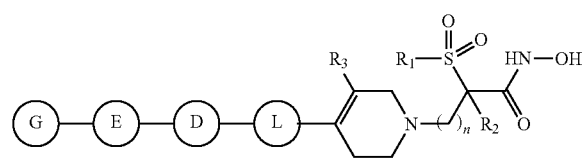

wherein formula I is as defined above.

The compounds of formula I according to the present disclosure, the stereoisomers thereof, or the pharmaceutically acceptable salts thereof, exhibit antibacterial activity, especially against Gram-negative organisms and are therefore suitable to treat bacterial infections in mammals, especially humans. They may therefore be used for the prevention or treatment of bacterial infection caused by Gram-negative bacteria, especially those caused by susceptible and multi-drug resistant Gram-negative bacteria. Examples of such Gram-negative bacteria include *Acinetobacter baumannii, Acinetobacter* spp., *Achromobacter* spp., *Aeromonas* spp., *Bacteroides* spp., *Bordetella* spp., *Borrelia* spp., *Brucella* spp., *Campylobacter* spp., *Chlamydia* spp., *Citrobacter* spp., *Enterobacter aerogenes, Enterobacter cloacae, Escherichia coli, Francisella tularensis, Fusobacterium* spp., *Haemophilus influenza* (beta-lactamase positive and negative), *Helicobacter pylori, Klebsiella oxytoca, Klebsiella pneumonia* (including those encoding extended-spectrum beta-lactamases (hereinafter "ESBLs")), *Legionella pneumophila, Moraxella catarrhalis* (beta-lactamase positive and negative), *Morganella morganii, Neisseria gonorrhoeae, Neisseria meningitides, Proteus vulgaris, Porphyromonas* spp., *Prevotella* spp., members of the Enterobacteriaceae that express ESBLs KPCs, CTX-M, metallo-beta-lactamase, and AmpC-type beta-lactamases that confer resistance to currently available cephalosporins, cephamycins, carbapenems, and beta-lactam/beta-lactamase inhibitor combination, *Mannheimia haemolyticus, Pasteurella* spp., *Proteus mirabilis, Providencia* spp., *Pseudomonas aeruginosa* (including ceftazidime-, cefpirome- and cefeprime-resistant *P. aeruginosa*, carbapenem-resistant *P. aeruginosa* or quinolone-resistant *P. aeruginosa*), *Pseudomonas* spp., *Salmonella* spp., *Shigella* spp., *Serratia marcescenes, Treponema* spp., *Burkholderia cepacia, Vibrio* spp., *Yersinia* spp., and *Stenotrophomonas malophilia*.

In a more specific embodiment, examples of such Gram-negative bacteria include *Acinetobacter baumannii, Acinetobacter* spp., *Enterobacter aerogenes, Enterobacter cloacae, Escherichia coli, Klebsiella oxytoca, Klebsiella pneumonia, Serratia marcescens, Pseudomonas aeruginosa* and members of the Enterobacteriaceae and *Pseudomonas* that express ESBLs, KPSs, CTX-M, metallo-beta-lactamases, and AmpC-type beta-lactamases that confer resistance to currently available cephalosporins, cephamycins, carbapenems, and beta-lactam/beta-lactamase inhibitor combinations.

The compounds of formula I according to the present disclosure or the stereoisomers, or the pharmaceutically acceptable salts thereof, may therefore be used for the prevention or treatment of bacterial infection selected from nosocomial pneumonia, urinary tract infections, systemic infections (such as bacteraemia and sepsis), skin and soft tissue infections, surgical infections, intraabdominal infections, lung infections (including those in patients with cystic fibrosis), endocarditis, diabetic foot infection, osteomyelitis, and central nervous system infections.

The compounds of formula I according to the present disclosure or the stereoisomers display intrinsic antibacterial properties and have the ability to improve permeability of the outer membrane of Gram-negative bacteria to other antibacterial agents. Their use in combination with another antibacterial agent might offer some further advantages such as lowered side-effects of drugs due to lower doses used or shorter time of treatment, more rapid cure of infection shortening hospital stays, increasing spectrum of pathogens controlled, and decreasing incidence of development of resistance to antibiotics. The antibacterial agent for use in combination with a compound of formula I according to the present disclosure will be selected from the group consisting a penicillin antibiotic (such as ampicillin, piperacillin, penicillin G, amoxicillin, or tetracillin), a cephalosporin antibiotic (such as ceftriaxone, ceftazidime, cefepime, cefotaxime), a carbapenem antibiotic (such as imipenem, or meropenem), a monobactam antibiotic (such as aztreonam), a fluoroquinolone antibiotic (such as ciprofloxacin, moxifloxacin or levofloxacin), a macrolide antibiotics (such as erythromycin or azithromycin), an aminoglycoside antibiotic (such as amikacin, gentamycin or tobramycin), a glycopeptide antibiotic (such as vancomycin or teicoplanin), a tetracycline antibiotics (such as tetracycline), and linezolid, clindamycin, telavancin, daptomycin, novobiocin, rifampicin and polymyxin.

In order to exhibit this antibacterial activity, the compounds need to be administered in a therapeutically effective amount. A "therapeutically effective amount" is meant to describe a sufficient quantity of the compound to treat the infection, at a reasonable benefit/risk ratio applicable to any such medical treatment. It will be understood, however, that the attending physician, within the scope of sound medical judgment, will decide the total daily dosage of the compound. The specific therapeutically effective dose level for any particular patient will depend upon a variety of factors including the disorder being treated and the severity of the disorders; the activity of the specific compound employed; the specific composition employed; the age, body weight, general health, sex and diet of the patient; the time of administration; the duration of the treatment; drugs used in combination or coincidental with the specific compound employed; and like factors well known in the medical arts. As a general guideline however, the total daily dose will typically range from about 0.1 mg/kg/day to about 5,000 mg/kg/day in single or in divided doses. Typically, dosages for humans will range from about 10 mg to about 3,000 mg per day, in a single or multiple doses.

Any route typically used to treat infectious illness, including oral, parenteral, topical, rectal, transmucosal, and intestinal, can be used to administer the compounds. Parenteral administrations include injections to generate a systemic effect or injections directly into the afflicted area. Examples of parenteral administrations are subcutaneous, intravenous, intramuscular, intradermal, intrathecal, and intraocular, intranasal, intraventricular injections or infusions techniques. Topical administrations include the treatment of areas readily accessible by local application, such as, for example, eyes, ears including external and middle ear infections, vaginal, open wound, skin including the surface skin and the underneath dermal structures, or other lower intestinal tract. Transmucosal administration includes nasal aerosol or inhalation applications.

The present disclosure also provides a method of inhibiting UDP-3-O—(R-3-hydroxymyristoyl)-N-acetylglucosamine deacetylase (LpxC), comprising administering to a patient in need thereof a therapeutically effective amount of the compound represented by formula I, stereoisomer thereof or pharmaceutically acceptable salt thereof according to the present disclosure. In some embodiments, the present disclosure provides a method of inhibiting UDP-3-O—(R-3-hydroxymyristoyl)-N-acetylglucosamine deacetylase (LpxC), comprising contact a cell (e.g., in vivo or in vitro) with a therapeutically effective amount of the compound represented by formula I, stereoisomer thereof or pharmaceutically acceptable salt thereof according to the present disclosure The present disclosure also provides a method for treating bacterial infections, comprising administering to a patient in need thereof a therapeutically effective amount of the compound represented by formula I, stereoisomer thereof or pharmaceutically acceptable salt thereof according to the present disclosure.

The present disclosure also provides the use of the compound represented by formula I, stereoisomer thereof or pharmaceutically acceptable salt thereof according to the present disclosure in preparation of a medicament for treating bacterial infections.

Advantageous Effects

The compounds represented by formula I, stereoisomers thereof or pharmaceutically acceptable salts thereof according to the present disclosure can exhibit excellent effects on the treatment bacterial infections.

MODE FOR INVENTION

Examples

Embodiments of the present disclosure are described in the following examples, which are meant to illustrate and not limit the scope of this invention. Common abbreviations well known to those with ordinary skills in the synthetic used throughout.

All chemical reagents were commercially available. Flash column chromatography means silica gel chromatography unless specified otherwise, which was performed on Teledyne Combiflash-RF-200 system. $^1$H NMR spectra ($\delta$,ppm) are recorded on 400 MHz or 600 MHz instrument. Mass spectroscopy data for a positive ionization method are provided.

Preparation 1: Synthesis of Intermediate 1 {methyl 4-bromo-2-methyl-2-(methylsulfonyl)butanoate}

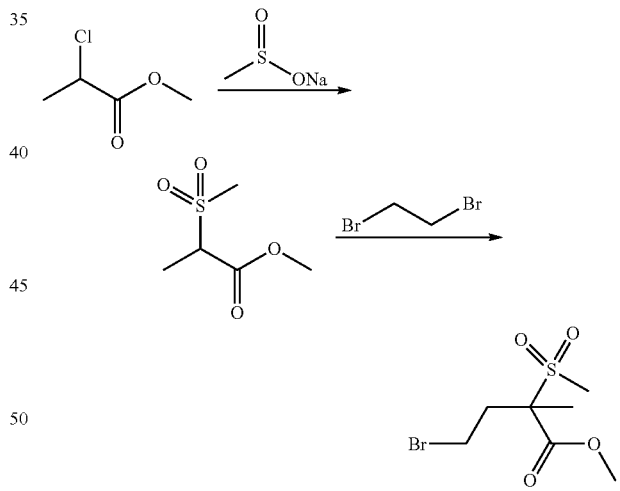

Step 1: Synthesis of methyl 2-(methylsulfonyl)propanoate

To a solution of methyl 2-chloropropionate (150 g, 1 eq) in MeOH (500 ml) was added with sodium methanesulfinate (162 g, 1.3 eq) and stirred for 20 hr at 77° C. The mixture was cooled down to room temperature and precipitated solid was filtered off through celite. The filtrate was concentrated in vacuo and the residue was suspended in ethyl acetate (100 ml)/hexane (500 ml). After then, the precipitated solid was filtered off and the filtrate was concentrated in vacuo to prepare the title compound (162 g, 80%).

¹H NMR (600 MHz, CDCl₃-d1); δ3.90 (q, J=7.2 Hz, 1H), 3.82 (s, 3H), 3.03 (s, 3H), 1.66 (d, J=6.6 Hz, 3H).

Step 2: Synthesis of methyl 4-bromo-2-methyl-2-(methylsulfonyl)butanoate

To a suspended solution of sodium hydride (60%, 33.7 g, 2 eq) in DMF (300 ml) was dropwised with methyl 2-(methylsulfonyl)propanoate (70 g, 1 eq) in DMF (100 ml) at 0° C. and stirred for 30 min. After then, the mixture was added with 1,2-dibromoethane (158 g, 2 eq) and stirred for 6 hr at room temperature. The mixture was quenched with sat. aq. NH₄Cl, extracted with ethyl acetate and water. The organic layer was washed with brine, dried over anhydrous MgSO₄ and concentrated in vacuo. The residue was purified with column chromatography to prepare the title compound (225 mg, 43%).

¹H NMR (600 MHz, CDCl₃-d1); δ3.81 (s, 3H), 3.49-3.45 (m, 1H), 3.35-3.31 (m, 1H), 3.01 (s, 3H). 2.78-2.73 (m, 1H), 2.53-2.48 (m, 1H), 1.62 (s, 3H)

Preparation 2: Synthesis of Intermediate 2 {methyl 4-(4-(4-iodophenyl)-3,6-dihydropyridin-1(2H)-yl)-2-methyl-2-(methylsulfonyl)butanoate}

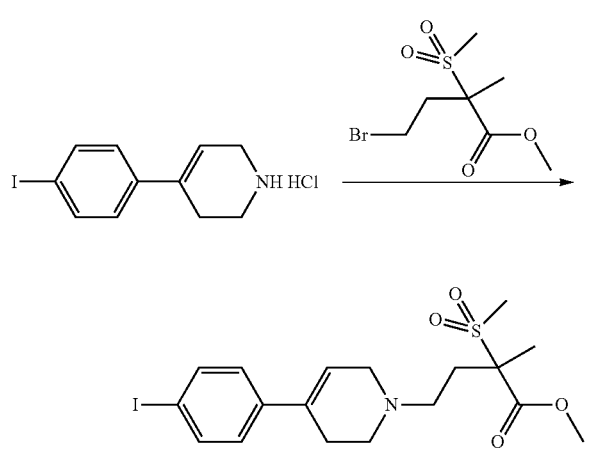

To a solution of 4-(4-iodophenyl)-1,2,3,6-tetrahydropyridine hydrochloride (10 g, 1 eq) in a mixture of DMF (100 ml)/MeOH (50 ml) was added with methyl 4-bromo-2-methyl-2-(methylsulfonyl)butanoate (12.74 g, 1.5 eq), N,N-diisopropylethylamine (16.3 ml, 3 eq) and stirred for 24 hr at 60° C. The mixture was cooled down to room temperature, extracted with ethyl acetate and water. The organic layer was washed with brine, dried over anhydrous MgSO₄ and concentrated in vacuo. The residue was purified with column chromatography to prepare the title compound (11 g, 74%).

¹H NMR (600 MHz, CDCl₃-d1); δ7.68 (d, J=7.8 Hz, 2H), 7.10 (d, J=8.4 Hz, 2H), 5.98 (s, 1H), 4.20-4.14 (m, 1H), 3.88 (d, J=6.0 Hz, 3H), 3.72-3.66 (m, 1H), 3.62-3.48 (m, 2H), 3.46-3.36 (m, 1H), 3.30-3.14 (m, 2H), 3.13 (d, J=6.6 Hz, 3H), 2.94-2.84 (m, 1H), 2.80-2.65 (m, 2H), 1.76 (d, J=6.6 Hz, 3H).

Preparation 3: Synthesis of Intermediate 3 {4-(4-(4-iodophenyl)-3,6-dihydropyridin-1(2H)-yl)-2-methyl-2-(methylsulfonyl)-N-((tetrahydro-2H-pyran-2-yl)oxy)butanamide}

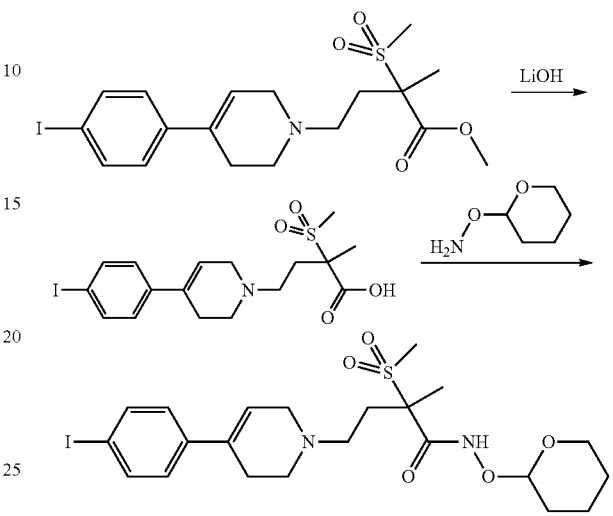

Step 2: Synthesis of 4-(4-(4-iodophenyl)-3,6-dihydropyridin-1(2H)-yl)-2-methyl-2-(methylsulfonyl)-N-((tetrahydro-2H-pyran-2-yl)oxy)butanamide To a solution of 4-(4-(4-iodophenyl)-3,6-dihydropyridin-1(2H)-yl)-2-methyl-2-(methylsulfonyl)butanoic acid (1.76 g, 1 eq) in DMF (10 ml) was added with HATU (1-[Bis(dimethylamino)methylene]-1H-1,2,3-triazolo[4,5-b]pyridinium 3-oxid hexafluorophosphate) (2.02 g, 1.4 eq), HOBT (Hydroxybenzotriazole) (0.81 g, 1.4 eq), Et₃N (1.6 ml, 3 eq), O-(tetrahydro-2H-pyran-2-yl)hydroxylamine hydrochloride (1.17 g, 2 eq) and stirred for 1 hr at room temperature. The mixture was extracted with ethyl acetate and water. The organic layer was washed with brine, dried over anhydrous MgSO₄ and concentrated in vacuo. The residue was purified with column chromatography to prepare the title compound (0.6 g, 28%).

¹H NMR (600 MHz, DMSO-d6); δ11.58 (bs, 1H), 7.66-7.64 (m, 2H), 7.22-7.20 (m, 2H), 6.17 (s, 1H), 4.85-4.81 (m, 1H), 3.31-3.04 (m, 5H), 2.60-2.59 (m, 2H), 2.47-2.39 (m, 6H), 1.85-1.62 (m, 2H), 1.47-1.41 (s, 7H).

Example 1: Synthesis of 4-(4-(4-((4-(dimethylamino)phenyl) ethynyl)phenyl)-3,6-dihydropyridin-1(2H)-yl)-N-hydroxy-2-methyl-2-(methylsulfonyl)butanamide

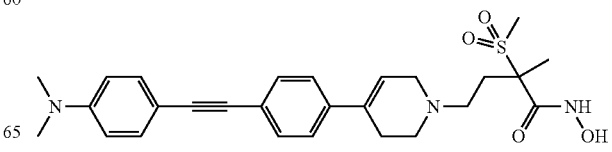

Step 1: Synthesis of methyl 4-(4-(4-((4-(dimethyl-amino)phenyl)ethynyl)phenyl)-3,6-dihydropyridin-1(2H)-yl)-2-methyl-2-(methylsulfonyl)butanoate Step 2: Synthesis of 4-(4-(4-((4-(dimethylamino)phenyl)ethynyl)phenyl)-3,6-dihydropyridin-1(2H)-yl)-2-methyl-2-(methylsulfonyl)butanoic acid

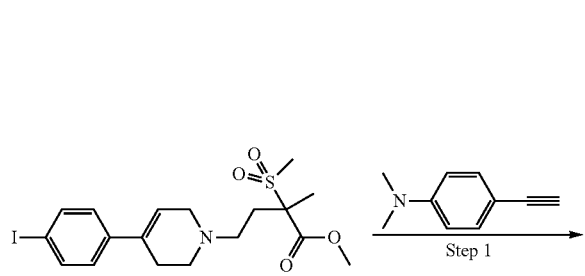

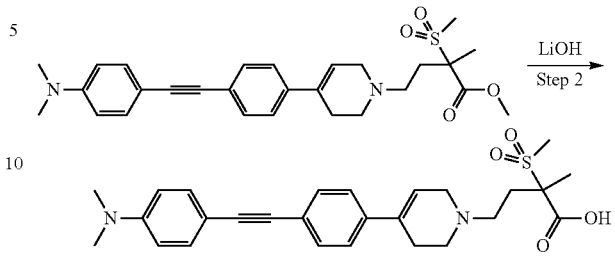

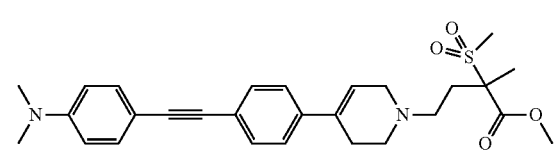

To a solution of methyl 4-(4-(4-iodophenyl)-3,6-dihydropyridin-1(2H)-yl)-2-methyl-2-(methylsulfonyl)butanoate (Intermediate 2) (500 mg, 1 eq) in a mixture of THF (10 ml)/toluene (10 ml) was added with CuI (20 mg, 0.1 eq), Pd(PPh₃)₂Cl₂ (74 mg, 0.1 eq), Et₃N (0.442 ml, 3 eq) and 4-ethynyl-N,N-dimethylaniline (228 mg, 1.5 eq) and stirred for 12 hr at room temperature. The mixture was extracted with ethyl acetate and water. The organic layer was washed with brine, dried over anhydrous MgSO₄ and concentrated in vacuo. The residue was purified with column chromatography to prepare the title compound (225 mg, 43%).

¹H NMR (600 MHz, CDCl₃-d1); δ7.43 (d, J=8.4 Hz, 2H), 7.39 (d, J=9 Hz, 2H), 7.32 (d, J=9 Hz, 2H), 6.65 (d, J=8.4 Hz, 2H), 6.08 (s, 1H), 3.87 (s, 3H), 3.24-3.22 (m, 1H), 3.07-3.05 (m, 1H), 3.04 (s, 3H), 2.98 (s, 6H), 2.82-2.76 (m, 1H), 2.67-2.56 (m, 4H), 2.62-2.58 (m, 2H), 2.03-2.00 (m, 1H), 1.63 (s, 3H).

MS (ESI, m/z): 495.3 [M+H]⁺.

To a solution of methyl 4-(4-(4-((4-(dimethylamino)phenyl)ethynyl)phenyl)-3,6-dihydropyridin-1(2H)-yl)-2-methyl-2-(methylsulfonyl)butanoate (225 mg, 1 eq) in a mixture of THF (8 ml)/MeOH (2 ml) was added with 2N—LiOH (0.68 mL, 3 eq) solution and stirred for 2 hr at room temperature. The solvent was removed under reduced pressure and the residue was diluted with water (6 ml), adjusted the pH to 4.0. The precipitated solid was filtered off to prepare the title compound (190 mg, 87%), which was used for next step without further purification.

MS (ESI, m/z): 481.2 [M+H]⁺.

Step 3: Synthesis of 4-(4-(4-((4-(dimethylamino)phenyl)ethynyl)phenyl)-3,6-dihydropyridin-1(2H)-yl)-2-methyl-2-(methylsulfonyl)-N-((tetrahydro-2H-pyran-2-yl)oxy)butanamide

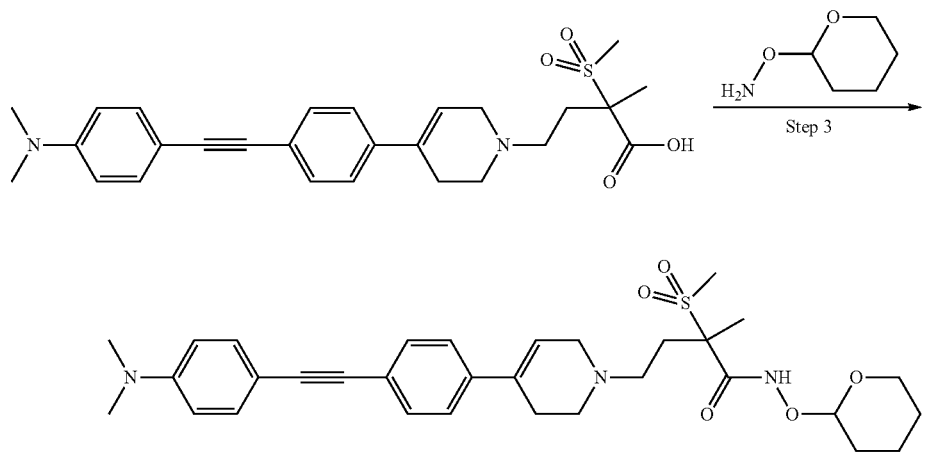

To a solution of 4-(4-(4-((4-(dimethylamino)phenyl)ethynyl)phenyl)-3,6-dihydropyridin-1(2H)-yl)-2-methyl-2-(methylsulfonyl)butanoic acid (190 mg, 1 eq) in DMF (10 ml) was added with HATU (210 mg, 1.4 eq), HOBT (85 mg, 1.4 eq), Et₃N (0.17 ml, 3 eq), O-(tetrahydro-2H-pyran-2-yl)hydroxylamine hydrochloride (121 mg, 2 eq) and stirred for 1 hr at room temperature. The mixture was extracted with ethyl acetate and water. The organic layer was washed with brine, dried over anhydrous MgSO₄ and concentrated in vacuo. The residue was purified with column chromatography to prepare the title compound (200 mg, 87%).

MS (ESI, m/z): 580.3 [M+H]⁺.

Step 4: Synthesis of 4-(4-(4-((4-(dimethylamino)phenyl)ethynyl)phenyl)-3,6-dihydropyridin-1(2H)-yl)-N-hydroxy-2-methyl-2-(methylsulfonyl)butanamide

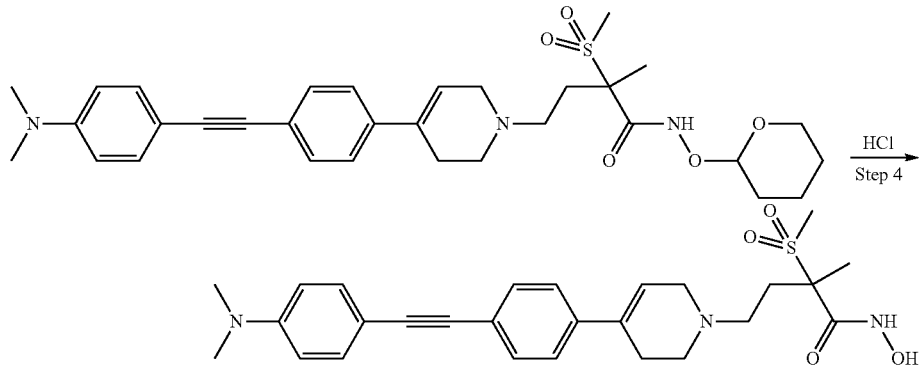

To a solution of 4-(4-(4-((4-(dimethylamino)phenyl)ethynyl)phenyl)-3,6-dihydropyridin-1(2H)-yl)-2-methyl-2-(methylsulfonyl)-N-((tetrahydro-2H-pyran-2-yl)oxy)butanamide (200 mg, 1 eq) in MeOH (6 ml) was added with HCl solution in MeOH (1.25N, 0.83 ml, 3 eq) and stirred for 2 hr at room temperature. The solvent was removed under reduced pressure and the residue was diluted with water (6 ml), adjusted the pH to 7.0. The water was concentrated in vacuo and the resulting residue was purified with column chromatography to prepare the title compound (40 mg, 24%).

$^1$H NMR (600 MHz, DMSO-d6); δ11.02 (bs, 1H), 9.08 (bs, 1H), 7.42-7.39 (m, 4H), 7.32 (d, J=8.4 Hz, 2H), 6.68 (d, J=9 Hz, 2H), 6.21 (s, 1H), 3.12-3.08 (m, 2H), 3.04 (s, 3H), 2.92 (s, 6H), 2.67-2.56 (m, 2H), 2.47-2.39 (m, 4H), 2.36-2.28 (m, 1H), 1.85-1.80 (m, 1H), 1.44 (s, 3H).

MS (ESI, m/z): 496.2 [M+H]$^+$.

Examples 2-14

The terminal acetylenes listed in the following table were used to prepare compounds of Examples 2-14 in the same manner as Example 1.

| Example | Structure (Name) | Terminal acetylene |
|---|---|---|
| | (N-hydroxy-2-methyl-2-(methylsulfonyl)-4-(4-(4-(phenylethynyl)phenyl)-3,6-dihydropyridin-1(2H)-yl)butanamide)<br>$^1$H NMR (600 MHz, DMSO-d6); δ 11.00 (bs, 1H), 9.09 (bs, 1H), 7.52-7.39 (m, 9H), 6.23 (s, 1H), 3.34-3.28 (m, 6H), 3.09-3.03 (m, 2H), 3.03 (s, 3H), 2.63-2.57 (m, 2H), 1.44 (s, 3H).<br>MS (ESI, m/z): 453.2 [M + H]$^+$. | |
| | (N-hydroxy-4-(4-(4-((4-methoxyphenyl)ethynyl)phenyl)-3,6-dihydropyridin-1(2H)-yl)-2-methyl-2-(methylsulfonyl)butanamide)<br>$^1$H NMR (600 MHz, DMSO-d6); δ 11.01 (bs, 1H), 9.10 (bs, 1H), 7.47-7.43 (m, 6H), 6.99-6.95 (m, 2H), 6.23 (s, 1H), 3.76 (s, 3H), 3.13-3.06 (m, 2H), 3.04 (s, 3H), 2.65-2.54 (m, 2H), 2.46-2.40 (m, | |

| Example | Structure (Name) | Terminal acetylene |
|---|---|---|
| | 4H) 2.36-2.28 (m, 1H), 1.85-1.81 (m, 1H), 1.44 (s, 3H).<br>MS (ESI, m/z): 483.2 [M + H]⁺. | |
| 4 | 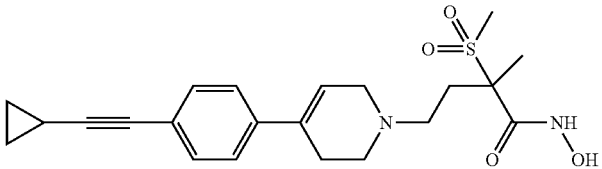 [SMILES: CC(CCN1CC=C(c2ccc(C#CC3CC3)cc2)CC1)(C(=O)NO)S(C)(=O)=O]<br>(4-(4-(4-(cyclopropylethynyl)phenyl)-3,6-dihydropyridin-1(2H)-yl)-N-hydroxy-2-methyl-2-(methylsulfonyl)butanamide)<br>¹H NMR (600 MHz, DMSO-d6); δ 11.01 (bs, 1H), 9.09 (bs, 1H), 7.36-7.35 (m, 2H), 7.28-7.27 (m, 2H), 6.17 (s, 1H), 3.10-3.04 (m, 2H), 3.03 (s, 3H), 2.63-2.54 (m, 2H), 2.46-2.39 (m, 4H), 2.31-2.26 (m, 1H), 1.83-1.77 (m, 1H), 1.53-1.47 (m, 1H), 1.44 (s, 3H), 0.86-0.82 (m, 2H), 0.70-0.65 (m, 2H).<br>MS (ESI, m/z): 417.1 [M + H]⁺. | 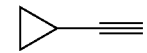 |
| | 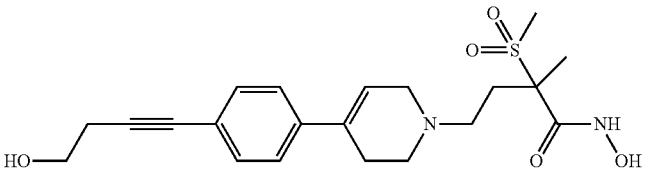 [SMILES: CC(CCN1CC=C(c2ccc(C#CCCO)cc2)CC1)(C(=O)NO)S(C)(=O)=O]<br>(N-hydroxy-4-(4-(4-(4-hydroxybut-1-yn-1-yl)phenyl)-3,6-dihydropyridin-1(2H)-yl)-2-methyl-2-(methylsulfonyl)butanamide)<br>¹H NMR (600 MHz, DMSO-d6); δ 11.03 (bs, 1H), 9.13 (bs, 1H), 7.41-7.39 (m, 2H), 7.34-7.33 (m, 2H), 6.21 (s, 1H), 4.91 (m, 1H), 3.59-3.54 (m, 2H), 3.18-3.11 (m, 2H), 3.06 (s, 3H), 2.80-2.74 (m, 4H), 2.56-2.54 (m, 2H), 2.48-2.42 (m, 2H), 2.38-2.33 (m, 1H), 1.86-1.83 (m, 1H), 1.47 (s, 3H).<br>MS (ESI, m/z): 421.2 [M + H]⁺. | |
| 6 | <br>(4-(4-(4-(hex-1-yn-1-yl)phenyl)-3,6-dihydropyridin-1(2H)-yl)-N-hydroxy-2-methyl-2-(methylsulfonyl)butanamide)<br>¹H NMR (600 MHz, DMSO-d6); δ 11.00 (bs, 1H), 9.08 (bs, 1H), 7.39-7.35 (m, 2H), 7.29-7.28 (m, 2H), 6.17 (s, 1H), 3.34-3.31 (m, 2H), 3.10-3.01 (m, 5H), 2.60-2.35 (m, 2H), 2.48-2.06 (m, 6H), 1.48-1.29 (m, 7H), 0.97-0.88 (m, 3H).<br>MS (ESI, m/z): 433.2 [M + H]⁺. | 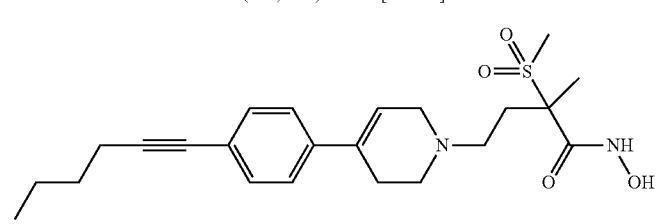 |
| | 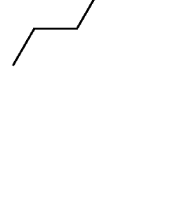<br>(4-(4-(4-(3-(dimethylamino)prop-1-yn-1-yl)phenyl)-3,6-dihydropyridin-1(2H)-yl)-N-hydroxy-2-methyl-2-(methylsulfonyl)butanamide)<br>¹H NMR (600 MHz, DMSO-d6); δ 11.03 (bs, 1H), 9.13 (bs, 1H), 7.43-7.42 (m, 2H), 7.39-7.37 (m, 2H), | |

| Example | Structure (Name) | Terminal acetylene |
|---|---|---|
| | 6.21 (s, 1H), 3.45-3.43 (m, 2H), 3.14-3.09 (m, 2H), 3.06 (s, 3H), 2.67-2.57 (m, 2H), 2.49-2.40 (m, 4H), 2.34-2.26 (m, 2H), 2.23 (s, 6H), 1.46 (s, 3H). MS (ESI, m/z): 434.2 [M + H]⁺. | |

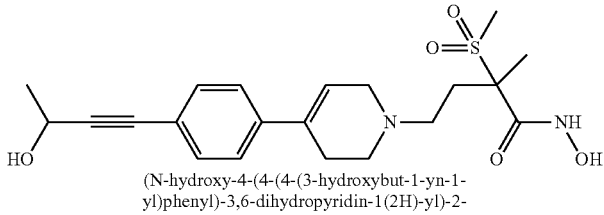

(N-hydroxy-4-(4-(4-(3-hydroxybut-1-yn-1-yl)phenyl)-3,6-dihydropyridin-1(2H)-yl)-2-methyl-2-(methylsulfonyl)butanamide)
¹H NMR (600 MHz, DMSO-d6); δ 11.03 (bs, 1H), 9.12 (bs, 1H), 7.43 (d, J = 7.8 Hz, 2H), 7.35 (d, J = 9.0 Hz, 2H), 6.22 (s, 1H), 5.46 (d, J = 5.4 Hz, 1H), 4.58 (m, 1H), 3.50 (s, 2H), 3.15-3.07 (m, 2H), 3.06 (s, 3H), 2.67-2.57 (m, 2H), 2.48-2.42 (m, 4H), 2.36-2.32 (m, 1H), 1.84-1.80 (m, 1H), 1.46 (s, 3H), 1.37 (d, J = 6.0 Hz, 3H).
MS (ESI, m/z): 421.10 [M + H]⁺.

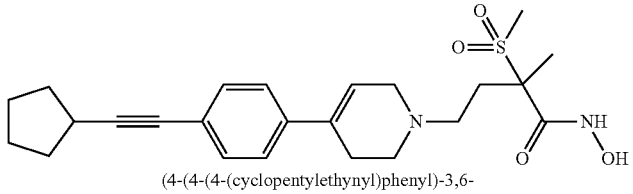

(4-(4-(4-(cyclopentylethynyl)phenyl)-3,6-dihydropyridin-1(2H)-yl)-N-hydroxy-2-methyl-2-(methylsulfonyl)butanamide)
¹H NMR (600 MHz, DMSO-d6); δ 11.03 (bs, 1H), 9.13 (bs, 1H), 7.39 (d, J = 8 Hz, 2H), 7.31 (d, J = 8.8 Hz, 2H), 6.19 (s, 1H), 3.85-3.83 (m, 2H), 3.07-3.04 (m, 4H), 2.81-2.79 (m, 1H), 2.61-2.58 (m, 2H), 2.47-2.44 (m, 3H), 2.00-1.95 (m, 2H), 1.84-1.81 (m, 2H), 1.76-1.74 (m, 2H), 1.62-1.52 (m, 4H), 1.46 (s, 3H).
MS (ESI, m/z): 445.1 [M + H]⁺.

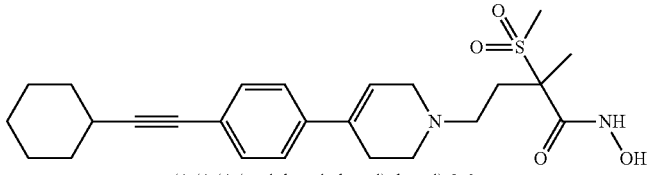

(4-(4-(4-(cyclohexylethynyl)phenyl)-3,6-dihydropyridin-1(2H)-yl)-N-hydroxy-2-methyl-2-(methylsulfonyl)butanamide)
¹H NMR (600 MHz, DMSO-d6); δ 11.01 (bs, 1H), 9.09 (bs, 1H), 7.37 (d, J = 8.4 Hz, 2H), 7.29 (d, J = 7.8 Hz, 2H), 6.17 (s, 1H), 3.10-3.01 (m, 5H), 2.66-2.54 (m, 3H), 2.46-2.39 (m, 5H), 2.31-2.28 (m, 1H), 1.81-1.78 (m, 3H), 1.67-1.64 (m, 2H), 1.48-1.41 (m, 5H), 1.33-1.28 (m, 3H).
MS (ESI, m/z): 459.2 [M + H]⁺.

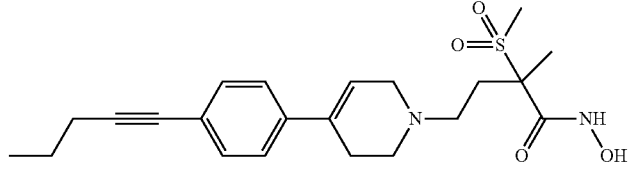 [SMILES: CCCC#Cc1ccc(C2=CCN(CCC(C)(C(=O)NO)S(C)(=O)=O)CC2)cc1]

(N-hydroxy-2-methyl-2-(methylsulfonyl)-4-(4-(4-(pent-1-yn-1-yl)phenyl)-3,6-dihydropyridin-1(2H)-yl)butanamide)
¹H NMR (600 MHz, DMSO-d6); δ 11.01 (bs, 1H), 9.09

| Example | Structure (Name) | Terminal acetylene |
|---|---|---|
|  | (bs 1H), 7.37-7.36 (m, 2H), 7.31-7.29 (m, 2H), 6.17 (s, 1H), 3.10-3.04 (m, 2H), 3.03 (s, 3H), 2.63-2.54 (m, 2H), 2.51-2.49 (m, 1H), 2.45-2.39 (m, 3H), 2.36 (t, J = 6.9 Hz 2H), 2.31-2.28 (m, 1H), 1.83-1.78 (m, 1H), 1.53-1.49 (m, 2H), 1.43 (s, 3H), 0.96 (t, J = 7.8 Hz, 3H).<br>MS (ESI, m/z): 419.1 [M + H]⁺.<br>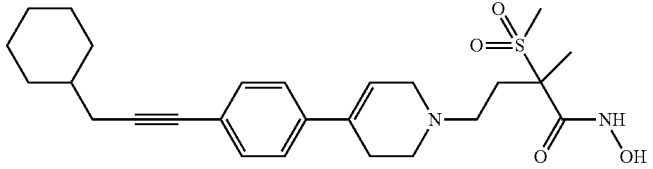<br>(4-(4-(4-(3-cyclohexylprop-1-yn-1-yl)phenyl)-3,6-dihydropyridin-1(2H)-yl)-N-hydroxy-2-methyl-2-(methylsulfonyl)butanamide)<br>¹H NMR (600 MHz, DMSO-d6); δ 11.01 (bs, 1H), 9.11 (bs, 1H), 7.38-7.36 (m, 2H), 7.31-7.29 (m, 2H), 6.19 (s, 1H), 3.18-3.03 (m, 5H), 2.65-2.48 (m, 2H), 2.51-2.43 (m, 2H), 2.32-2.31 (m, 2H), 1.79-1.61 (m, 6H), 1.59-1.40 (m, 4H), 1.24-1.18 (m, 2H), 1.13-1.06 (m, 2H), 1.04-0.98 (m, 2H).<br>MS (ESI, m/z): 473.2 [M + H]⁺. |  |
| 13 | 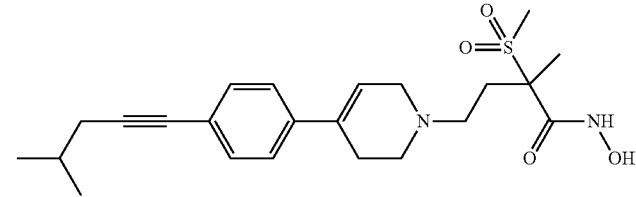 [SMILES: CC(C)CC#Cc1ccc(C2=CCN(CCC(C)(C(=O)NO)S(C)(=O)=O)CC2)cc1]<br>(N-hydroxy-2-methyl-4-(4-(4-(4-methylpent-1-yn-1-yl)phenyl)-3,6-dihydropyridin-1(2H)-yl)-2-(methylsulfonyl)butanamide)<br>¹H NMR (600 MHz, DMSO-d6) δ; 11.01 (bs, 1H), 9.10 (bs, 1H), 7.38-7.37 (m, 2H), 7.32-7.31 (m, 2H), 6.17 (s, 1H), 3.09-3.04 (m, 5H), 2.62-2.57 (m, 2H), 2.46-2.44 (m, 2H), 2.31-2.98 (m, 2H), 1.85-1.81 (m, 2H), 1.44 (s, 3H), 1.23-1.21 (m, 2 H), 0.99-0.96 (m, 6H).<br>MS (ESI, m/z): 433.2 [M + H]⁺. | 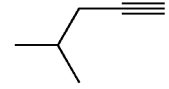 |
|  | 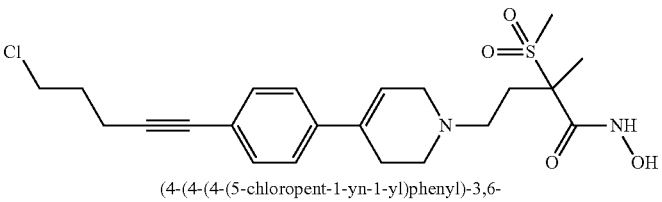<br>(4-(4-(4-(5-chloropent-1-yn-1-yl)phenyl)-3,6-dihydropyridin-1(2H)-yl)-N-hydroxy-2-methyl-2-(methylsulfonyl)butanamide)<br>¹H NMR (600 MHz, DMSO-d6); δ 11.0 (bs, 1H), 9.15 (bs, 1H), 7.38-7.37 (m, 2H), 7.33-7.32 (m, 2H), 6.18 (s, 1H), 3.78 (t, J = 7.2 Hz, 2H), 3.12-3.06 (m, 2H), 3.04 (s, 3H), 2.68-2.56 (m, 4H), 2.46-2.40 (m, 5H), 1.98-1.90 (m, 2H), 1.82-1.79 (m, 1H), 1.44 (s, 3H).<br>MS (ESI, m/z): 453.2 [M + H]⁺. |  |

Example 15: Synthesis of N-hydroxy-2-methyl-2-(methylsulfonyl)-4-(4-(4-(3-(pyrrolidin-1-yl)prop-1-yn-1-yl)phenyl)-3,6-dihydropyridin-1(2H)-yl)butanamide

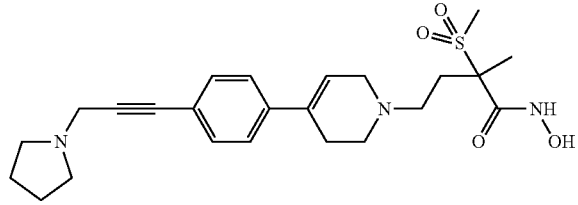 [SMILES: CC(CCN1CC=C(c2ccc(C#CCN3CCCC3)cc2)CC1)(C(=O)NO)S(C)(=O)=O]

Step 1: Synthesis of 1-(prop-2-yn-1-yl)pyrrolidine

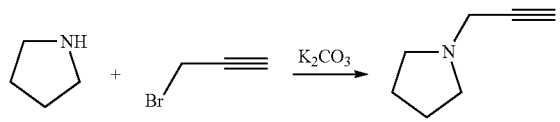

To a solution of pyrrolidine (1.5 ml, 1 eq) in toluene (30 ml) was added with $K_2CO_3$(4.97 g, 2 eq) and 3-bromoprop-1-yne (2.4 ml, 1.5 eq). The mixture was stirred for 15 hr at room temperature and filtered off, and the filtrate was concentrated in vacuo. The resulting residue was purified with column chromatography to prepare the title compound (0.32 g, 16%).

MS (ESI, m/z): 110.1 [M+H]$^+$.

Step 2: Synthesis of N-hydroxy-2-methyl-2-(methylsulfonyl)-4-(4-(4-(3-(pyrrolidin-1-yl)prop-1-yn-1-yl)phenyl)-3,6-dihydropyridin-1(2H)-yl)butanamide The title compound was prepared the procedures described for the synthesis of Example 1 using 1-(prop-2-yn-1-yl) pyrrolidine.

$^1$H NMR (600 MHz, DMSO-d6); δ11.03 (bs, 1H), 9.14 (bs, 1H), 7.45-7.36 (m, 4H), 6.22 (s, 1H), 3.63 (s, 2H), 3.18-3.04 (m, 5H), 2.70-2.56 (m, 6H), 2.48-2.41 (m, 4H), 2.37-2.31 (m, 1H), 1.87-1.80 (m, 1H), 1.77-1.68 (m, 4H), 1.46 (s, 3H).

MS (ESI, m/z): 460.2 [M+H]$^+$.

Example 16: Synthesis of 4-(4-(4-(3-(diethylamino)prop-1-yn-1-yl)phenyl)-3,6-dihydropyridin-1(2H)-yl)-N-hydroxy-2-methyl-2-(methylsulfonyl)butanamide

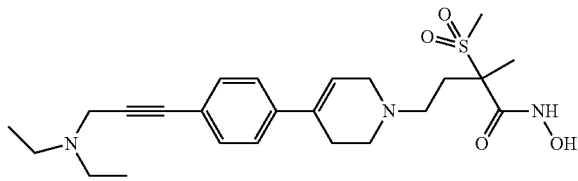 [SMILES: CCN(CC)CC#Cc1ccc(C2=CCN(CCC(C)(C(=O)NO)S(C)(=O)=O)CC2)cc1]

Step 1: Synthesis of N,N-diethylprop-2-yn-1-amine

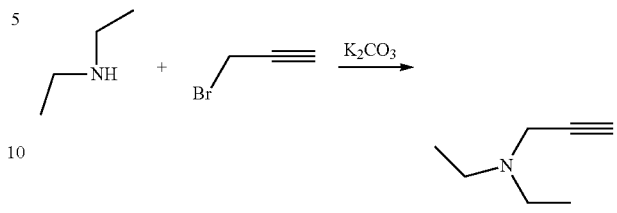

To a solution of diethylamine (0.46 ml, 1 eq) in toluene (10 ml) was added with $K_2CO_3$(1.23 g, 2 eq) and 3-bromoprop-1-yne (0.56 ml, 1.5 eq). The mixture was stirred for 15 hr at room temperature and filtered off, and the filtrate was concentrated in vacuo. The resulting residue was purified with column chromatography to prepare the title compound (0.46 g, 94%).

MS (ESI, m/z): 112.1 [M+H]$^+$.

Step 2: Synthesis of 4-(4-(4-(3-(diethylamino)prop-1-yn-1-yl)phenyl)-3,6-dihydropyridin-1(2H)-yl)-N-hydroxy-2-methyl-2-(methylsulfonyl)butanamide The title compound was prepared the procedures described for the synthesis of Example 1 using N,N-diethylprop-2-yn-1-amine.

$^1$H NMR (600 MHz, DMSO-d6); δ11.02 (bs, 1H), 9.15 (bs, 1H), 7.43-7.37 (m, 4H), 6.22 (s, 1H), 3.70-3.62 (m, 2H), 3.32-3.08 (m, 2H), 3.05 (s, 3H), 2.84-2.78 (m, 6H), 2.74-2.58 (m, 5H), 1.89-1.85 (m, 1H), 1.45 (s, 3H), 1.11-0.96 (m, 6H).

MS (ESI, m/z): 462.2 [M+H]$^+$.

Example 17: Synthesis of N-hydroxy-4-(4-(4-(3-((S)-2-(hydroxymethyl)pyrrolidin-1-yl)prop-1-yn-1-yl)phenyl)-3,6-dihydropyridin-1(2H)-yl)-2-methyl-2-(methylsulfonyl)butanamide

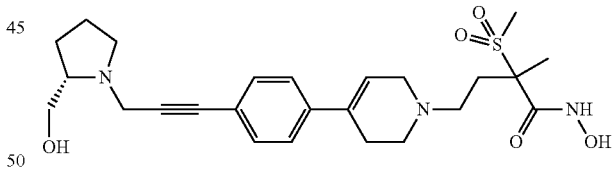

Step 1: Synthesis of (R)-(1-(prop-2-yn-1-yl)pyrrolidin-2-yl)methanol

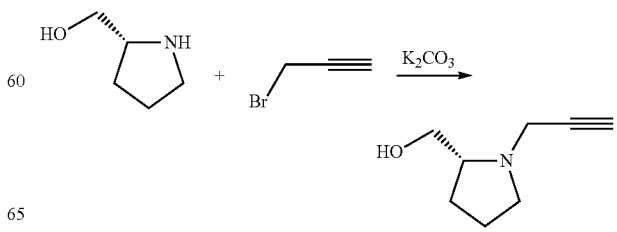

To a solution of 3-bromoprop-1-yne (3 g, 1 eq) in toluene (30 ml) was added with (R)-pyrrolidin-2-ylmethanol (3.73 ml, 1.5 eq) and K$_2$CO$_3$ (6.97 g, 2 eq). The mixture was stirred for 15 hr at room temperature and extracted with ethyl acetate and water. The organic layer was dried over anhydrous MgSO$_4$ and concentrated in vacuo. The residue was purified with column chromatography to prepare the title compound (2 g, 57%).

$^1$H NMR (600 MHz, CDCl$_3$-d1); δ 3.65-3.51 (m, 2H), 3.45-3.41 (m, 2H), 3.04-3.01 (m, 1H), 2.87-2.84 (m, 1H), 2.71-2.67 (m, 1H), 2.20-2.19 (m, 1H), 1.93-1.72 (m, 4H).

Step 2: Synthesis of N-hydroxy-4-(4-(4-(3-((S)-2-(hydroxymethyl)pyrrolidin-1-yl)prop-1-yn-1-yl)phenyl)-3,6-dihydropyridin-1(2H)-yl)-2-methyl-2-(methylsulfonyl)butanamide The title compound was prepared the procedures described for the synthesis of Example 1 using (R)-(1-(prop-2-yn-1-yl)pyrrolidin-2-yl)methanol.

$^1$H NMR (600 MHz, DMSO-d6); δ11.04 (bs, 1H), 9.21 (bs, 1H), 7.48-7.40 (m, 4H), 6.26 (s, 1H), 3.55-3.52 (m, 2H), 3.36-3.33 (m, 4H), 3.09-3.08 (m, 4H), 2.89 (s, 3H), 2.69-2.58 (m, 4H), 1.95-1.87 (m, 1H), 1.79-1.62 (m, 6H), 1.49 (s, 3H).

MS (ESI, m/z): 490.2[M+H]$^+$.

Example 18: Synthesis of N-hydroxy-4-(4-(4-(5-hydroxypent-1-yn-1-yl)phenyl)-3,6-dihydropyridin-1(2H)-yl)-2-methyl-2-(methylsulfonyl)butanamide Step 1: Synthesis of methyl 4-(4-(4-(5-hydroxypent-1-yn-1-yl)phenyl)-3,6-dihydropyridin-1(2H)-yl)-2-methyl-2-(methylsulfonyl)butanoate

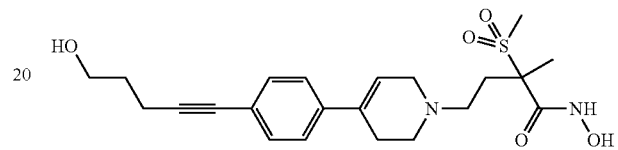

To a solution of methyl 4-(4-(4-iodophenyl)-3,6-dihydropyridin-1(2H)-yl)-2-methyl-2-(methylsulfonyl)butanoate (Intermediate 2) (2 g, 1 eq) in a mixture of THF (20 ml)/toluene (20 ml) was added with CuI (79.8 mg, 0.1 eq), Pd(PPh$_3$)$_2$Cl$_2$(295 mg, 0.1 eq), Et$_3$N (1.75 ml, 3 eq) and pent-4-yn-1-ol (705 mg, 2 eq). The mixture was stirred for 12 hr at room temperature and extracted with ethyl acetate and water. The organic layer was washed with brine, dried over anhydrous MgSO$_4$ and concentrated in vacuo. The residue was purified with column chromatography to prepare the title compound (1.5 g, 83%).

$^1$H NMR (600 MHz, CDCl$_3$-d1); δ7.33-7.32 (m, 2H), 7.28-7.27 (m, 2H), 6.05 (s, 1H), 3.82-3.79 (m, 2H), 3.75-3.72 (m, 3H), 3.69 (s, 3H), 3.05 (s, 3H), 2.70-2.62 (m, 1H), 2.53 (t, J=7.2 Hz, 3H), 2.38 (t, J=6.0 Hz, 3H), 1.78-1.64 (m, 4H), 1.64 (s, 3H).

Step 2-4: Synthesis of N-hydroxy-4-(4-(4-(5-hydroxypent-1-yn-1-yl)phenyl)-3,6-dihydropyridin-1(2H)-yl)-2-methyl-2-(methylsulfonyl)butanamide

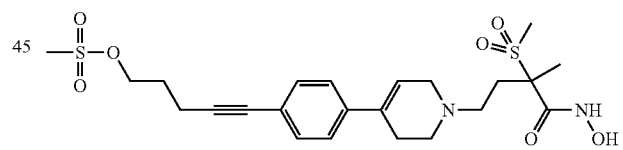

The title compound was prepared the procedures described for the synthesis of Example 1, step 2-4 (Synthesis of Hydroxamate) from methyl 4-(4-(4-(5-hydroxypent-1-yn-1-yl)phenyl)-3,6-dihydropyridin-1(2H)-yl)-2-methyl-2-(methylsulfonyl)butanoate.

$^1$H NMR (600 MHz, CD$_3$OD-d4); δ11.04 (bs, 1H), 9.13 (bs, 1H), 7.43-7.38 (m, 2H), 7.33-7.28 (m, 2H), 6.19 (s, 1H), 4.52 (bs, 1H), 3.54-3.50 (m, 2H), 3.17-3.15 (m, 2H), 3.06 (s, 3H), 2.64-2.54 (m, 2H), 2.48-2.38 (m, 4H), 1.90-1.84 (m, 2H), 1.69-1.57 (m, 4H), 1.46 (s, 3H).

MS (ESI, m/z): 435.0 [M+H]$^+$.

Example 19: Synthesis of 5-(4-(1-(4-(hydroxyamino)-3-methyl-3-(methylsulfonyl)-4-oxobutyl)-1,2,3,6-tetrahydropyridin-4-yl)phenyl)pent-4-yn-1-yl methanesulfonate Step 1: Synthesis of methyl 2-methyl-2-(methylsulfonyl)-4-(4-(4-(5-((methylsulfonyl)oxy)pent-1-yn-1-yl)phenyl)-3,6-dihydropyridin-1(2H)-yl)butanoate

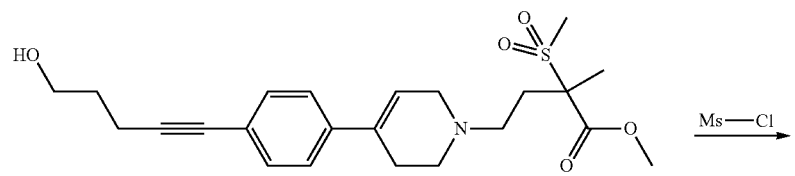

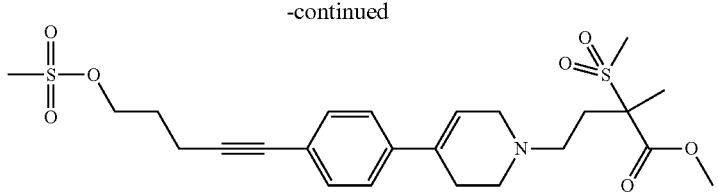

To a solution of methyl 4-(4-(4-(5-hydroxypent-1-yn-1-yl)phenyl)-3,6-dihydropyridin-1(2H)-yl)-2-methyl-2-(methylsulfonyl)butanoate (1.5 g, 1 eq) in dichloromethane (17.3 ml) was added with Et₃N (0.964 ml, 2 eq) and methanesulfonyl chloride (0.793 ml, 2 eq). The mixture was stirred for 2 hr at room temperature and extracted with dichloromethane and water. The organic layer was washed with brine, dried over anhydrous MgSO₄ and concentrated in vacuo. The residue was purified with column chromatography to prepare the title compound (0.9 g, 51%).

¹H NMR (600 MHz, CDCl₃); δ7.34-7.32 (m, 2H), 7.29-7.27 (m, 2H), 6.04 (s, 1H), 4.40 (t, J=6.0 Hz, 2H), 3.72-3.70 (m, 3H), 3.13 (s, 6H), 3.06 (s, 3H), 3.03 (s, 3H), 2.70-2.62 (m, 1H), 2.59-2.56 (m, 3H), 2.05-2.01 (m, 3H), 1.71-1.62 (m, 4H).

MS (ESI, m/z): 512.2 [M+H]⁺.

Step 2: Synthesis of 2-methyl-2-(methylsulfonyl)-4-(4-(4-(5-((methylsulfonyl)oxy)pent-1-yn-1-yl)phenyl)-3,6-dihydropyridin-1(2H)-yl)butanoic acid

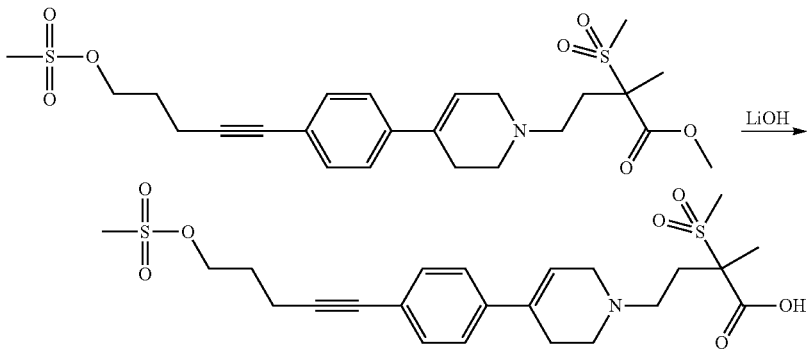

The title compound was prepared the procedures described for the synthesis of Example 1, step 2 from methyl 2-methyl-2-(methylsulfonyl)-4-(4-(4-(5-((methylsulfonyl)oxy)pent-1-yn-1-yl)phenyl)-3,6-dihydropyridin-1(2H)-yl)butanoate.

MS (ESI, m/z): 498.2 [M+H]⁺.

Step 3: Synthesis of 5-(4-(1-(3-methyl-3-(methylsulfonyl)-4-oxo-4-(((tetrahydro-2H-pyran-2-yl)oxy)amino)butyl)-1,2,3,6-tetrahydropyridin-4-yl)phenyl)pent-4-yn-1-yl methanesulfonate

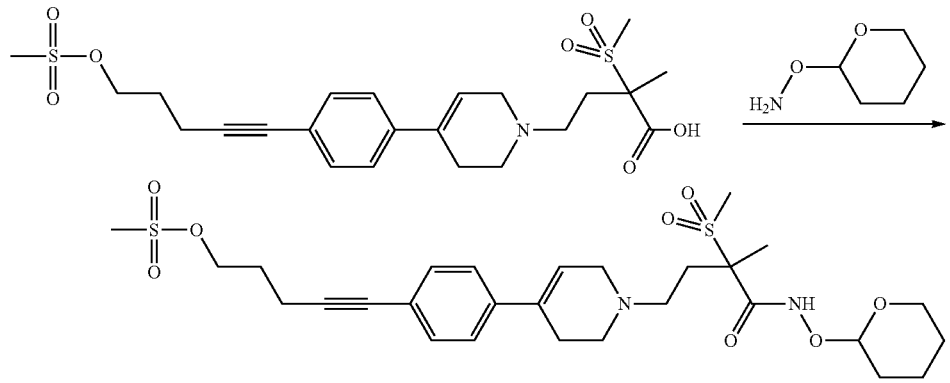

The title compound was prepared the procedures described for the synthesis of Example 1, step 3 from 2-methyl-2-(methylsulfonyl)-4-(4-(4-(5-(((methylsulfonyl)oxy)pent-1-yn-1-yl)phenyl)-3,6-dihydropyridin-1(2H)-yl)butanoic acid.

MS (ESI, m/z): 597.2 [M+H]$^+$.

Step 4: Synthesis of 5-(4-(1-(4-(hydroxyamino)-3-methyl-3-(methylsulfonyl)-4-oxobutyl)-1,2,3,6-tetrahydropyridin-4-yl)phenyl)pent-4-yn-1-yl methanesulfonate

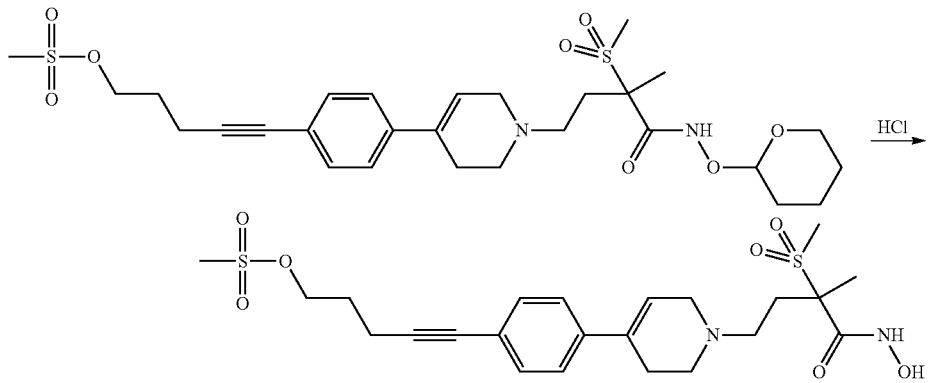

The title compound was prepared the procedures described for the synthesis of Example 1, step 4 from 5-(4-(1-(3-methyl-3-(methylsulfonyl)-4-oxo-4-(((tetrahydro-2H-pyran-2-yl)oxy)amino)butyl)-1,2,3,6-tetrahydropyridin-4-yl)phenyl)pent-4-yn-1-yl methanesulfonate.

$^1$H NMR (600 MHz, DMSO-d6); δ11.01 (bs, 1H), 9.10 (bs, 1H), 7.47-7.32 (m, 4H), 6.25 (s, 1H), 4.38-4.31 (m, 2H), 3.19 (s, 3H), 3.10-3.09 (m, 2H), 3.06 (s, 3H), 2.66-2.56 (m, 2H), 2.54-2.94 (m, 8H), 1.98-1.85 (m, 2H), 1.46 (s, 3H).

MS (ESI, m/z): 513.1 [M+H]$^+$.

Example 20: Synthesis of 4-(4-(4-(5-(dimethylamino)pent-1-yn-1-yl)phenyl)-3,6-dihydropyridin-1(2H)-yl)-N-hydroxy-2-methyl-2-(methylsulfonyl)butanamide

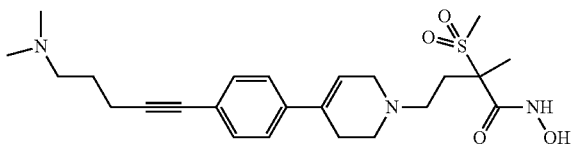 [SMILES: CN(C)CCCC#Cc1ccc(C2=CCN(CCC(C)(C(=O)NO)S(C)(=O)=O)CC2)cc1]

To a solution of 5-(4-(1-(4-(hydroxyamino)-3-methyl-3-(methylsulfonyl)-4-oxobutyl)-1,2,3,6-tetrahydropyridin-4-yl)phenyl)pent-4-yn-1-yl methanesulfonate (Example 19) (120 mg, 1 eq) in THF (3 ml) was added with dimethylamine (1M in THF, 7 ml, 30 eq). The mixture was refluxed for 4 hr and cooled room temperature, and the solvent was concentrated in vacuo. The residue was purified with column chromatography to prepare the title compound (38 mg, 35%).

$^1$H NMR (600 MHz, DMSO-d6); δ10.6 (bs, 1H), 9.2 (bs, 1H), 7.38-7.37 (m, 2H), 7.31-7.30 (m, 2H), 6.18 (s, 1H), 3.12-3.06 (m, 2H), 3.04 (s, 3H), 2.63-2.56 (m, 2H), 2.46-2.40 (m, 6H), 2.32-2.26 (m, 3H), 2.11 (s, 6H), 1.82-1.79 (m, 1H), 1.66-1.61 (m, 2H), 1.44 (s, 3H).

MS (ESI, m/z): 462.2 [M+H]$^+$.

Example 21: Synthesis of 4-(4-(4-(5-aminopent-1-yn-1-yl)phenyl)-3,6-dihydropyridin-1(2H)-yl)-N-hydroxy-2-methyl-2-(methylsulfonyl)butanamide

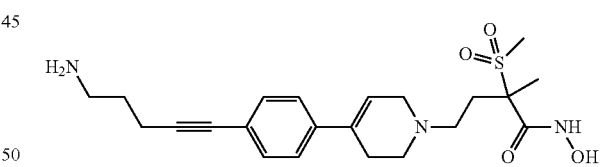

Step 1: Synthesis of 4-(4-(4-(5-aminopent-1-yn-1-yl)phenyl)-3,6-dihydropyridin-1(2H)-yl)-2-methyl-2-(methylsulfonyl)-N-((tetrahydro-2H-pyran-2-yl)oxy)butanamide

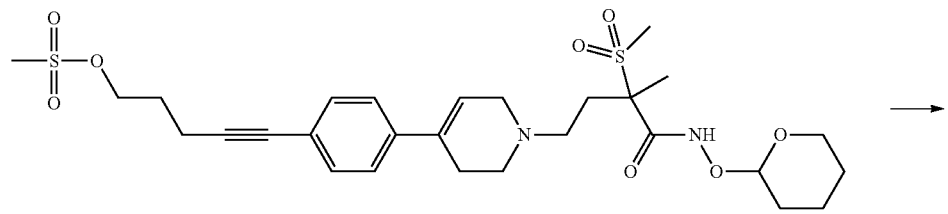

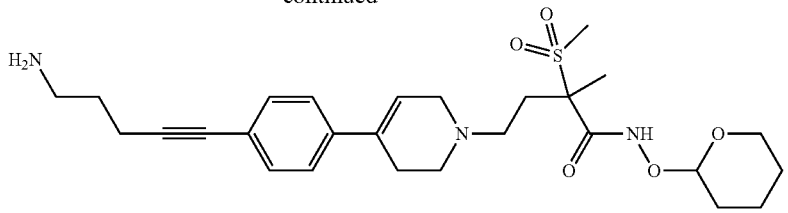

To a solution of 5-(4-(1-(3-methyl-3-(methylsulfonyl)-4-oxo-4-(((tetrahydro-2H-pyran-2-yl)oxy)amino)butyl)-1,2,3,6-tetrahydropyridin-4-yl)phenyl)pent-4-yn-1-yl methanesulfonate (Example 19, step 3) (200 mg, 1 eq) in 1,4-dioxane (0.67 ml) was added with ammonia (0.5M in 1,4-dioxane, 6.7 ml, 10 eq). The mixture was refluxed for 12 hr and cooled room temperature, and the solvent was concentrated in vacuo. The residue was purified with column chromatography to prepare the title compound (80 mg, 46%).

MS (ESI, m/z): 518.3 [M+H]+.

Step 2: Synthesis of 4-(4-(4-(5-aminopent-1-yn-1-yl)phenyl)-3,6-dihydropyridin-1(2H)-yl)-N-hydroxy-2-methyl-2-(methylsulfonyl)butanamide The title compound was prepared the procedures described for the synthesis of Example 1, step 4 from 4-(4-(4-(5-aminopent-1-yn-1-yl)phenyl)-3,6-dihydropyridin-1(2H)-yl)-2-methyl-2-(methylsulfonyl)-N-((tetrahydro-2H-pyran-2-yl)oxy)butanamide.

$^1$H NMR (600 MHz, DMSO-d6); δ7.38-7.36 (m, 2H), 7.32-7.31 (m, 2H), 6.18 (s, 1H), 3.09-3.06 (m, 2H), 3.04 (s, 3H), 2.82 (t, J=7.2 Hz, 2H), 2.62-2.56 (m, 3H), 2.45-2.42 (m, 6H), 2.38-2.32 (m, 1H), 1.98-1.95 (m, 1H), 1.74-1.71 (m, 3H), 1.44 (s, 3H).

MS (ESI, m/z): 434.2 [M+H]+.

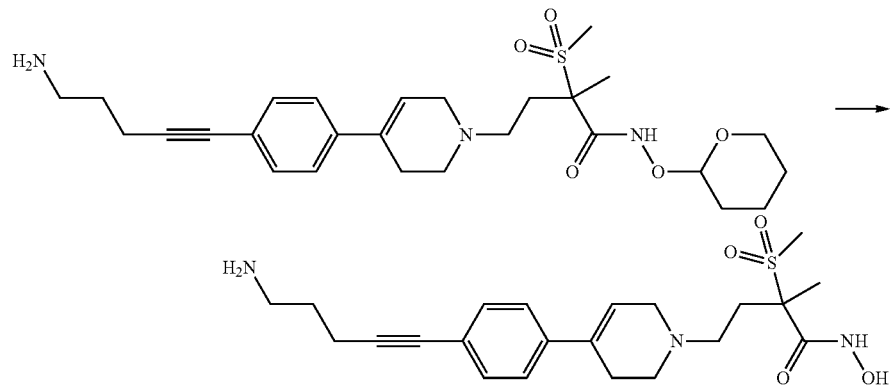

Examples 22-25

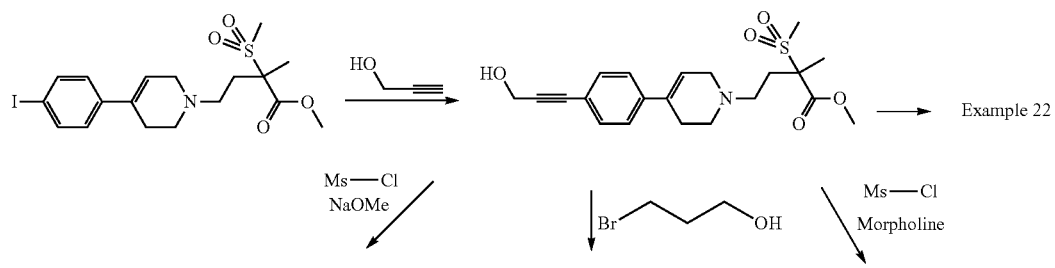

Example 22

-continued

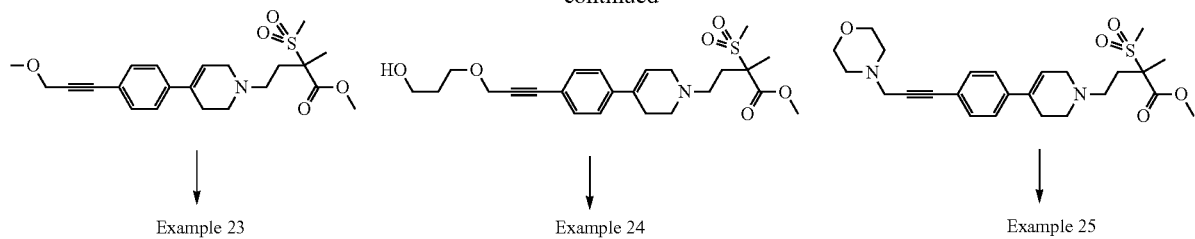

Example 23　　　　　　Example 24　　　　　　Example 25

Example 22: Synthesis of N-hydroxy-4-(4-(4-(3-hydroxyprop-1-yn-1-yl)phenyl)-3,6-dihydropyridin-1(2H)-yl)-2-methyl-2-(methylsulfonyl)butanamide

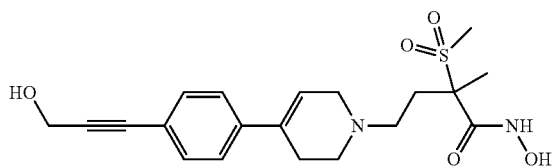 [SMILES: CC(CCN1CC=C(c2ccc(C#CCO)cc2)CC1)(C(=O)NO)S(C)(=O)=O]

Step 1: Synthesis of methyl 4-(4-(4-(3-hydroxy-prop-1-yn-1-yl)phenyl)-3,6-dihydropyridin-1(2H)-yl)-2-methyl-2-(methylsulfonyl)butanoate The title compound was prepared the procedures described for the synthesis of Example 1, step 1 using prop-2-yn-1-ol.
$^1$H NMR (600 MHz, CDCl$_3$-d1) δ; 7.38-7.36 (m, 2H), 7.31-7.29 (m, 2H), 6.05 (s, 1H), 4.49 (s, 2H), 3.80-3.70 (m, 4H), 3.48-3.30 (m, 2H), 3.07-3.02 (m, 5H), 2.68-2.56 (m, 4H), 1.70-1.64 (m, 4H).
MS (ESI, m/z): 406.1[M+H]$^+$.

Step 2-4: Synthesis of N-hydroxy-4-(4-(4-(3-hydroxyprop-1-yn-1-yl)phenyl)-3,6-dihydropyridin-1(2H)-yl)-2-methyl-2-(methylsulfonyl)butanamide The title compound was prepared the procedures described for the synthesis of Example 1, step 2-4 (Synthesis of Hydroxamate) from methyl 4-(4-(4-(3-hydroxyprop-1-yn-1-yl)phenyl)-3,6-dihydropyridin-1(2H)-yl)-2-methyl-2-(methylsulfonyl)butanoate.
$^1$H NMR (600 MHz, DMSO-d6); δ11.00 (bs, 1H), 9.12 (bs, 1H), 7.40-7.35 (m, 4H), 6.16 (s, 1H), 5.31 (s, 1H), 4.37 (s, 2H), 3.40-3.34 (m, 2H), 3.07 (s, 3H), 2.95-2.92 (m, 2H), 2.86-2.85 (m, 2H), 2.64-2.56 (m, 4H), 2.14-2.10 (m, 2H), 1.59 (s, 3H).
MS (ESI, m/z): 407.0 [M+H]$^+$.

Example 23: Synthesis of N-hydroxy-4-(4-(4-(3-methoxyprop-1-yn-1-yl)phenyl)-3,6-dihydropyridin-1(2H)-yl)-2-methyl-2-(methylsulfonyl)butanamide

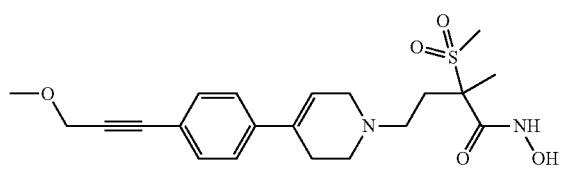 [SMILES: COCC#Cc1ccc(C2=CCN(CCC(C)(C(=O)NO)S(C)(=O)=O)CC2)cc1]

Step 1: Synthesis of methyl 4-(4-(4-(3-methoxy-prop-1-yn-1-yl)phenyl)-3,6-dihydropyridin-1(2H)-yl)-2-methyl-2-(methylsulfonyl)butanoate To a solution of methyl 4-(4-(4-(3-hydroxyprop-1-yn-1-yl)phenyl)-3,6-dihydropyridin-1(2H)-yl)-2-methyl-2-(methylsulfonyl)butanoate (Example 22, Step 1) (500 mg, 1 eq) in dichloromethane (10 ml) was added with Et$_3$N (0.34 ml, 2 eq) and methanesulfonyl chloride (0.19 ml, 2 eq). The mixture was and stirred for 2 hr at room temperature. Sodium methoxide (25% solution in MeOH, 1.06 g, 4 eq) was added and stirred for 3 hr at 60° C. The mixture was cooled down to room temperature, extracted with dichloromethane and water. The organic layer was washed with brine, dried over anhydrous MgSO$_4$ and concentrated in vacuo. The residue was purified with column chromatography to prepare the title compound (250 mg, 48%).
$^1$H NMR (600 MHz, CDCl$_3$-d1); δ7.42-7.41 (m, 2H), 7.32-7.30 (m, 2H), 6.02 (s, 1H), 4.31 (s, 2H), 3.90-3.79 (m, 3H), 3.48-3.42 (m, 4H), 3.14-3.08 (m, 5H), 2.70-2.62 (m, 3H), 1.78-1.68 (m, 3H), 1.64-1.52 (m, 4H).
MS (ESI, m/z): 420.1 [M+H]$^+$.

Step 2: Synthesis of N-hydroxy-4-(4-(4-(3-methoxyprop-1-yn-1-yl)phenyl)-3,6-dihydropyridin-1(2H)-yl)-2-methyl-2-(methylsulfonyl)butanamide The title compound was prepared the procedures described for the synthesis of Example 1, step 2-4 (Synthesis of Hydroxamate) from methyl 4-(4-(4-(3-methoxyprop-1-yn-1-yl)phenyl)-3,6-dihydropyridin-1(2H)-yl)-2-methyl-2-(methylsulfonyl)butanoate
$^1$H NMR (600 MHz, DMSO-d6); δ10.99 (bs, 1H), 9.10 (bs, 1H), 7.42-7.38 (m, 4H), 6.21 (s, 1H), 4.29 (s, 2H), 3.28-3.24 (m, 3H), 3.10-3.04 (m, 5H), 2.62-2.54 (m, 2H), 2.45-2.29 (m, 4H), 1.41 (s, 3H), 1.22-1.20 (m, 2H).
MS (ESI, m/z): 421.1 [M+H]$^+$.

Example 24: Synthesis of N-hydroxy-4-(4-(4-(3-(3-hydroxypropoxy)prop-1-yn-1-yl)phenyl)-3,6-dihydropyridin-1(2H)-yl)-2-methyl-2-(methylsulfonyl)butanamide

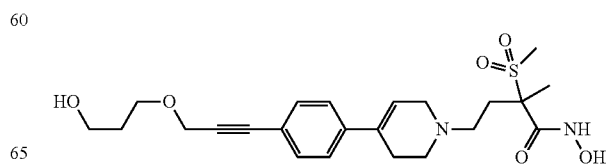

Step 1: Synthesis of methyl 4-(4-(4-(3-(3-hydroxy-propoxy)prop-1-yn-1-yl)phenyl)-3,6-dihydropyridin-1(2H)-yl)-2-methyl-2-(methylsulfonyl)butanoate To a solution of methyl 4-(4-(4-(3-hydroxyprop-1-yn-1-yl)phenyl)-3,6-dihydropyridin-1(2H)-yl)-2-methyl-2-(methylsulfonyl)butanoate (Example 22, Step 1) (280 mg, 1 eq) in DMF (15 ml) was added with NaH (47 mg, 1.7 eq, 60 wt %) and 3-bromopropan-1-ol (125 mg, 1.3 eq). The mixture was stirred for 4 hr at room temperature and extracted with ethyl acetate and water. The organic layer was dried over anhydrous MgSO₄ and concentrated in vacuo. The residue was purified with column chromatography to prepare the title compound (130 g, 51%).
MS (ESI, m/z): 464.1 [M+H]⁺.

Step 2: Synthesis of N-hydroxy-4-(4-(4-(3-(3-hydroxypropoxy)prop-1-yn-1-yl)phenyl)-3,6-dihydropyridin-1(2H)-yl)-2-methyl-2-(methylsulfonyl)butanamide The title compound was prepared the procedures described for the synthesis of Example 1, step 2-4 (Synthesis of Hydroxamate) from methyl 4-(4-(4-(3-(3-hydroxypropoxy)prop-1-yn-1-yl)phenyl)-3,6-dihydropyridin-1(2H)-yl)-2-methyl-2-(methylsulfonyl)butanoate.
¹H NMR (600 MHz, DMSO-d6); δ11.03 (bs, 1H), 9.13 (bs, 1H), 7.45-7.39 (m, 4H), 6.23 (s, 1H), 3.59-3.57 (m, 2H), 3.44-3.41 (m, 2H), 3.18-3.09 (m, 2H), 3.06 (s, 3H), 2.65-2.57 (m, 2H), 2.47-2.38 (m, 4H), 1.70-1.62 (m, 2H), 1.44 (s, 3H), 1.42-1.35 (m, 2H).
MS (ESI, m/z): 465.1 [M+H]⁺.

Example 25: Synthesis of N-hydroxy-2-methyl-2-(methylsulfonyl)-4-(4-(4-(3-morpholinoprop-1-yn-1-yl)phenyl)-3,6-dihydropyridin-1(2H)-yl)butanamide

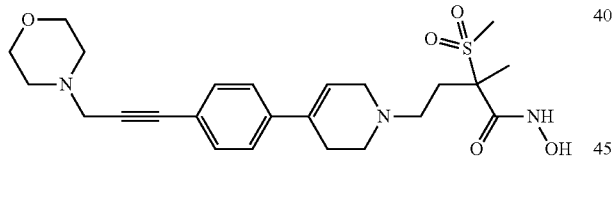

Step 1: Synthesis of methyl 2-methyl-2-(methylsulfonyl)-4-(4-(4-(3-morpholinoprop-1-yn-1-yl)phenyl)-3,6-dihydropyridin-1(2H)-yl)butanoate To a solution of methyl 4-(4-(4-(3-hydroxyprop-1-yn-1-yl)phenyl)-3,6-dihydropyridin-1(2H)-yl)-2-methyl-2-(methylsulfonyl)butanoate (Example 22, Step 1) (500 mg, 1 eq) in dichloromethane (10 ml) was added with Et₃N (0.34 ml, 2 eq) and methanesulfonyl chloride (0.19 ml, 2 eq), and the mixture was stirred for 2 hr at room temperature. Morpholine (0.22 ml, 2 eq) was added and stirred for 3 hr at 60° C. The mixture was cooled room temperature and extracted with dichloromethane and water. The organic layer was washed with brine, dried over anhydrous MgSO₄ and concentrated in vacuo. The residue was purified with column chromatography to prepare the title compound (450 mg, 77%).
¹H NMR (600 MHz, CDCl₃-d1); δ7.38-7.36 (m, 2H), 7.31-7.29 (m, 2H), 6.06 (s, 1H), 4.49 (s, 2H), 3.78-3.74 (m, 6H), 3.70-3.64 (m, 2H), 3.54-3.44 (m, 2H), 3.22-3.18 (m, 2H), 3.05 (s, 3H), 2.78 (s, 3H), 2.72-2.62 (m, 6H), 2.58-2.48 (m, 2H), 1.72-1.62 (m, 4H).
MS (ESI, m/z): 475.2 [M+H]⁺.

Step 2: Synthesis of N-hydroxy-2-methyl-2-(methylsulfonyl)-4-(4-(4-(3-morpholinoprop-1-yn-1-yl)phenyl)-3,6-dihydropyridin-1(2H)-yl)butanamide The title compound was prepared the procedures described for the synthesis of Example 1, step 2-4 (Synthesis of Hydroxamate) from methyl 2-methyl-2-(methylsulfonyl)-4-(4-(4-(3-morpholinoprop-1-yn-1-yl)phenyl)-3,6-dihydropyridin-1(2H)-yl)butanoate.
¹H NMR (600 MHz, DMSO-d6); δ11.00 (bs, 1H), 9.10 (bs, 1H), 7.41-7.39 (m, 2H), 7.37-7.35 (m, 2H), 6.19 (s, 1H), 3.62-3.56 (m, 4H), 3.48 (s, 2H), 3.14-3.07 (m, 2H), 3.06 (s, 3H), 2.64-2.52 (m, 4H), 2.46-2.38 (m, 5H), 2.32-2.26 (m, 1H), 2.00-1.96 (m, 1H), 1.82-1.76 (m, 1H), 1.44 (s, 3H).
MS (ESI, m/z): 476.2 [M+H]⁺.

Example 26: Synthesis of 3-(4-(1-(4-(hydroxyamino)-3-methyl-3-(methylsulfonyl)-4-oxobutyl)-1,2,3,6-tetrahydropyridin-4-yl)phenyl)prop-2-yn-1-yl carbamate

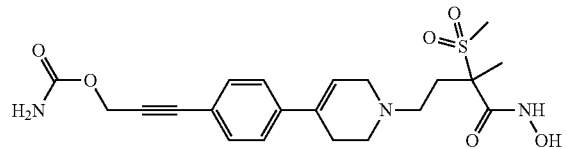

Step 1: Synthesis of 3-(4-(1-(3-methyl-3-(methylsulfonyl)-4-oxo-4-(((tetrahydro-2H-pyran-2-yl)oxy)amino)butyl)-1,2,3,6-tetrahydropyridin-4-yl)phenyl)prop-2-yn-1-yl carbamate

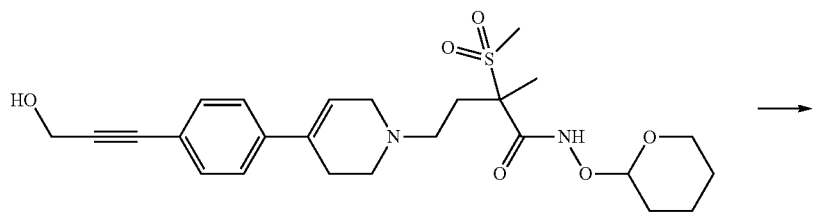

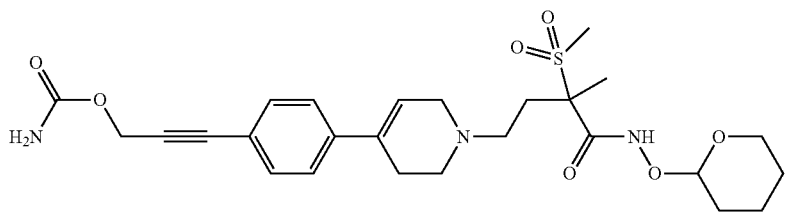

To a solution of 4-(4-(4-(3-hydroxyprop-1-yn-1-yl)phenyl)-3,6-dihydropyridin-1(2H)-yl)-2-methyl-2-(methylsulfonyl)-N-((tetrahydro-2H-pyran-2-yl)oxy)butanamide (200 mg, 1 eq) in THF (10 ml) was added with CDI (500 mg, 8 eq) and Et$_3$N (0.16 ml, 3 eq), and the mixture was stirred for 4 hr at room temperature. NH$_4$OH (0.15 ml, 10 eq) was added and stirred for 2 hr at 0° C. The mixture was extracted with ethyl acetate and water. The organic layer was dried over anhydrous MgSO$_4$ and concentrated in vacuo. The residue was purified with column chromatography to prepare the title compound (50 mg, 23%).

Step 2: Synthesis of 3-(4-(1-(4-(hydroxyamino)-3-methyl-3-(methylsulfonyl)-4-oxobutyl)-1,2,3,6-tetrahydropyridin-4-yl)phenyl)prop-2-yn-1-yl carbamate The title compound was prepared the procedures described for the synthesis of Example 1, step 4 using 3-(4-(1-(3-methyl-3-(methylsulfonyl)-4-oxo-4-(((tetrahydro-2H-pyran-2-yl)oxy)amino)butyl)-1,2,3,6-tetrahydropyridin-4-yl)phenyl)prop-2-yn-1-yl carbamate.

$^1$H NMR (600 MHz, DMSO-d6); δ11.01 (bs, 1H), 9.09 (bs, 1H), 7.44-7.37 (m, 4H), 6.22 (s, 1H), 4.80 (s, 2H), 3.10-3.88 (m, 2H), 3.04 (s, 3H), 2.65-2.53 (m, 2H), 2.47-2.43 (m, 2H), 1.97-1.80 (m, 2H), 1.44 (s, 3H).

MS (ESI, m/z): 450.1 [M+H]$^+$.

Example 27: Synthesis of 5-(4-(1-(4-(hydroxyamino)-3-methyl-3-(methylsulfonyl)-4-oxobutyl)-1,2,3,6-tetrahydropyridin-4-yl)phenyl)pent-4-yn-1-yl carbamate

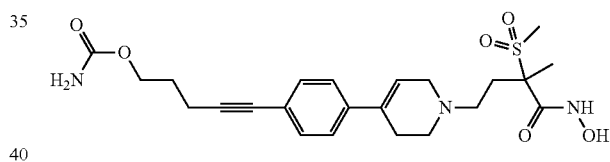

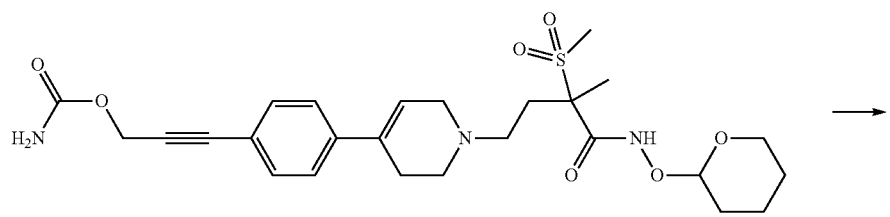

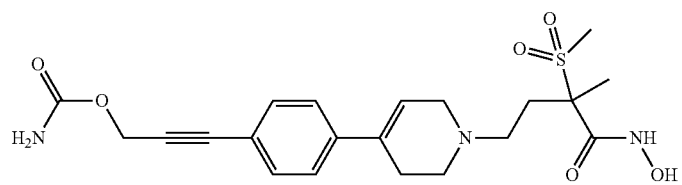 [SMILES: CC(CCN1CC=C(c2ccc(C#CCOC(N)=O)cc2)CC1)(C(=O)NO)S(C)(=O)=O]

Step 1: Synthesis of 5-(4-(1-(3-methyl-3-(methyl-sulfonyl)-4-oxo-4-(((tetrahydro-2H-pyran-2-yl)oxy)amino)butyl)-1,2,3,6-tetrahydropyridin-4-yl)phenyl)pent-4-yn-1-yl carbamate

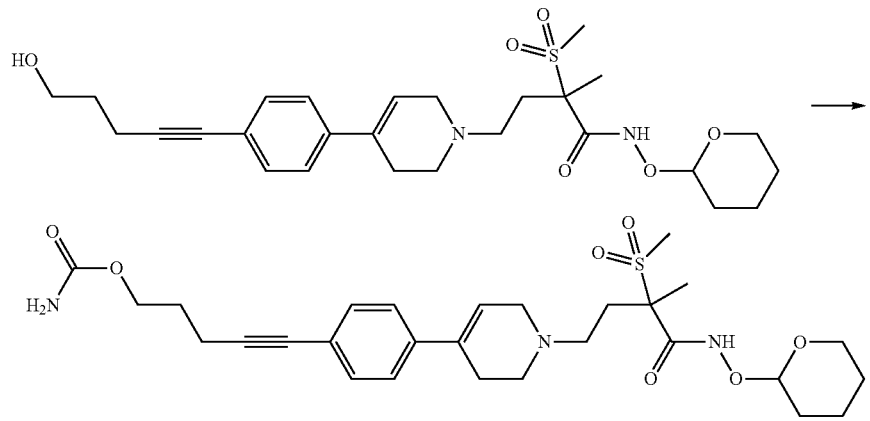

The title compound was prepared the procedures described for the synthesis of Example 26, step 1 using 4-(4-(4-(5-hydroxypent-1-yn-1-yl)phenyl)-3,6-dihydropyridin-1(2H)-yl)-2-methyl-2-(methylsulfonyl)-N-((tetrahydro-2H-pyran-2-yl)oxy)butanamide.

Step 2: Synthesis of 5-(4-(1-(4-(hydroxyamino)-3-methyl-3-(methylsulfonyl)-4-oxobutyl)-1,2,3,6-tetrahydropyridin-4-yl)phenyl)pent-4-yn-1-yl carbamate

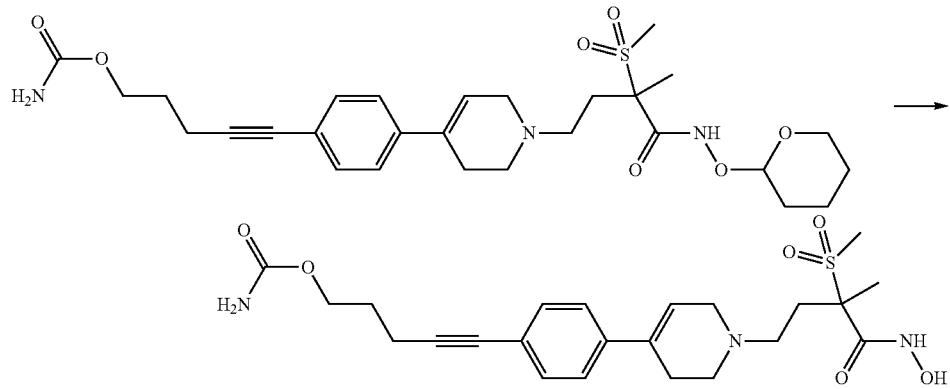

The title compound was prepared the procedures described for the synthesis of Example 1, step 4 using of 5-(4-(1-(3-methyl-3-(methylsulfonyl)-4-oxo-4-(((tetrahydro-2H-pyran-2-yl)oxy)amino)butyl)-1,2,3,6-tetrahydropyridin-4-yl)phenyl)pent-4-yn-1-yl carbamate $^1$H NMR (600 MHz, DMSO-d6); δ11.01 (bs, 1H), 9.11 (bs, 1H), 7.38-7.37 (m, 2H), 7.32-7.31 (m, 2H), 6.18 (s, 1H), 3.98-3.97 (m, 2H), 3.09-3.04 (m, 5H), 2.62-2.57 (m, 2H), 2.48-2.46 (m, 2H), 2.30-2.28 (m, 2H), 1.81-1.78 (m, 4H), 1.44 (s, 3H), 1.23-1.21 (m, 2H).

MS (ESI, m/z): 478.2 [M+H]$^+$.

Example 28: Synthesis of N-hydroxy-4-(4-(4-(5-methoxypent-1-yn-1-yl)phenyl)-3,6-dihydropyridin-1(2H)-yl)-2-methyl-2-(methylsulfonyl)butanamide

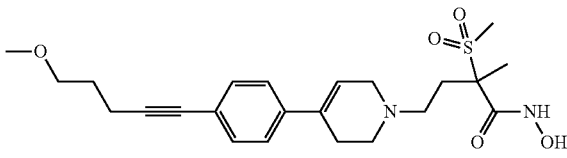 [SMILES: COCCCC#Cc1ccc(C2=CCN(CCC(C)(C(=O)NO)S(C)(=O)=O)CC2)cc1]

The title compound was prepared the procedures described for the synthesis of Example 23 from methyl 4-(4-(4-(5-hydroxypent-1-yn-1-yl)phenyl)-3,6-dihydropyridin-1(2H)-yl)-2-methyl-2-(methylsulfonyl)butanoate (Example 18, Step 1).

$^1$H NMR (600 MHz, DMSO-d6); δ11.02 (bs, 1H), 9.12 (bs, 1H), 7.41-7.38 (m, 2H), 7.34-7.32 (m, 2H), 6.19 (s, 1H), 3.75-3.41 (m, 2H), 3.25 (s, 2H), 3.17-3.10 (m, 2H), 3.06 (s, 3H), 2.67-2.54 (m, 2H), 2.45-2.28 (m, 6H), 1.78-1.72 (m, 2H), 1.46 (s, 3H).

MS (ESI, m/z): 449.2 [M+H]$^+$.

Examples 29-30

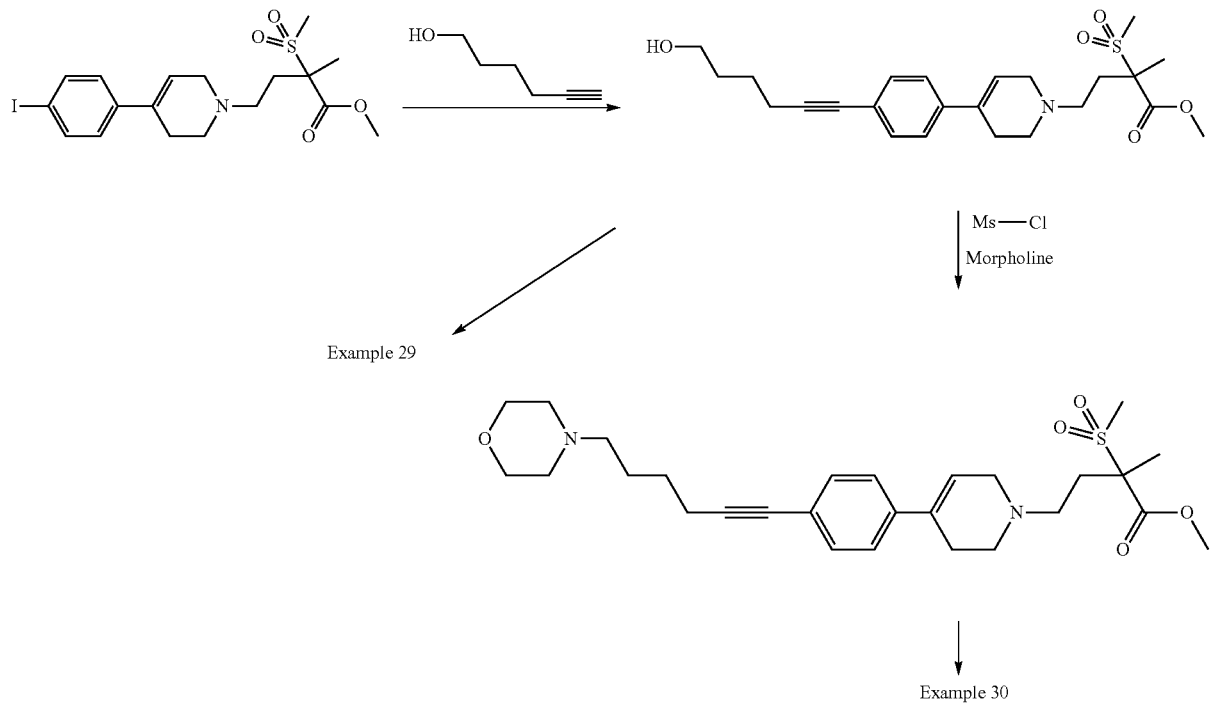

Example 29

Example 30

Example 29: Synthesis of N-hydroxy-4-(4-(4-(6-hydroxyhex-1-yn-1-yl)phenyl)-3,6-dihydropyridin-1(2H)-yl)-2-methyl-2-(methylsulfonyl)butanamide

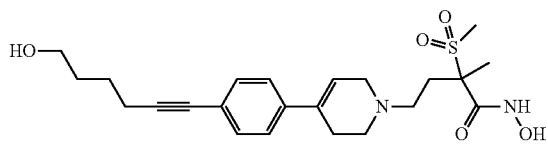 [SMILES: CC(CCN1CC=C(c2ccc(C#CCCCCO)cc2)CC1)(C(=O)NO)S(C)(=O)=O]

Step 1: Synthesis of methyl 4-(4-(4-(6-hydroxyhex-1-yn-1-yl)phenyl)-3,6-dihydropyridin-1(2H)-yl)-2-methyl-2-(methylsulfonyl)butanoate The title compound was prepared the procedures described for the synthesis of Example 1, step 1 using hex-5-yn-1-ol.

$^1$H NMR (600 MHz, CDCl$_3$-d1); δ7.33-7.31 (m, 2H), 7.28-7.26 (m, 2H), 6.05 (s, 1H), 3.72-3.62 (m, 5H), 3.18-3.10 (m, 2H), 3.04 (s, 3H), 2.72-2.58 (m, 3H), 2.52-2.40 (m, 5H), 1.78-1.65 (m, 6H), 1.63 (s, 3H).

Step 2-4: Synthesis of N-hydroxy-4-(4-(4-(6-hydroxyhex-1-yn-1-yl)phenyl)-3,6-dihydropyridin-1(2H)-yl)-2-methyl-2-(methylsulfonyl)butanamide The title compound was prepared the procedures described for the synthesis of Example 1, step 2-4 (Synthesis of Hydroxamate) from methyl 4-(4-(4-(6-hydroxyhex-1-yn-1-yl)phenyl)-3,6-dihydropyridin-1(2H)-yl)-2-methyl-2-(methylsulfonyl)butanoate.

$^1$H NMR (600 MHz, DMSO-d6); δ11.04 (bs, 1H), 9.10 (bs, 1H), 7.37-7.36 (m, 2H), 7.30-7.28 (m, 2H), 6.17 (s, 1H), 4.43-4.28 (m, 2H), 3.40-3.5 (m, 4H), 3.09-3.05 (m, 2H), 3.04 (s, 3H), 2.6-2.58 (m, 2H), 2.43-2.39 (m, 4H), 1.47 (s, 3H), 1.41-1.38 (m, 4H).

MS (ESI, m/z): 449.1 [M+H]$^+$.

Example 30: Synthesis of N-hydroxy-2-methyl-2-(methylsulfonyl)-4-(4-(4-(6-morpholinohex-1-yn-1-yl)phenyl)-3,6-dihydropyridin-1(2H)-yl)butanamide

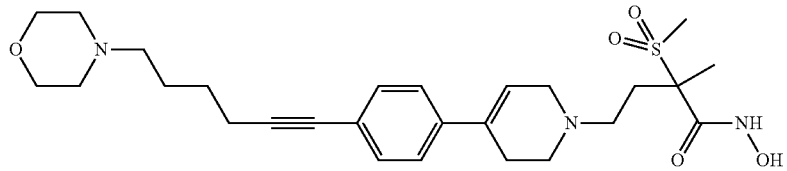 [SMILES: CC(CCN1CC=C(c2ccc(C#CCCCCN3CCOCC3)cc2)CC1)(C(=O)NO)S(C)(=O)=O]

The title compound was prepared the procedures described for the synthesis of Example 25 using methyl 4-(4-(4-(6-hydroxyhex-1-yn-1-yl)phenyl)-3,6-dihydropyridin-1(2H)-yl)-2-methyl-2-(methylsulfonyl)butanoate (Example 29, Step 1).

$^1$H NMR (600 MHz, DMSO-d6); δ11.06 (bs, 1H), 9.15 (bs, 1H), 7.43-7.41 (m, 2H), 7.35-7.33 (m, 2H), 6.22 (s, 1H), 3.62-3.56 (m, 4H), 3.18-3.10 (m, 2H), 3.08 (s, 3H), 2.72-2.58 (m, 3H), 2.48-2.40 (m, 5H), 2.40-2.28 (m, 6H), 2.05-1.98 (m, 1H), 1.82-1.70 (m, 1H), 1.62-1.56 (m, 4H), 1.48 (s, 3H).

MS (ESI, m/z): 518.3 [M+H]$^+$.

Example 31: Synthesis of 4-(4-(4-(3-(dimethylamino)prop-1-yn-1-yl)-3-fluorophenyl)-3,6-dihydropyridin-1(2H)-yl)-N-hydroxy-2-methyl-2-(methylsulfonyl)butanamide

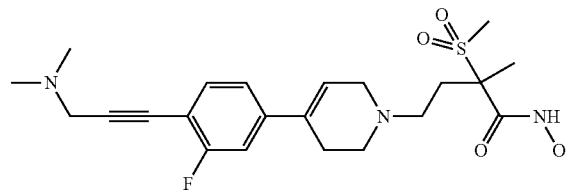

Step 1: Synthesis of 3-(4-bromo-2-fluorophenyl)-N,N-dimethylprop-2-yn-1-amine

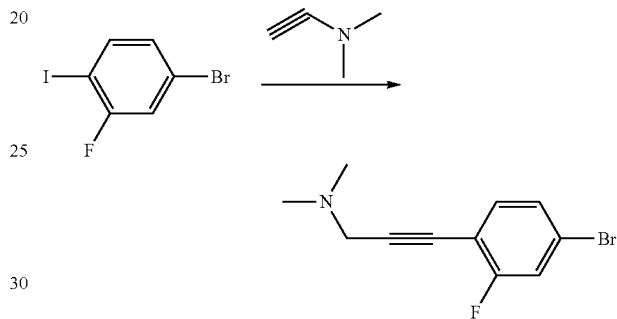

To a solution of 4-bromo-2-fluoro-1-iodobenzene (3 g, 1 eq) in a mixture of THF (10 ml)/toluene (10 ml) was added with CuI (0.19 g, 0.1 eq), Pd(PPh$_3$)$_2$Cl$_2$(0.7 g, 0.1 eq), Et$_3$N (4.2 ml, 3 eq) and N,N-dimethylprop-2-yn-1-amine (1.61 ml, 1.5 eq). The mixture was stirred for 12 hr at room temperature and extracted with ethyl acetate and water. The organic layer was washed with brine, dried over anhydrous MgSO$_4$ and concentrated in vacuo. The residue was purified with column chromatography to prepare the title compound (1.87 g, 73%).

$^1$H NMR (600 MHz, CDCl$_3$-d1); δ7.29-7.22 (m, 3H), 3.49 (s, 2H), 2.36 (s, 6H).

Step 2: Synthesis of tert-butyl 4-(4-(3-(dimethylamino)prop-1-yn-1-yl)-3-fluorophenyl)-3,6-dihydropyridine-1(2H)-carboxylate

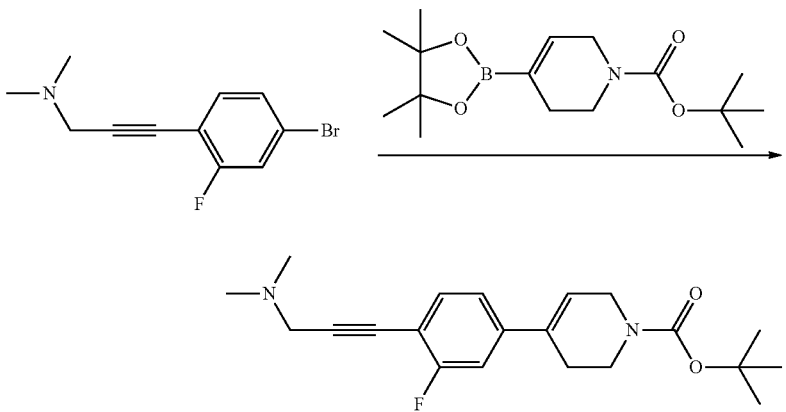

To a solution of 3-(4-bromo-2-fluorophenyl)-N,N-dimethylprop-2-yn-1-amine (1.87 g, 1 eq) in a mixture of 1,4-dioxane (16 ml)/water (4 ml) was added with Pd(PPh$_3$)$_2$Cl$_2$(0.51 g, 0.1 eq), K$_2$CO$_3$(3.03 g, 3 eq), tert-butyl 4-(4,4,5,5-tetramethyl-1,3,2-dioxaborolan-2-yl)-3,6-dihydropyridine-1(2H)-carboxylate (2.71 g, 1.2 eq). The mixture was stirred for 2 hr at 110° C. and cooled down to room temperature, and extracted with ethyl acetate and water. The organic layer was washed with brine, dried over anhydrous MgSO$_4$ and concentrated in vacuo. The residue was purified with column chromatography to prepare the title compound (2 g, 76%).

$^1$H NMR (600 MHz, CDCl$_3$-d1); δ7.36 (t, J=7.2 Hz, 1H), 7.25-7.07 (m, 2H), 6.07 (s, 1H), 4.11-4.07 (m, 2H), 3.64-3.59 (m, 2H), 3.47 (s, 2H), 2.49-2.45 (m, 2H), 2.36 (s, 6H), 1.58 (s, 9H).

MS (ESI, m/z): 359.2 [M+H]$^+$.

Step 3: Synthesis of 3-(2-fluoro-4-(1,2,3,6-tetrahydropyridin-4-yl)phenyl)-N,N-dimethylprop-2-yn-1-amine hydrochloride

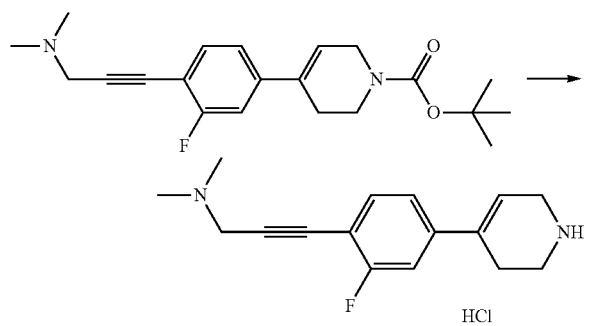

To a solution of tert-butyl 4-(4-(3-(dimethylamino)prop-1-yn-1-yl)-3-fluorophenyl)-3,6-dihydropyridine-1(2H)-carboxylate (2 g, 1 eq) in MeOH (16 ml) was added with acetyl chloride (3.97 ml, 10 eq). The mixture was stirred for 3 hr at 60° C. and cooled down to room temperature, and the solvent was concentrated in vacuo to prepare the title compound (1.6 g, 97%).

$^1$H NMR (600 MHz, DMSO-d6); δ11.52 (bs, 1H), 9.56 (bs, 2H), 7.61 (t, J=8.4 Hz, 1H), 7.48, (dd, J=11.4 Hz, 1.8 Hz, 1H), 7.38 (dd, J=8.4 Hz, 1.8 Hz, 1H), 6.39 (bs, 1H), 4.36 (s, 2H), 3.72-3.70 (m, 2H), 3.27-3.23 (m, 2H), 2.78 (s, 6H), 2.68-2.64 (m, 2H).

MS (ESI, m/z): 259.2 [M+H]$^+$.

Step 4: Synthesis of methyl 4-(4-(4-(3-(dimethylamino)prop-1-yn-1-yl)-3-fluorophenyl)-3,6-dihydropyridin-1(2H)-yl)-2-methyl-2-(methylsulfonyl)butanoate

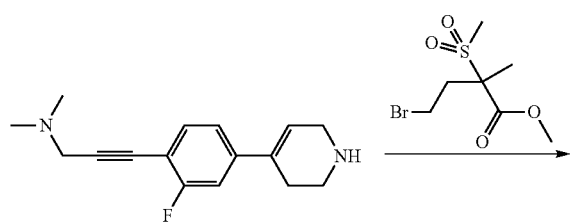

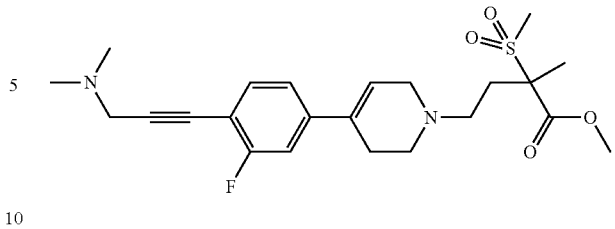

To a solution of 3-(2-fluoro-4-(1,2,3,6-tetrahydropyridin-4-yl)phenyl)-N,N-dimethylprop-2-yn-1-amine hydrochloride (600 mg, 1 eq) in DMF (10 ml) was added with N,N-diisopropylethylamine (1.42 ml, 4 eq) and methyl 4-bromo-2-methyl-2-(methylsulfonyl)butanoate (Intermediate 1) (778 mg, 1.4 eq). The mixture was stirred for 12 hr at 60° C., cooled down to room temperature, and extracted with ethyl acetate and water. The organic layer was washed with brine, dried over anhydrous MgSO$_4$ and concentrated in vacuo. The residue was purified with column chromatography to prepare the title compound (280 mg, 28%).

$^1$H NMR (600 MHz, CDCl$_3$-d1); δ 7.35 (t, J=8.4 Hz, 1H), 7.10-7.05 (m, 2H), 6.11 (bs, 1H), 3.66 (s, 3H), 3.54 (s, 2H), 3.23-3.18 (m, 1H), 3.04 (s, 3H), 3.03-3.00 (m, 1H), 2.79-2.75 (1H), 2.67-2.60 (m, 2H), 2.58-2.54 (m, 2H), 2.46-2.42 (m, 2H), 2.36 (s, 6H), 2.00-1.97 (m, 1H), 1.62 (s, 3H).

MS (ESI, m/z): 451.2 [M+H]$^+$.

Step 5: Synthesis of 4-(4-(4-(3-(dimethylamino)prop-1-yn-1-yl)-3-fluorophenyl)-3,6-dihydropyridin-1(2H)-yl)-2-methyl-2-(methylsulfonyl)butanoic acid

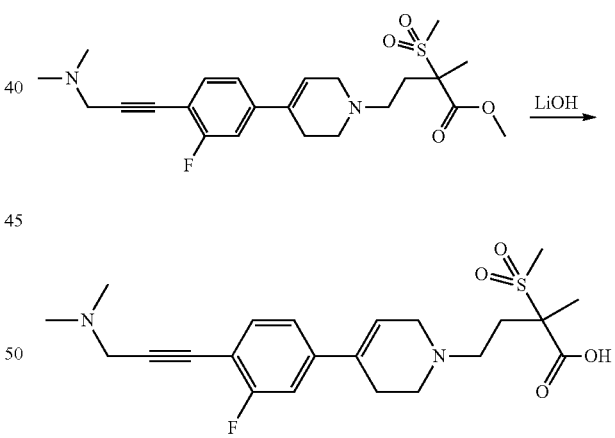

To a solution of methyl 4-(4-(4-(3-(dimethylamino)prop-1-yn-1-yl)-3-fluorophenyl)-3,6-dihydropyridin-1(2H)-yl)-2-methyl-2-(methylsulfonyl)butanoate (230 mg, 1 eq) in a mixture of THF (8 ml)/MeOH (2 ml) was added with 2N—LiOH (0.77 ml, 3 eq) solution, and the mixture was stirred for 2 hr at room temperature. The solvent was removed under reduced pressure. The residue was diluted with water (10 ml) and adjusted the pH to 4.0. The precipitated solid was filtered off to prepare the title compound (200 mg, 90%), which was used for next step without further purification.

Step 6: Synthesis of 4-(4-(4-(3-(dimethylamino)prop-1-yn-1-yl)-3-fluorophenyl)-3,6-dihydropyridin-1(2H)-yl)-2-methyl-2-(methylsulfonyl)-N-((tetrahydro-2H-pyran-2-yl)oxy)butanamide

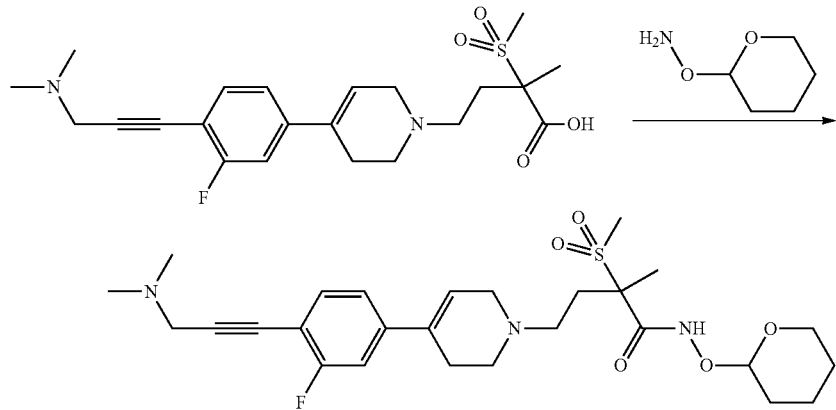

To a solution of 4-(4-(4-(3-(dimethylamino)prop-1-yn-1-yl)-3-fluorophenyl)-3,6-dihydropyridin-1(2H)-yl)-2-methyl-2-(methylsulfonyl)butanoic acid (200 mg, 1 eq) in DMF (10 ml) was added with HATU (244 mg, 1.4 eq), HOBT (98 mg, 1.4 eq), Et$_3$N (0.19 ml, 3 eq) and O-(tetrahydro-2H-pyran-2-yl)hydroxylamine hydrochloride (141 mg, 2 eq). The mixture was stirred for 1 hr at room temperature and extracted with ethyl acetate and water. The organic layer was washed with brine, dried over anhydrous MgSO$_4$ and concentrated in vacuo. The residue was purified with column chromatography to prepare the title compound (166 mg, 68%).

MS (ESI, m/z): 536.2 [M+H]$^+$.

Step 7: 4-(4-(4-(3-(dimethylamino)prop-1-yn-1-yl)-3-fluorophenyl)-3,6-dihydropyridin-1(2H)-yl)-N-hydroxy-2-methyl-2-(methylsulfonyl)butanamide To a solution of 4-(4-(4-(3-(dimethylamino)prop-1-yn-1-yl)-3-fluorophenyl)-3,6-dihydropyridin-1(2H)-yl)-2-methyl-2-(methylsulfonyl)-N-((tetrahydro-2H-pyran-2-yl)oxy)butanamide (160 mg, 1 eq) in MeOH (6 ml) was added with HCl solution in MeOH (1.25N, 0.72 ml, 3 eq), and the mixture was stirred for 2 hr at room temperature. The solvent was removed under reduced pressure. The residue was diluted with water (6 ml) and adjusted the pH to 7.0. The water was concentrated and the resulting residue was purified with column chromatography to prepare the title compound (89 mg, 57%).

$^1$H NMR (600 MHz, DMSO-d6); δ 10.98 (bs, 1H), 9.11 (bs, 1H), 7.44-7.41 (m, 1H), 7.33-7.71 (m, 1H), 7.26-7.25 (m, 1H), 6.30 (s, 1H), 3.48 (s, 2H), 3.13-3.06 (m, 2H), 3.04 (s, 3H), 2.64-2.61 (m, 1H), 2.59-2.55 (m, 1H), 2.47-2.38 (m, 4H), 2.33-2.29 (m, 1H), 2.22 (s, 6H), 1.84-1.79 (m, 1H), 1.44 (s, 3H).

MS (ESI, m/z): 452.2 [M+H]$^+$.

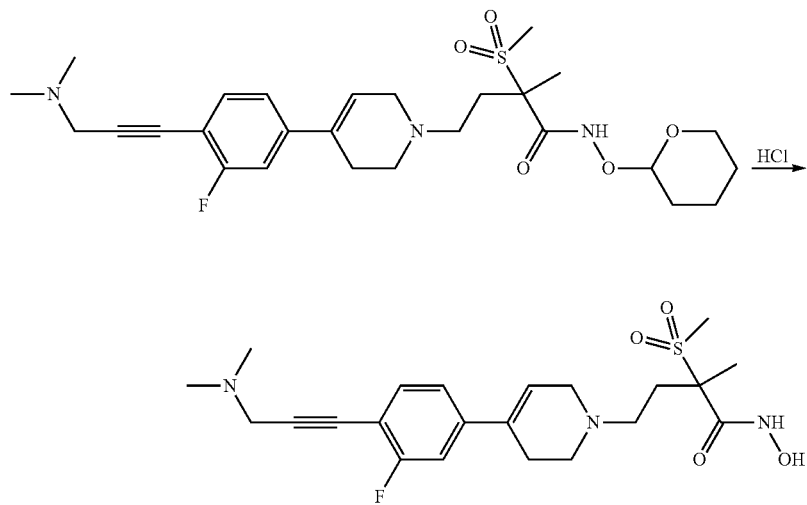

Example 32: Synthesis of 4-(4-(4-(3-(dimethyl-amino)prop-1-yn-1-yl)-3,5-difluorophenyl)-3,6-dihydropyridin-1(2H)-yl)-N-hydroxy-2-methyl-2-(methylsulfonyl)butanamide

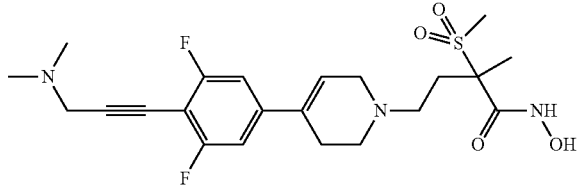 [SMILES: CN(C)CC#Cc1c(F)cc(C2=CCN(CCC(C)(C(=O)NO)S(C)(=O)=O)CC2)cc1F]

The title compound was prepared the procedures described for the synthesis of Example 31 using 5-bromo-1,3-difluoro-2-iodobenzene as a starting material.

MS (ESI, m/z): 470.2 [M+H]$^+$.

Example 33: Synthesis of 4-(4-(4-(3-(dimethyl-amino)prop-1-yn-1-yl)-2-fluorophenyl)-3,6-dihydropyridin-1(2H)-yl)-N-hydroxy-2-methyl-2-(methylsulfonyl)butanamide

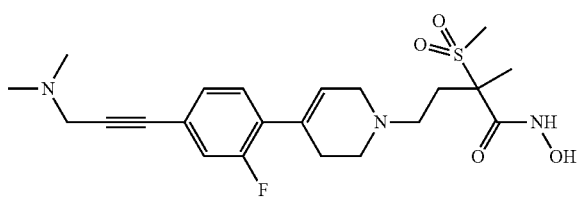 [SMILES: CN(C)CC#Cc1ccc(C2=CCN(CCC(C)(C(=O)NO)S(C)(=O)=O)CC2)c(F)c1]

The title compound was prepared the procedures described for the synthesis of Example 31 using 1-bromo-2-fluoro-4-iodobenzene as a starting material.

MS (ESI, m/z): 452.2 [M+H]$^+$.

Example 34: Synthesis of N-hydroxy-2-methyl-2-(methylsulfonyl)-4-(4-(4-(thiophen-2-ylethynyl)phenyl)-3,6-dihydropyridin-1(2H)-yl)butanamide

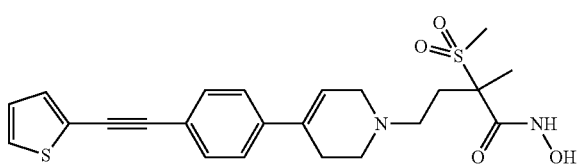 [SMILES: CC(CCN1CC=C(c2ccc(C#Cc3cccs3)cc2)CC1)(C(=O)NO)S(C)(=O)=O]

Step 1: Synthesis of 2-methyl-2-(methylsulfonyl)-N-(tetrahydro-2H-pyran-2-yl)oxy)-4-(4-(4-(thiophen-2-ylethynyl)phenyl)-3,6-dihydropyridin-1(2H)-yl)butanamide To a solution of 4-(4-(4-iodophenyl)-3,6-dihydropyridin-1(2H)-yl)-2-methyl-2-(methylsulfonyl)-N-((tetrahydro-2H-pyran-2-yl)oxy)butanamide (Intermediate 3) (220 mg, 1 eq) in THF (4 ml)/toluene (4 ml) was added with CuI (7.5 mg, 0.1 eq), Pd(PPh$_3$)$_2$Cl$_2$ (27.4 mg, 0.1 eq), Et$_3$N (0.165 ml, 3 eq) and 2-ethynylthiophene (64 mg, 1.5 eq). The mixture was stirred for 12 hr at room temperature, and extracted with ethyl acetate and water. The organic layer was washed with brine, dried over anhydrous MgSO$_4$ and concentrated in vacuo. The residue was purified with column chromatography to prepare the title compound (60 mg, 28%)

$^1$H NMR (600 MHz, CDCl$_3$-d1); δ 7.67-7.64 (m, 1H), 7.45-7.43 (m, 2H), 7.35-7.34 (m, 2H), 7.28-7.26 (m, 1H), 7.01-6.99 (m, 1H), 6.12 (s, 1H), 4.92-4.90 (m, 1H), 3.43-3.29 (m, 4H), 3.11 (s, 3H), 2.90-2.83 (m, 4H), 2.72-2.65 (m, 4H), 1.80-1.57 (m, 7H), 1.52-1.45 (s, 2H).).

MS (ESI, m/z): 543.2 [M+H]$^+$.

Step 2: Synthesis of N-hydroxy-2-methyl-2-(methylsulfonyl)-4-(4-(4-(thiophen-2-ylethynyl)phenyl)-3,6-dihydropyridin-1(2H)-yl)butanamide To a solution of 2-methyl-2-(methylsulfonyl)-N-((tetrahydro-2H-pyran-2-yl)oxy)-4-(4-(4-(thiophen-2-ylethynyl)phenyl)-3,6-dihydropyridin-1(2H)-yl)butanamide (60 mg, 1 eq) in MeOH (2 ml) was added with HCl solution in MeOH (1.25N, 0.27 ml, 3 eq), and the mixture was stirred for 2 hr at room temperature. The solvent was removed under reduced pressure. The residue was diluted with water (4 ml) and adjusted the pH to 7.0. The water was concentrated and the resulting residue was purified with column chromatography to prepare the title compound (7.7 mg, 15%).

$^1$H NMR (600 MHz, DMSO-d6); δ11.00 (bs, 1H), 9.08 (bs, 1H), 7.65-7.64 (m, 1H), 7.48-7.45 (m, 4H), 7.40-7.39 (m, 1H), 7.11-7.10 (m, 1H), 6.25 (s, 1H), 3.11-3.06 (m, 2H), 3.04 (s, 3H), 2.63-2.58 (m, 2H), 2.46-2.31 (m, 2H), 2.00-1.80 (m, 2H), 1.45 (s, 3H), 1.23-1.20 (m, 2H).

MS (ESI, m/z): 454.2 [M+H]$^+$.

Examples 35-37

The terminal acetylenes listed in the following table were used to prepare compounds of Examples 35-37 in the same manner as Example 34.

| Example | Structure (Name) | Terminal acetylene |
|---|---|---|
| | (N-hydroxy-2-methyl-2-(methylsulfonyl)-4-(4-(4-((4-nitrophenyl)ethynyl)phenyl)-3,6- | | dihydropyridin-1(2H)-yl)butanamide)
1H NMR (600 MHz, DMSO-d6); δ 11.01 (bs, 1H), 9.06 (bs, 1H), 8.25-8.23 (m, 2H), 7.80-7.78 (m, 2H), 7.57-7.55 (m, 2H), 7.51-7.49 (m, 2H), 6.28 (s, 1H), 3.11-3.98 (m, 2H), 3.04 (s, 3H), 2.63-2.58 (m, 4H), 2.44-2.32 (m, 4H), 1.45 (s, 3H).
MS (ESI, m/z): 498.2 [M + H]+.

(N-hydroxy-2-methyl-2-(methylsulfonyl)-4-(4-(4-(pyridin-3-ylethynyl)phenyl)-3,6-dihydropyridin-1(2H)-yl)butanamide)
1H NMR (600 MHz, DMSO-d6) δ; 11.01 (bs, 1H), 9.10 (bs, 1H), 8.75-8.74 (m, 1H), 8.57-8.56 (m, 1H), 7.97-7.95 (m, 1H), 7.59-7.39 (m, 5H), 6.27 (s, 1H), 3.15-3.11 (m, 2H), 3.05 (s, 3H), 2.65-2.59 (m, 2H), 2.42-2.31 (m, 2H), 1.85-1.83 (m, 2H), 1.45 (s, 3H), 1.21-1.17 (m, 2H).
MS (ESI, m/z): 454.2 [M + H]+.

(N-hydroxy-4-(4-(4-((4-hydroxyphenyl)ethynyl)phenyl)-3,6-dihydropyridin-1(2H)-yl)-2-methyl-2-(methylsulfonyl)butanamide)
1H NMR (600 MHz, DMSO-d6); δ 1.02 (bs, 1H), 10.16 (s, 1H), 9.07 (bs, 1H), 7.44-7.41 (m, 4H), 7.34-7.32 (m, 2H), 6.78-6.76 (m, 2H), 6.21 (s, 1H), 3.15-3.06 (m, 2H), 3.03 (s, 3H), 2.68-2.54 (m, 3H), 2.44-2.30 (m, 4H), 1.86-1.80 (m, 1H), 1.45 (s, 3H).
MS (ESI, m/z): 469.2 [M + H]+.

Example 38: Synthesis of N-hydroxy-2-methyl-4-(4-(4-((1-methyl-1H-imidazol-4-yl)ethynyl)phenyl)-3,6-dihydropyridin-1(2H)-yl)-2-(methylsulfonyl)butanamide

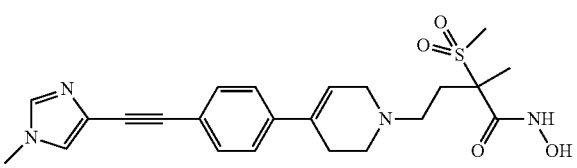

Step 1: Synthesis of 4-ethynyl-1-methyl-1H-imidazole

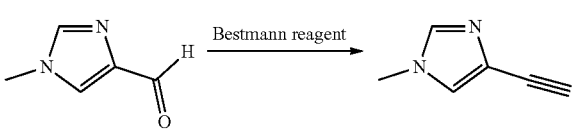

A solution of 1-methyl-1H-imidazole-4-carbaldehyde (2 g, 1 eq) in MeOH (180 ml) was cooled at 0° C. K₂CO₃ (5.02 g, 2 eq) and dimethyl (1-diazo-2-oxopropyl)phosphonate (7.7 g, 2.2 eq) was added. The mixture was stirred for 4 hr at 0° C., and extracted with dichloromethane and water. The organic layer was washed with sat. aq. NH₄Cl, dried over anhydrous MgSO₄ and concentrated in vacuo. The residue was purified with column chromatography to prepare the title compound (1.2 g, 62%).

1H NMR (600 MHz, CDCl₃-d1); δ7.60 (s, 1H), 7.32 (m, 1H), 3.37 (s, 3H), 3.48 (s, 1H).
MS (ESI, m/z): 107.1 [M+H]+.

Step 2: Synthesis of N-hydroxy-2-methyl-4-(4-(4-((1-methyl-1H-imidazol-4-yl)ethynyl)phenyl)-3,6-dihydropyridin-1(2H)-yl)-2-(methylsulfonyl)butanamide The title compound was prepared the procedures described for the synthesis of Example 1 (Synthesis of Hydroxamate) using 4-ethynyl-1-methyl-1H-imidazole.

1H NMR (600 MHz, DMSO-d6); δ11.02 (bs, 1H), 9.14 (bs, 1H), 7.76 (s, 1H), 7.52-7.48 (m, 4H), 7.29 (s, 1H), 6.26 (s, 1H), 3.69 (s, 3H), 3.16-3.04 (m, 5H), 2.66-2.56 (m, 3H), 2.46-2.38 (m, 4H), 1.86-1.76 (m, 1H), 1.44 (s, 3H).
MS (ESI, m/z): 457.2 [M+H]+.

Examples 39-41

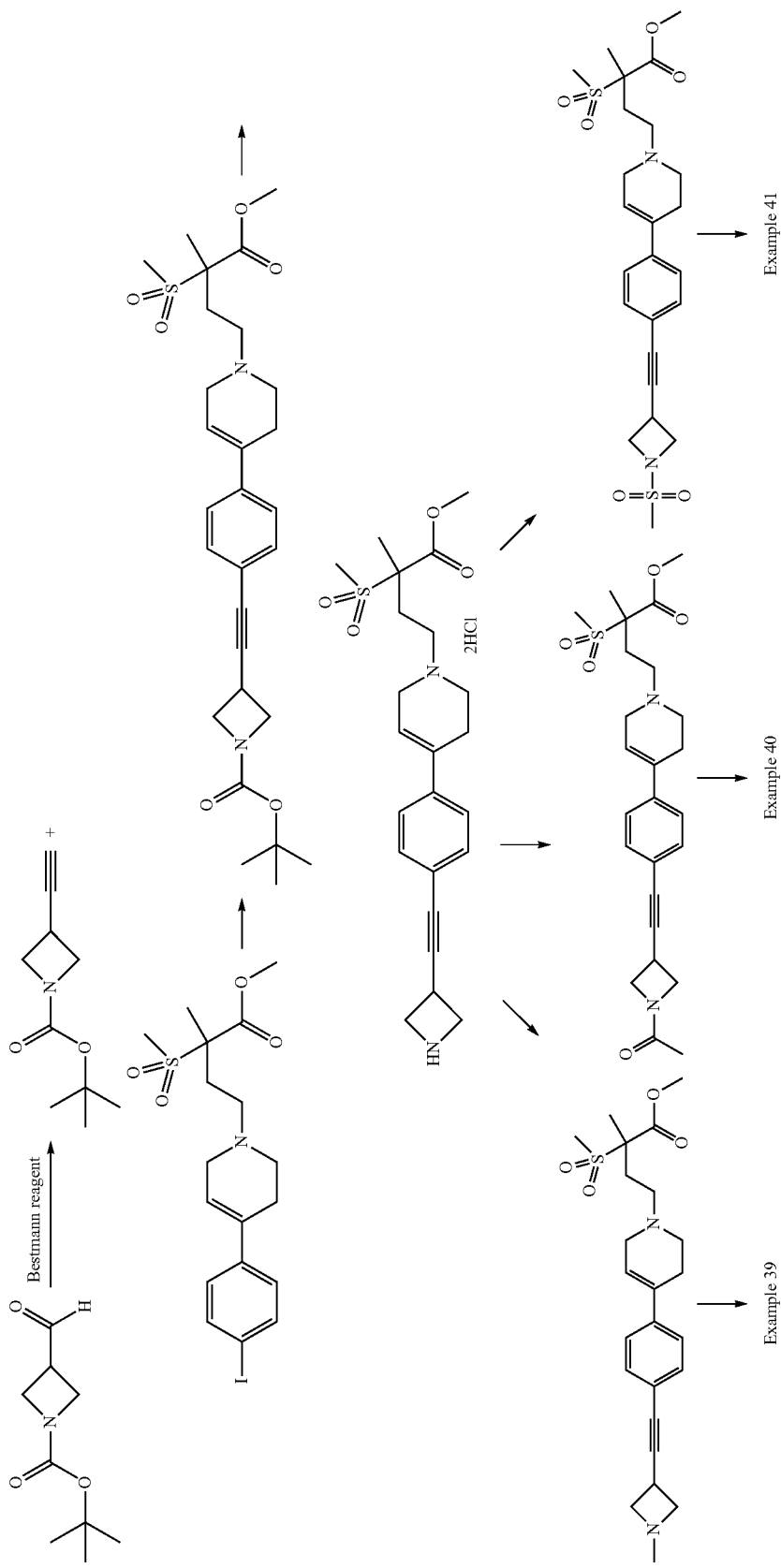

Preparation 4: Synthesis of Intermediate 4 {methyl 4-(4-(4-(azetidin-3-ylethynyl)phenyl)-3,6-dihydropyridin-1(2H)-yl)-2-methyl-2-(methylsulfonyl)butanoate dihydrochloride}

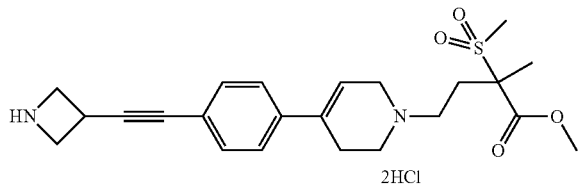 [SMILES: COC(=O)C(C)(CCN1CC=C(c2ccc(C#CC3CNC3)cc2)CC1)S(C)(=O)=O]

Step 1: Synthesis of tert-butyl 3-ethynylazetidine-1-carboxylate

A solution of tert-butyl 3-formylazetidine-1-carboxylate (7 g, 1 eq) in MeOH (378 ml) was cooled at 0° C. $K_2CO_3$(10.5 g, 2 eq), dimethyl (1-diazo-2-oxopropyl)phosphonate (15.8 g, 2.2 eq) was added. The mixture was stirred for 4 hr at 0° C., and extracted with dichloromethane and water. The organic layer was washed with sat. aq. $NH_4Cl$, dried over anhydrous $MgSO_4$ and concentrated in vacuo. The residue was purified with column chromatography to prepare the title compound (5.95 g, 87%).

$^1$H NMR (600 MHz, $CDCl_3$-d1); δ4.10-4.07 (m, 2H), 3.90-3.87 (m, 2H), 3.27-3.24 (m, 1H), 2.26-2.25 (m, 1H), 1.39 (s, 9H).

Step 2: Synthesis of tert-butyl 3-((4-(1-(4-methoxy-3-methyl-3-(methylsulfonyl)-4-oxobutyl)-1,2,3,6-tetrahydropyridin-4-yl)phenyl)ethynyl)azetidine-1-carboxylate To a solution of methyl 4-(4-(4-iodophenyl)-3,6-dihydropyridin-1(2H)-yl)-2-methyl-2-(methylsulfonyl)butanoate (Intermediate 2) (7 g, 1 eq) in a mixture of THF (30 ml)/toluene (30 ml) was added with CuI (0.28 g, 0.1 eq), $Pd(PPh_3)_2Cl_2$(1.03 g, 0.1 eq), $Et_3N$ (6.18 ml, 3 eq) and tert-butyl 3-ethynylazetidine-1-carboxylate (3.99 g, 1.5 eq). The mixture was stirred for 12 hr at room temperature, and extracted with ethyl acetate and water. The organic layer was washed with brine, dried over anhydrous $MgSO_4$ and concentrated in vacuo. The residue was purified with column chromatography to prepare the title compound (5 g, 64%).

$^1$H NMR (600 MHz, $CDCl_3$-d1); δ7.35-7.25 (m, 4H), 6.07 (s, 1H), 4.30 (s, 2H), 4.21-4.17 (m, 2H), 4.02-4.00 (m, 2H), 3.67 (s, 3H), 3.54-3.50 (m, 2H), 3.04 (s, 3H), 2.77-2.49 (m, 8H), 1.63 (s, 3H), 1.44 (s, 9H).

MS (ESI, m/z): 531.3 [M+H]$^+$.

Step 3: Synthesis of methyl 4-(4-(4-(azetidin-3-ylethynyl)phenyl)-3,6-dihydropyridin-1(2H)-yl)-2-methyl-2-(methylsulfonyl)butanoate dihydrochloride To a solution of tert-butyl 3-((4-(1-(4-methoxy-3-methyl-3-(methylsulfonyl)-4-oxobutyl)-1,2,3,6-tetrahydropyridin-4-yl)phenyl)ethynyl)azetidine-1-carboxylate (5 g, 1 eq) in dichloromethane (100 ml) was added with HCl solution (4N in cyclopentyl methyl ether, 24 ml, 10 eq). The mixture was stirred for 3 hr at room temperature. After then, the solvent was concentrated in vacuo to prepare the title compound (4.2 g, 89%).

$^1$H NMR (600 MHz, $CD_3OD$-d4); δ7.50-7.45 (m, 4H), 6.21 (s, 1H), 4.36-4.34 (m, 2H), 4.19-4.15 (m, 2H), 4.10-4.06 (m, 2H), 3.88-3.87 (m, 5H), 3.62-3.59 (m, 1H), 3.41-3.39 (m, 2H), 3.17 (s, 3H), 2.98-2.84 (m, 2H), 2.71-2.49 (m, 2H), 1.70 (s, 3H).

MS (ESI, m/z): 431.2 [M+H]$^+$.

Example 39: Synthesis of N-hydroxy-2-methyl-4-(4-(4-((1-methylazetidin-3-yl)ethynyl)phenyl)-3,6-dihydropyridin-1(2H)-yl)-2-(methylsulfonyl)butanamidedihydrocloride

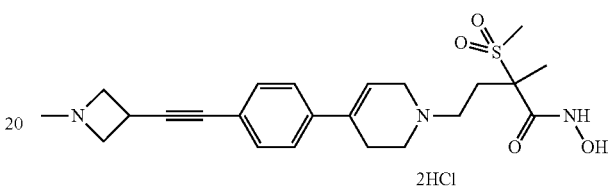

Step 1: Synthesis of methyl 2-methyl-4-(4-(4-((1-methylazetidin-3-yl)ethynyl)phenyl)-3,6-dihydropyridin-1(2H)-yl)-2-(methylsulfonyl)butanoate To a solution of methyl 4-(4-(4-(azetidin-3-ylethynyl)phenyl)-3,6-dihydropyridin-1(2H)-yl)-2-methyl-2-(methylsulfonyl)butanoate dihydrochloride (Intermediate 4) (1.5 g, 1 eq) in dichloromethane (30 ml) was added with formaldehyde (37 wt %, 0.89 ml, 4 eq) and sodium triacetoxyborohydride (2.53 g, 4 eq). The mixture was stirred for 5 hr at room temperature, and extracted with ethyl acetate and water. The organic layer was washed with sat. aq. $NaHCO_3$, dried over anhydrous $MgSO_4$ and concentrated in vacuo. The residue was purified with column chromatography to prepare the title compound (0.9 g, 68%).

$^1$H NMR (600 MHz, $CDCl_3$-d1); δ7.34-7.32 (m, 2H), 7.29-7.28 (m, 2H), 6.07 (s, 1H), 3.76-3.74 (m, 2H), 3.66 (s, 3H), 3.46-3.45 (m, 1H), 3.22-3.19 (m, 3H), 3.02-2.99 (m, 4H), 2.78-2.76 (m, 1H), 2.65-2.53 (m, 4H), 2.47-2.46 (m, 2H), 2.38 (s, 3H), 1.97-1.96 (m, 1H), 1.62 (s, 3H).

MS (ESI, m/z): 445.2 [M+H]$^+$.

Step 2-4: N-hydroxy-2-methyl-4-(4-(4-((1-methylazetidin-3-yl)ethynyl)phenyl)-3,6-dihydropyridin-1(2H)-yl)-2-(methylsulfonyl)butanamide The title compound was prepared the procedures described for the synthesis of Example 1, step 2-4 (Synthesis of Hydroxamate) from methyl 2-methyl-4-(4-(4-((1-methylazetidin-3-yl)ethynyl)phenyl)-3,6-dihydropyridin-1(2H)-yl)-2-(methylsulfonyl)butanoate.

$^1$H NMR (600 MHz, DMSO-d6); δ11.22-11.04 (m, 3H), 9.35 (bs, 1H), 7.52-7.50 (m, 2H), 7.47-7.44 (m, 2H), 6.28 (s, 1H), 4.38-4.00 (m, 4H), 3.83-3.77 (m, 2H), 3.36-3.34 (m, 2H), 3.11 (s, 3H), 3.08-2.82 (m, 5H), 2.73-2.69 (m, 2H), 2.23-2.21 (m, 1H), 1.51 (s, 3H).

MS (ESI, m/z): 446.2 [M+H]$^+$.

Example 40: Synthesis of 4-(4-(4-((1-acetylazetidin-3-yl)ethynyl)phenyl)-3,6-dihydropyridin-1(2H)-yl)-N-hydroxy-2-methyl-2-(methylsulfonyl)butanamide

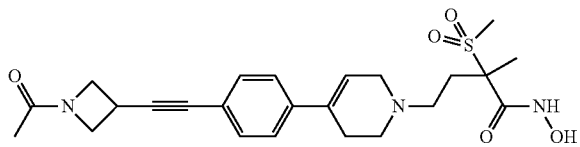 [SMILES: CC(=O)N1CC(C#Cc2ccc(C3=CCN(CCC(C)(C(=O)NO)S(C)(=O)=O)CC3)cc2)C1]

Step 1: Synthesis of methyl 4-(4-(4-((1-acetylazetidin-3-yl)ethynyl)phenyl)-3,6-dihydropyridin-1(2H)-yl)-2-methyl-2-(methylsulfonyl)butanoate To a solution of methyl 4-(4-(4-(azetidin-3-ylethynyl)phenyl)-3,6-dihydropyridin-1(2H)-yl)-2-methyl-2-(methylsulfonyl)butanoate dihydrochloride (Intermediate 4) (800 mg, 1 eq) in dichloromethane (15 ml) was added with Et$_3$N (0.89 ml, 4 eq) and acetyl chloride (0.17 ml, 1.5 eq). The mixture was stirred for 2 hr at 0° C., and extracted with dichloromethane and water. The organic layer was washed with brine, dried over anhydrous MgSO$_4$ and concentrated in vacuo. The residue was purified with column chromatography to prepare the title compound (560 mg, 75%).

$^1$H NMR (600 MHz, CDCl$_3$-d1); δ7.35-7.32 (m, 4H), 6.06 (s, 1H), 4.41-4.29 (m, 2H), 4.20-4.07 (m, 2H), 3.87-3.61 (m, 7H), 3.14-3.07 (m, 5H), 2.77-2.59 (m, 4H), 2.04-2.03 (m, 1H), 1.88 (s, 3H), 1.67 (s, 3H).

MS (ESI, m/z): 473.2 [M+H]$^+$.

Step 2-4: Synthesis of 4-(4-(4-((1-acetylazetidin-3-yl)ethynyl)phenyl)-3,6-dihydropyridin-1(2H)-yl)-N-hydroxy-2-methyl-2-(methylsulfonyl)butanamide The title compound was prepared the procedures described for the synthesis of Example 1, step 2-4 (Synthesis of Hydroxamate) from methyl 4-(4-(4-((1-acetylazetidin-3-yl)ethynyl)phenyl)-3,6-dihydropyridin-1(2H)-yl)-2-methyl-2-(methylsulfonyl)butanoate.

$^1$H NMR (600 MHz, DMSO-d6); δ11.0 (bs, 1H), 9.11 (bs, 1H), 7.42-7.40 (m, 2H), 7.38-7.36 (m, 2H), 6.20 (s, 1H), 4.41-4.38 (m, 2H), 4.13-4.10 (m, 2H), 3.78-3.67 (m, 2H), 3.15-3.14 (m, 2H), 3.04 (s, 3H), 2.62-2.56 (m, 2H), 2.49-2.43 (m, 4H), 2.32-2.30 (m, 1H), 1.74 (s, 3H), 1.44 (s, 3H).

MS (ESI, m/z): 474.1 [M+H]$^+$.

Example 41: Synthesis of N-hydroxy-2-methyl-2-(methylsulfonyl)-4-(4-(4-((1-(methylsulfonyl) azetidin-3-yl)ethynyl)phenyl)-3,6-dihydropyridin-1(2H)-yl)butanamide

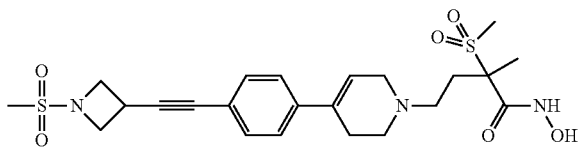

Step 1: Synthesis of methyl 2-methyl-2-(methylsulfonyl)-4-(4-(4-((1-(methylsulfonyl)azetidin-3-yl)ethynyl)phenyl)-3,6-dihydropyridin-1(2H)-yl)butanoate To a solution of methyl 4-(4-(4-(azetidin-3-ylethynyl)phenyl)-3,6-dihydropyridin-1(2H)-yl)-2-methyl-2-(methylsulfonyl)butanoate dihydrochloride (Intermediate 4) (600 mg, 1 eq) in DMF (15 ml) was added with N,N-diisopropylethylamine (0.83 ml, 4 eq) and methanesulfonyl chloride (0.14 ml, 1.5 eq). The mixture was stirred for 2 hr at 0° C., and extracted with ethyl acetate and water. The organic layer was washed with brine, dried over anhydrous MgSO$_4$ and concentrated in vacuo. The residue was purified with column chromatography to prepare the title compound (220 mg, 36%).

$^1$H NMR (600 MHz, CDCl$_3$-d1); δ7.37-7.36 (m, 2H), 7.31-7.30 (m, 2H), 6.03 (s, 1H), 4.19-4.02 (m, 6H), 3.63-3.60 (m, 2H), 3.13-3.02 (m, 5H), 2.94-2.87 (m, 2H), 2.75-2.69 (m, 1H), 2.26-2.20 (m, 2H), 2.03 (s, 3H), 1.23 (s, 3H).

MS (ESI, m/z): 509.2 [M+H]$^+$.

Step 2-4: Synthesis of N-hydroxy-2-methyl-2-(methylsulfonyl)-4-(4-(4-((1-(methylsulfonyl)azetidin-3-yl)ethynyl)phenyl)-3,6-dihydropyridin-1(2H)-yl)butanamide The title compound was prepared the procedures described for the synthesis of Example 1, step 2-4 (Synthesis of Hydroxamate) from methyl 2-methyl-2-(methylsulfonyl)-4-(4-(4-((1-(methylsulfonyl)azetidin-3-yl)ethynyl)phenyl)-3,6-dihydropyridin-1(2H)-yl)butanoate.

$^1$H NMR (600 MHz, CD$_3$OD-d4); δ7.41-7.36 (m, 4H), 6.17 (s, 1H), 4.19-4.16 (m, 2H), 3.98-3.95 (m, 2H), 3.13 (s, 3H), 2.97 (s, 3H), 2.88-2.84 (m, 2H), 2.61-2.54 (m, 4H), 2.23-2.21 (m, 1H), 1.59 (s, 3H).

MS (ESI, m/z): 510.2 [M+H]$^+$.

Preparation 5: Synthesis of Intermediate 5 {tert-butyl 4-(4-(2,2-dibromovinyl)-3-fluorophenyl)-3,6-dihydropyridine-1(2H)-carboxylate}

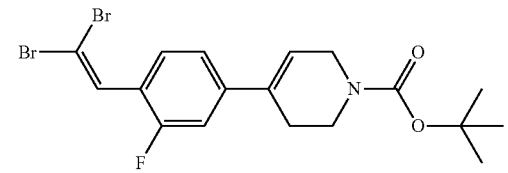

Step 1: Synthesis of tert-butyl 4-(3-fluoro-4-formylphenyl)-3,6-dihydropyridine-1(2H)-carboxylate

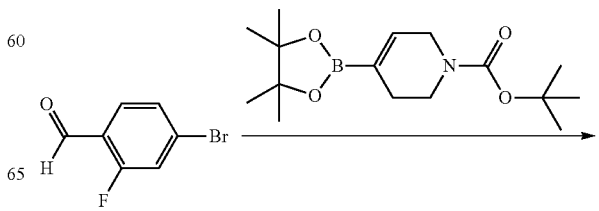

63

-continued

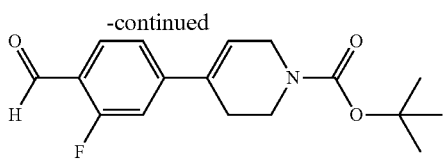

To a solution of 4-bromo-2-fluorobenzaldehyde (6 g, 1 eq) in a mixture of 1,4-dioxane (100 ml)/water (20 ml) was added with Pd(PPh$_3$)$_2$Cl$_2$(2.07 g, 0.1 eq), K$_2$CO$_3$(12.25 g, 3 eq) and tert-butyl 4-(4,4,5,5-tetramethyl-1,3,2-dioxaborolan-2-yl)-3,6-dihydropyridine-1(2H)-carboxylate (10.97 g, 1.2 eq). The mixture was stirred for 4 hr at 110° C., cooled down to room temperature and extracted with ethyl acetate and water. The organic layer was washed with brine, dried over anhydrous MgSO$_4$ and concentrated in vacuo. The residue was purified with column chromatography to prepare the title compound (7.8 g, 86%).

$^1$H NMR (600 MHz, CDCl$_3$-d1); δ10.32 (s, 1H), 7.84-7.82 (m, 1H), 7.29-7.26 (m, 1H), 7.16-7.14 (m, 1H), 6.24 (bs, 1H), 4.14-4.10 (m, 2H), 3.66-3.64 (m, 2H), 2.54-2.50 (m, 2H), 1.49 (s, 9H).

Step 2: Synthesis of tert-butyl 4-(4-(2,2-dibromovinyl)-3-fluorophenyl)-3,6-dihydropyridine-1(2H)-carboxylate

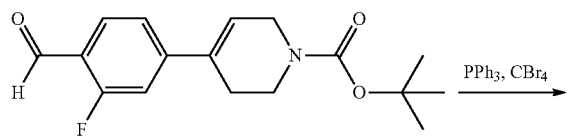

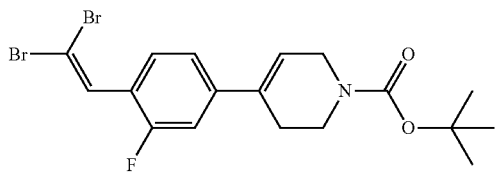 [SMILES: CC(C)(C)OC(=O)N1CC=C(c2ccc(C=C(Br)Br)c(F)c2)CC1]

To a solution of tert-butyl 4-(3-fluoro-4-formylphenyl)-3,6-dihydropyridine-1(2H)-carboxylate (3 g, 1 eq) in dichloromethane (50 ml) was added with carbon tetrabromide (4.89 g, 1.5 eq) and triphenylphosphine (7.73 g, 3 eq). The mixture was stirred for 1 hr at 0° C., and extracted with dichloromethane and water. The organic layer was washed with brine, dried over anhydrous MgSO$_4$ and concentrated in vacuo. The residue was purified with column chromatography to prepare the title compound (4.13 g, 91%).

$^1$H NMR (600 MHz, CDCl$_3$-d1); δ7.78-7.76 (m, 1H), 7.54 (s, 1H), 7.18-7.16 (m, 1H), 7.08-7.06 (m, 1H), 6.11 (bs, 1H), 4.11-4.09 (m, 2H), 3.65-3.60 (m, 2H), 2.51-2.47 (m, 2H), 1.49 (s, 9H).

64

Example 42: Synthesis of 4-(4-(3-fluoro-4-(7-hydroxyhepta-1,3-diyn-1-yl)phenyl)-3,6-dihydropyridin-1(2H)-yl)-N-hydroxy-2-methyl-2-(methylsulfonyl)butanamide

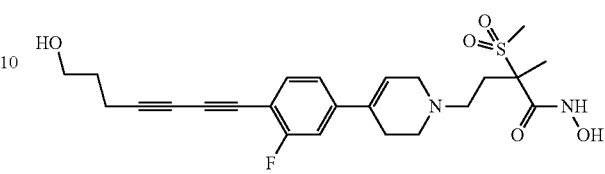

Step 1: Synthesis of tert-butyl 4-(3-fluoro-4-(7-hydroxyhepta-1,3-diyn-1-yl)phenyl)-3,6-dihydropyridine-1(2H)-carboxylate

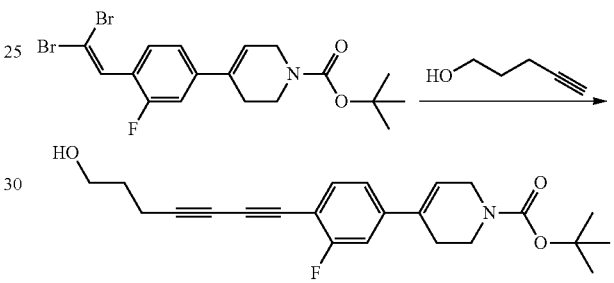

To a solution of tert-butyl 4-(4-(2,2-dibromovinyl)-3-fluorophenyl)-3,6-dihydropyridine-1(2H)-carboxylate (Intermediate 5) (2.29 g, 1 eq) in DMF was added with Pd(PPh$_3$)$_2$Cl$_2$(0.35 g, 0.1 eq), triphenylphosphine (0.13 g, 0.1 eq), Et$_3$N (2.1 ml, 3 eq) and pent-4-yn-1-ol (0.93 ml, 2 eq) The mixture was stirred for 2 hr at 80° C., cooled down to room temperature, and extracted with ethyl acetate and water. The organic layer was washed with brine, dried over anhydrous MgSO$_4$ and concentrated in vacuo. The residue was purified with column chromatography to prepare the title compound (790 mg, 42%).

$^1$H NMR (600 MHz, CDCl$_3$-d1); δ7.41-7.38 (m, 1H), 7.11-7.09 (m, 1H), 7.07-7.06 (m, 1H), 6.10 (bs, 1H), 4.10-4.06 (m, 2H), 3.78 (t, J=6 Hz, 2H), 3.64-3.60 (m, 2H), 2.52 (t, J=6.6 Hz, 2H), 2.49-2.45 (m, 2H), 1.86-1.81 (m, 2H), 1.48 (s, 9H).

Step 2: Synthesis of 7-(2-fluoro-4-(1,2,3,6-tetrahydropyridin-4-yl)phenyl)hepta-4,6-diyn-1-ol hydrochloride

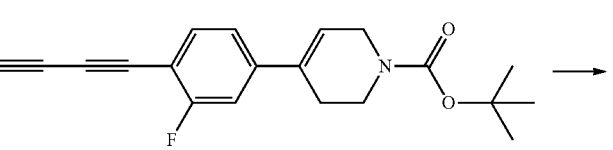

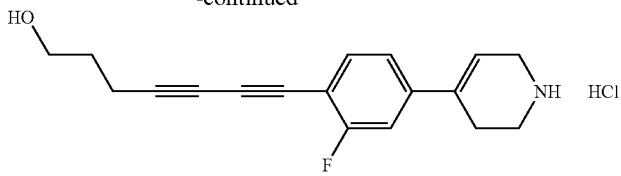

To a solution of tert-butyl 4-(3-fluoro-4-(7-hydroxyhepta-1,3-diyn-1-yl)phenyl)-3,6-dihydropyridine-1(2H)-carboxylate (790 mg, 1 eq) in MeOH was added with conc-HCl (1.7 ml, 10 eq). The mixture was stirred for 1 hr at 110° C., cooled down to room temperature, and concentrated in vacuo. The residue was diluted in MeOH (2 ml) and poured into diethyl ether (50 ml). The precipitated solid was filtered off to prepare the title compound (576 mg, 87%).

$^1$H NMR (600 MHz, DMSO-d6); δ9.34 (bs, 2H), 7.63-7.60 (m, 1H), 7.49-7.47 (m, 1H), 7.37-7.36 (m, 1H), 6.41 (s, 1H), 3.78-3.74 (m, 2H), 3.47 (t, J=5.4 Hz, 2H), 3.30-3.26 (m, 2H), 2.69-2.65 (m, 2H), 2.50-2.47 (m, 2H), 1.68-1.63 (m, 2H).

Step 3: Synthesis of methyl 4-(4-(3-fluoro-4-(7-hydroxyhepta-1,3-diyn-1-yl)phenyl)-3,6-dihydropyridin-1(2H)-yl)-2-methyl-2-(methylsulfonyl)butanoate

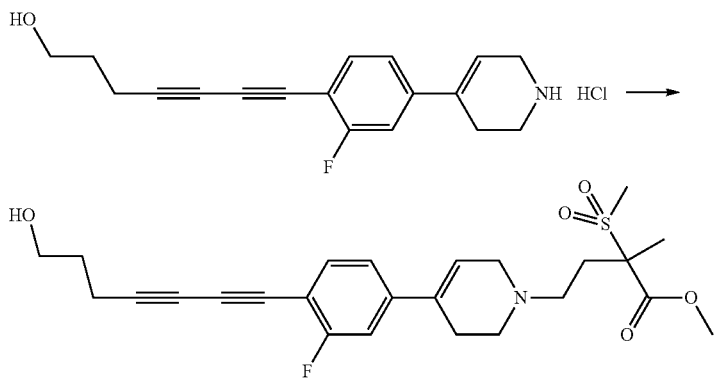

To a solution of 7-(2-fluoro-4-(1,2,3,6-tetrahydropyridin-4-yl)phenyl)hepta-4,6-diyn-1-ol hydrochloride (570 mg, 1 eq) in DMF (12 ml) was added with N,N-diisopropylethylamine (0.93 ml, 3 eq) and methyl 4-bromo-2-methyl-2-(methylsulfonyl)butanoate (Intermediate 1) (584 mg, 1.2 eq). The mixture was stirred for 12 hr at 60° C., cooled down to room temperature, and extracted with ethyl acetate and water. The organic layer was washed with brine, dried over anhydrous MgSO$_4$ and concentrated in vacuo. The residue was purified with column chromatography to prepare the title compound (230 mg, 27%).

le;2q$^1$H NMR (600 MHz, CDCl$_3$-d1); δ7.39-7.37 (m, 1H), 7.11-7.09 (m, 1H), 7.07-7.05 (m, 1H), 6.13 (s, 1H), 3.78 (t, J=6 Hz, 2H), 3.67 (s, 3H), 3.24-3.21 (m, 1H), 3.05 (s, 3H), 3.04-3.01 (1H), 2.79-2.76 (m, 1H), 2.67-2.53 (m, 4H), 2.51 (t, J=6.6 Hz, 2H), 2.45-2.42 (m, 2H), 2.00-1.98 (m, 1H), 1.85-1.81 (m, 2H), 1.63 (s, 3H).

Step 4: Synthesis of 4-(4-(3-fluoro-4-(7-hydroxyhepta-1,3-diyn-1-yl)phenyl)-3,6-dihydropyridin-1(2H)-yl)-2-methyl-2-(methylsulfonyl)butanoic acid

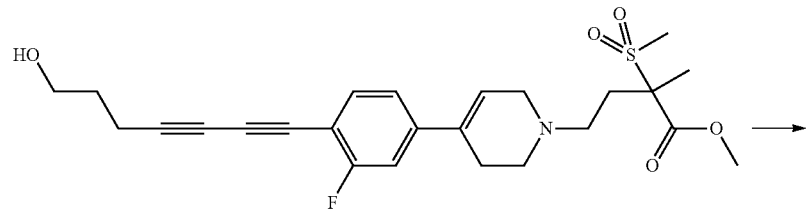

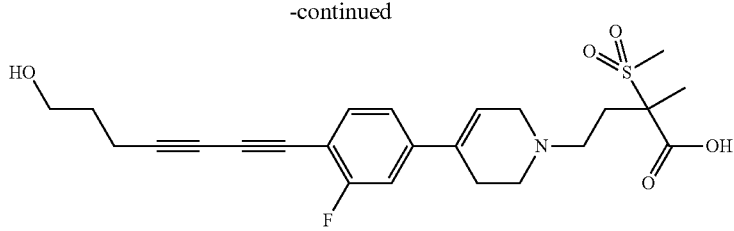

To a solution of methyl 4-(4-(3-fluoro-4-(7-hydroxyhepta-1,3-diyn-1-yl)phenyl)-3,6-dihydropyridin-1(2H)-yl)-2-methyl-2-(methylsulfonyl)butanoate (230 mg, 1 eq) in a mixture of THF (8 ml)/MeOH (2 ml) was added with 2N—LiOH (0.73 mL, 3 eq) solution. The mixture was stirred for 2 hr at room temperature. The solvent was removed under reduced pressure. The residue was diluted with water (10 ml) and adjusted the pH to 4.0. The precipitated solid was filtered off to prepare the title compound (119 mg, 53%), which was used for next step without further purification.

MS (ESI, m/z): 462.1 [M+H]$^+$.

Step 5: Synthesis of 4-(4-(3-fluoro-4-(7-hydroxyhepta-1,3-diyn-1-yl)phenyl)-3,6-dihydropyridin-1(2H)-yl)-2-methyl-2-(methylsulfonyl)-N-((tetrahydro-2H-pyran-2-yl)oxy)butanamide

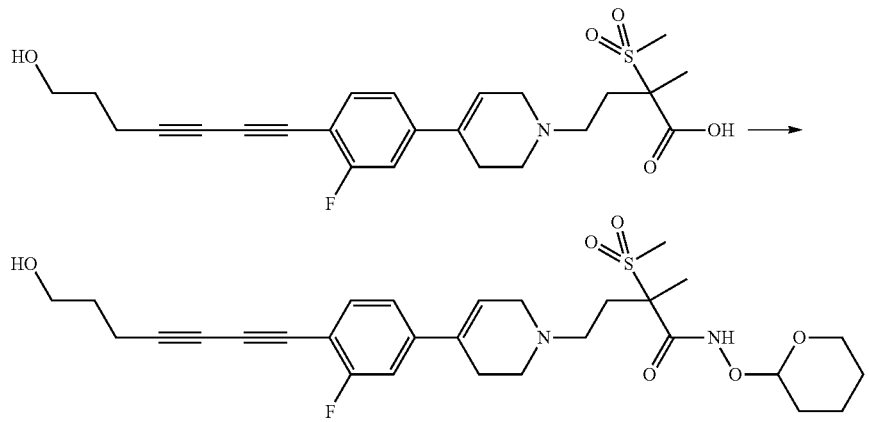

To a solution of of 4-(4-(3-fluoro-4-(7-hydroxyhepta-1,3-diyn-1-yl)phenyl)-3,6-dihydropyridin-1(2H)-yl)-2-methyl-2-(methylsulfonyl)butanoic acid (119 mg, 1 eq) in DMF (10 ml) was added with HATU (137 mg, 1.4 eq), HOBT (55 mg, 1.4 eq), Et$_3$N (0.11 ml, 3 eq) and O-(tetrahydro-2H-pyran-2-yl)hydroxylamine hydrochloride (60 mg, 2 eq). The mixture was stirred for 1 hr at room temperature, and extracted with ethyl acetate and water. The organic layer was washed with brine, dried over anhydrous MgSO$_4$ and concentrated in vacuo. The residue was purified with column chromatography to prepare the title compound (127 mg, 88%).

MS (ESI, m/z): 561.2 [M+H]$^+$.

Step 6: Synthesis of 4-(4-(3-fluoro-4-(7-hydroxyhepta-1,3-diyn-1-yl)phenyl)-3,6-dihydropyridin-1(2H)-yl)-N-hydroxy-2-methyl-2-(methylsulfonyl)butanamide

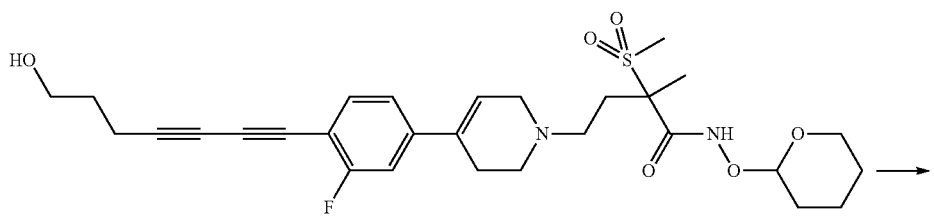

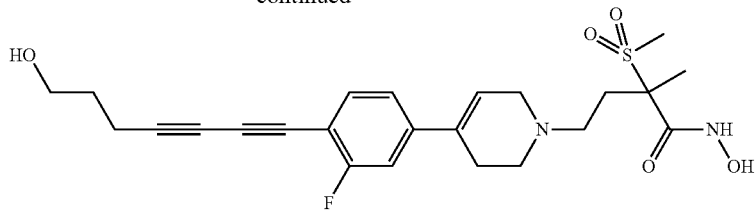

To a solution of 4-(4-(3-fluoro-4-(7-hydroxyhepta-1,3-diyn-1-yl)phenyl)-3,6-dihydropyridin-1(2H)-yl)-2-methyl-2-(methylsulfonyl)-N-((tetrahydro-2H-pyran-2-yl)oxy)butanamide (127 mg, 1 eq) in MeOH (6 ml) was added with HCl solution in MeOH (1.25N, 0.54 ml, 3 eq). The mixture was stirred for 2 hr at room temperature. The solvent was removed under reduced pressure. The residue was diluted with water (6 ml) and adjusted the pH to 7.0. The water was concentrated in vacuo and the resulting residue was purified with column chromatography to prepare the title compound (40 mg, 37%).

$^1$H NMR (600 MHz, DMSO-d6); δ 10.99 (bs, 1H), 9.12 (bs, 1H), 7.56-7.54 (m, 1H), 7.39-7.36 (m, 1H), 7.31-7.28 (m, 1H), 6.37 (s, 1H), 4.60-4.58 (m, 1H), 3.48-3.45 (m, 2H), 3.35-3.33 (m, 2H), 3.13-3.08 (m, 2H), 3.06 (s, 3H), 2.64-2.58 (m, 2H), 2.51-2.43 (m, 4H), 2.37-2.29 (m, 1H), 1.85-1.78 (m, 1H), 1.66-1.62 (m, 2H), 1.46 (s, 3H).

MS (ESI, m/z): 477.2 [M+H]$^+$.

Examples 43-45

The terminal acetylenes listed in the following table were used to prepare compounds of Examples 43-45 in the same manner as Example 42.

| Example | Structure (Name) | Terminal acetylene |
|---|---|---|
| | 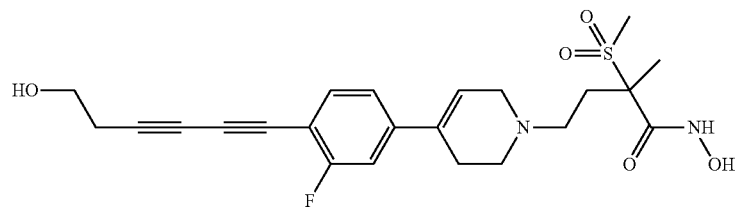 [SMILES: CC(CCN1CC=C(c2ccc(C#CC#CCCO)c(F)c2)CC1)(C(=O)NO)S(C)(=O)=O] (4-(4-(3-fluoro-4-(6-hydroxyhexa-1,3-diyn-1-yl)phenyl)-3,6-dihydropyridin-1(2H)-yl)-N-hydroxy-2-methyl-2-(methylsulfonyl)butanamide) $^1$H NMR (600 MHz, DMSO-d6); δ 10.99 (bs, 1H), 9.11 (bs, 1H), 7.56-7.53 (m, 1H), 7.39-7.37 (m, 1H), 7.31-7.29 (m, 1H), 6.36 (s, 1H), 3.57-3.55 (m, 2H), 3.17-3.10 (m, 2H), 3.06 (s, 3H), 2.65-2.29 (m, 10H), 1.45 (s, 3H). MS (ESI, m/z): 463.2 [M + H]$^+$. | |
| 44 | 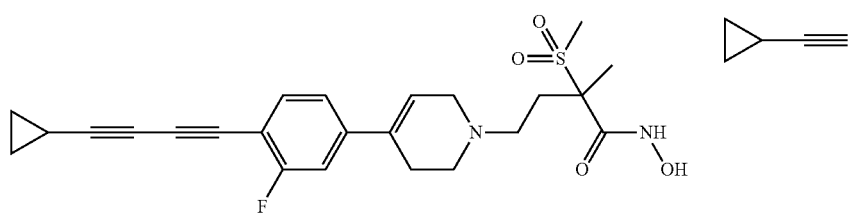 (4-(4-(4-(cyclopropylbuta-1,3-diyn-1-yl)-3-fluorophenyl)-3,6-dihydropyridin-1(2H)-yl)-N-hydroxy-2-methyl-2-(methylsulfonyl)butanamide) $^1$H NMR (600 MHz, DMSO-d6); δ 10.99 (bs, 1H), 9.12 (bs, 1H), 7.54-7.52 (m, 1H), 7.38-7.36 (m, 1H), 7.30-7.28 (m, 1H), 6.36 (s, 1H), 3.15-3.07 (m, 2H), 3.06 (s, 3H), 2.66-2.56 (m, 2H), 2.48-2.31 (m, 6H), 1.61-1.59 (m, 1H), 1.46 (s, 3H), 0.95-0.91 (m, 2H), 0.82-0.79 (m, 2H). MS (ESI, m/z): 463.2 [M + H]$^+$. | |

| Example | Structure (Name) | Terminal acetylene |
|---|---|---|
| | 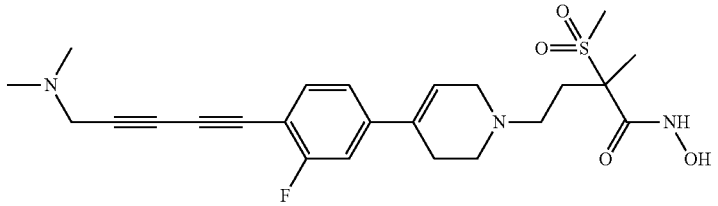 [SMILES: CN(C)CC#CC#Cc1ccc(C2=CCN(CCC(C)(C(=O)NO)S(C)(=O)=O)CC2)cc1F]<br>(4-(4-(4-(5-(dimethylamino)penta-1,3-diyn-1-yl)-3-fluorophenyl)-3,6-dihydropyridin-1(2H)-yl)-N-hydroxy-2-methyl-2-(methylsulfonyl)butanamide)<br>$^1$H NMR (600 MHz, DMSO-d6); δ 10.97 (bs, 1H), 9.11 (bs, 1H), 7.58-7.56 (m, 1H), 7.39-7.37 (m, 1H), 7.31-7.29 (m, 1H), 6.36 (s, 1H), 3.48 (s, 2H), 3.16-3.08 (2H), 3.04 (s, 3H), 2.66-2.56 (m, 3H), 2.48-2.38 (m, 3H), 2.36-2.28 (m, 1H), 2.19 (s, 6H), 1.86-1.76 (m, 1H), 1.44 (s, 3H).<br>MS (ESI, m/z): 476.2 [M + H]$^+$. | |

Preparation 6: Synthesis of Intermediate 6 {tert-butyl 4-(4-(2,2-dibromovinyl)phenyl)-3,6-dihydropyridine-1(2H)-carboxylate}

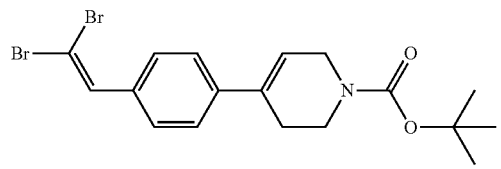 [SMILES: CC(C)(C)OC(=O)N1CC=C(c2ccc(C=C(Br)Br)cc2)CC1]

The title compound was prepared the procedures described for the Preparation 5 using 4-bromobenzaldehyde.

$^1$H NMR (600 MHz, CDCl$_3$-d1); δ7.52 (d, J=9 Hz, 2H), 7.46 (s, 1H), 7.37 (d, J=8.4 Hz, 2H), 6.09 (bs, 1H), 4.09-4.06 (m, 2H), 3.66-3.61 (m, 2H), 2.55-2.49 (m, 2H), 1.49 (s, 9H).

Examples 46-51

The Intermediate 6 as a starting material and the terminal acetylenes listed in the following table were used to prepare compounds of Example 46-51 in the same manner as Example 42.

| Example | Structure (Name) | Terminal acetylene |
|---|---|---|
| | 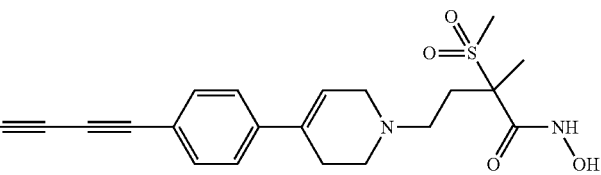<br>(N-hydroxy-4-(4-(4-(7-hydroxyhepta-1,3-diyn-1-yl)phenyl)-3,6-dihydropyridin-1(2H)-yl)-2-methyl-2-(methylsulfonyl)butanamide)<br>$^1$H NMR (600 MHz, DMSO-d6); δ 11.01 (bs, 1H), 9.10 (bs, 1H), 7.49-7.43 (m, 4H), 6.26 (s, 1H), 4.60-4.57 (m, 2H), 3.49-3.44 (m, 2H), 3.16-3.06 (m, 5H), 2.66-2.56 (m, 2H), 2.47-2.30 (m, 6H), 1.67-1.61 (m, 2H), 1.46 (s, 3H).<br>MS (ESI, m/z): 431.0 [M + H]$^+$. | |
| | 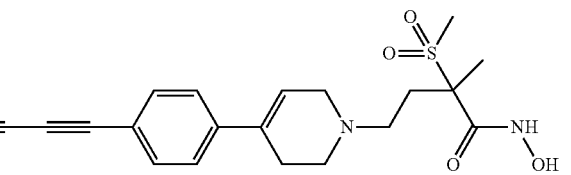<br>(N-hydroxy-4-(4-(4-(6-hydroxyhexa-1,3-diyn-1-yl)phenyl)-3,6-dihydropyridin-1(2H)-yl)-2-methyl-2-(methylsulfonyl)butanamide)<br>$^1$H NMR (600 MHz, DMSO-d6); δ 11.00 (bs, 1H), 9.11 (bs, 1H), 7.48-7.46 (m, 2H), 7.44-7.43 (m, 2H), | |

| Example | Structure (Name) | Terminal acetylene |
|---|---|---|
| | 6.24 (s, 1H), 4.96 (t, J = 6.0 Hz, 1H), 3.54-3.51 (m, 2H), 3.14-3.06 (m, 2H), 3.04 (s, 3H), 2.66-2.56 (m, 2H), 2.52 (t, J = 6.0 Hz, 2H), 2.48-2.38 (m, 4H), 2.34-2.26 (m, 1H), 1.84-1.76 (m, 1H), 1.44 (s, 3H).<br>MS (ESI, m/z): 445.2 [M + H]+. | |
| | 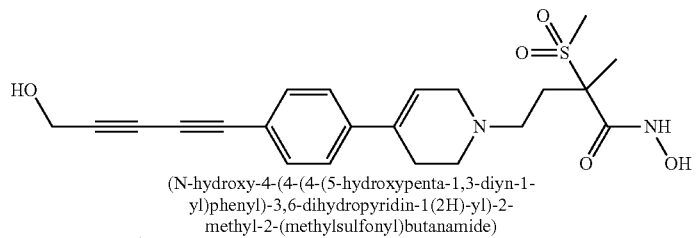<br>(N-hydroxy-4-(4-(4-(5-hydroxypenta-1,3-diyn-1-yl)phenyl)-3,6-dihydropyridin-1(2H)-yl)-2-methyl-2-(methylsulfonyl)butanamide)<br>1H NMR (600 MHz, DMSO-d6); δ 10.99 (bs, 1H), 9.10 (bs, 1H), 7.49-7.48 (m, 2H), 7.45-7.43 (m, 2H), 6.25 (s, 1H), 5.45 (t, J = 6.0 Hz, 1H), 4.23 (d, J = 6.0 Hz, 2H), 3.14-3.08 (m, 2H), 3.03 (s, 3H), 2.66-2.56 (m, 2H), 2.48-2.38 (m, 4H), 2.42-2.38 (m, 1H), 1.86-1.76 (m, 1H), 1.44 (s, 3H).<br>MS (ESI, m/z): 431.0 [M + H]+. | |
| 49 | 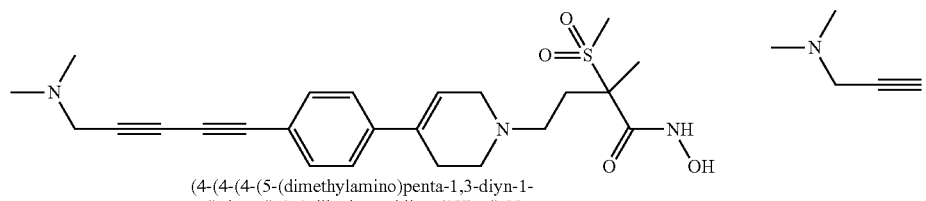<br>(4-(4-(4-(5-(dimethylamino)penta-1,3-diyn-1-yl)phenyl)-3,6-dihydropyridin-1(2H)-yl)-N-hydroxy-2-methyl-2-(methylsulfonyl)butanamide)<br>1H NMR (600 MHz, DMSO-d6); δ 11.01 (bs, 1H), 9.13 (bs, 1H), 7.53-7.46 (m, 4H), 6.28 (s, 1H), 3.49-3.48 (m, 2H), 3.10-3.09 (m, 2H), 3.06 (s, 3H), 2.61-2.60 (m, 2H), 2.47-2.34 (m, 6H), 2.22 (s, 6H), 1.46 (s, 3H).<br>MS (ESI, m/z): 458.2 [M + H]+. | |
| | 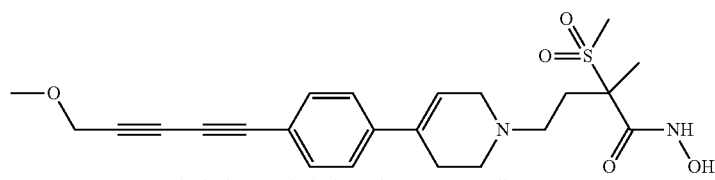 [SMILES: COCC#CC#Cc1ccc(C2=CCN(CCC(C)(C(=O)NO)S(C)(=O)=O)CC2)cc1]<br>(N-hydroxy-4-(4-(4-(5-methoxypenta-1,3-diyn-1-yl)phenyl)-3,6-dihydropyridin-1(2H)-yl)-2-methyl-2-(methylsulfonyl)butanamide)<br>1H NMR (600 MHz, DMSO-d6) δ; 11.02 (bs, 1H), 9.08 (bs, 1H), 7.54-7.47 (m, 4H), 6.29 (s, 1H), 4.31 (s, 2H), 3.33 (s, 3H), 3.18-3.10 (m, 2H), 3.06 (s, 3H), 2.65-2.57 (m, 2H), 2.48-2.42 (m, 4H), 2.36-2.30 (m, 1H), 1.88-1.80 (m, 1H), 1.45 (s, 3H).<br>MS (ESI, m/z): 445.2 [M + H]+. | |
| | 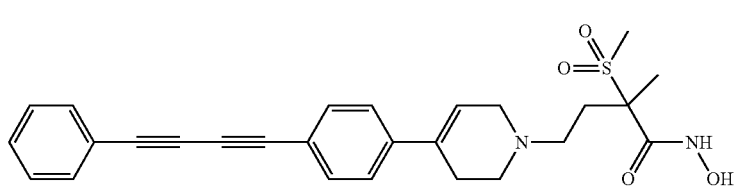 [SMILES: CC(CCN1CC=C(c2ccc(C#CC#Cc3ccccc3)cc2)CC1)(C(=O)NO)S(C)(=O)=O]<br>(N-hydroxy-2-methyl-2-(methylsulfonyl)-4-(4-(4-(phenylbuta-1,3-diyn-1-yl)phenyl)-3,6-dihydropyridin-1(2H)-yl)butanamide)<br>1H NMR (600 MHz, DMSO-d6); δ 10.99 (bs, 1H), 9.10 (bs, 1H), 7.59-7.57 (m, 2H), 7.55-7.53 (m, 2H), 7.48-7.46 (m, 2H), 7.43-7.41 (m, 2H), 6.27 (s, | |

1H), 3.18-3.08 (m, 2H), 3.04 (s, 3H), 2.66-2.56 (m, 3H), 2.48-2.38 (m, 3H), 2.36-2.28 (m, 1H), 1.86-1.76 (m, 1H), 1.44 (s, 3H). MS (ESI, m/z): 477.2 [M + H]+.

Preparation 7: Synthesis of Intermediate 7 {tert-butyl 4-ethynyl-3,6-dihydropyridine-1(2H)-carboxylate}

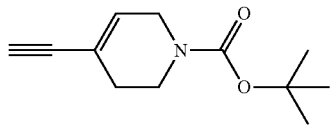

Step 1: Synthesis of tert-butyl 4-hydroxy-4-((trimethylsilyl)ethynyl)piperidine-1-carboxylate

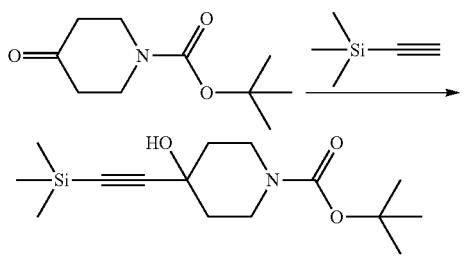

To a solution of tert-butyl 4-oxopiperidine-1-carboxylate (20 g, 1 eq) in THF (335 ml) was added with n-BuLi (2.5M, 64 ml, 1.6 eq) at −78° C. The mixture was stirred for 1 hr. A solution of ethynyltrimethylsilane (14.8 g, 1.5 eq) in THF (335 ml) was slowly added at −78° C. and stirred for 12 hr at room temperature. The mixture was quenched with water and extracted with ethyl acetate. The organic layer was washed with brine, dried over anhydrous MgSO₄ and concentrated in vacuo. The residue was purified with column chromatography to prepare the title compound (9 g, 30%).

¹H NMR (600 MHz, CDCl₃-d1); δ 3.82-3.76 (m, 2H), 3.22-3.18 (m, 2H), 2.08 (bs, 1H), 1.88-1.80 (m, 2H), 1.68-1.62 (m, 2H), 1.44 (s, 9H), 0.16 (s, 9H).

Step 2: Synthesis of tert-butyl 4-((trimethylsilyl)ethynyl)-3,6-dihydropyridine-1(2H)-carboxylate

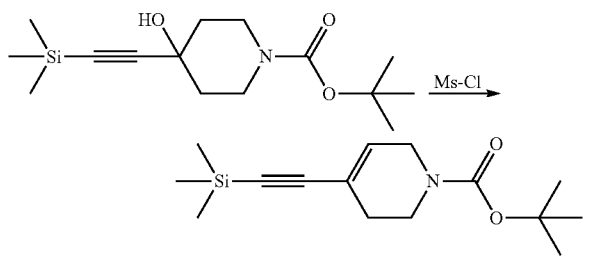

To a solution of tert-butyl 4-hydroxy-4-((trimethylsilyl)ethynyl)piperidine-1-carboxylate (5.8 g, 1 eq) in dichloromethane (195 ml) was added with Et₃N (5.44 ml, 2 eq) and methanesulfonyl chloride (3.04 ml, 2 eq) at −10° C. The mixture was stirred for 12 hr at room temperature and then extracted with dichloromethane and water. The organic layer was washed with brine, dried over anhydrous MgSO₄ and concentrated in vacuo. The residue was purified with column chromatography to prepare the title compound (3.3 g, 61%).

¹H NMR (600 MHz, CDCl₃-d1); δ 6.04 (s, 1H), 3.96-3.90 (m, 2H), 3.50-3.42 (m, 2H), 2.28-2.18 (m, 2H), 1.45 (s, 9H), 0.17 (s, 9H).

Step 3: Synthesis of tert-butyl 4-ethynyl-3,6-dihydropyridine-1(2H)-carboxylate

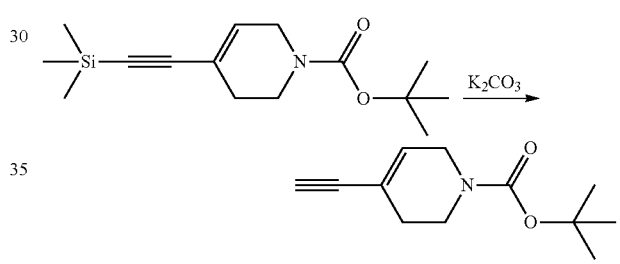

To a solution of tert-butyl 4-((trimethylsilyl)ethynyl)-3,6-dihydropyridine-1(2H)-carboxylate (3.3 g, 1 eq) in MeOH (100 ml) was added with K₂CO₃ (2.45 g, 1.5 eq). The mixture was stirred for 4 hr at room temperature, and extracted with ethyl acetate and water. The organic layer was dried over anhydrous MgSO₄ and concentrated in vacuo. The residue was purified with column chromatography to prepare the title compound (2.38 g, 97%).

¹H NMR (600 MHz, CDCl₃-d1); δ 6.08 (s, 1H), 3.96-3.90 (m, 2H), 3.50-3.42 (m, 2H), 2.88 (s, 1H), 2.28-2.18 (m, 2H), 1.45 (s, 9H).

Example 52: Synthesis of N-hydroxy-2-methyl-2-(methylsulfonyl)-4-(4-(pyridin-4-ylethynyl)-3,6-dihydropyridin-1(2H)-yl)butanamide

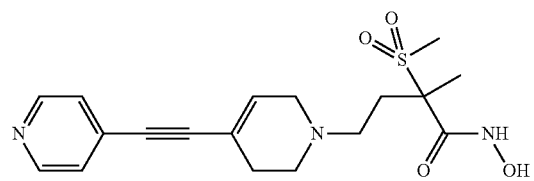 [SMILES: CC(CCN1CC=C(C#Cc2ccncc2)CC1)(C(=O)NO)S(C)(=O)=O]

Step 1: Synthesis of tert-butyl 4-(pyridin-4-ylethynyl)-3,6-dihydropyridine-1(2H)-carboxylate To a solution of tert-butyl 4-ethynyl-3,6-dihydropyridine-1(2H)-carboxylate (Intermediate 7) (900 mg, 1 eq) in THF (10 ml) was added with CuI (83 mg, 0.1 eq), Pd(PPh$_3$)$_2$Cl$_2$ (152 mg, 0.05 eq), Et3N (2.4 ml, 4 eq) and 4-iodopyridine (890 mg, 1 eq). The mixture was stirred for 2 days at room temperature, and extracted with ethyl acetate and water. The organic layer was dried over anhydrous MgSO$_4$ and concentrated in vacuo. The residue was purified with column chromatography to prepare the title compound (500 mg, 41%).

$^1$H NMR (600 MHz, CDCl$_3$-d1); δ 8.90-8.56 (m, 2H), 7.58-7.34 (m, 2H), 6.20 (s, 1H), 4.08-4.00 (m, 2H), 3.56-3.50 (m, 2H), 2.48-2.40 (m, 2H), 1.47 (s, 9H).

Step 2: Synthesis of 4-((1,2,3,6-tetrahydropyridin-4-yl)ethynyl)pyridine hydrochloride To a solution of tert-butyl 4-(pyridin-4-ylethynyl)-3,6-dihydropyridine-1(2H)-carboxylate (500 mg, 1 eq) in MeOH (10 ml) was added with acetyl chloride (1.25 ml, 10 eq). The mixture was stirred for 4 hr at 60° C., cooled down to room temperature and concentrated in vacuo to prepare the title compound (380 mg, 98%).

$^1$H NMR (600 MHz, CD$_3$OD-d4); δ 8.84-8.82 (m, 2H), 8.08-8.07 (m, 2H), 6.52 (m, 1H), 3.90-3.88 (m, 2H), 3.43-3.41 (m, 2H), 2.68-2.66 (m, 2H).

Step 3: Synthesis of methyl 2-methyl-2-(methylsulfonyl)-4-(4-(pyridin-4-ylethynyl)-3,6-dihydropyridin-1(2H)-yl)butanoate To a solution of 4-((1,2,3,6-tetrahydropyridin-4-yl)ethynyl)pyridine hydrochloride (380 mg, 1 eq) in DMF (10 ml) wad added with N,N-diisopropylethylamine (1.2 ml, 4 eq) and methyl 4-bromo-2-methyl-2-(methylsulfonyl)butanoate (Intermediate 1) (940 mg, 2 eq). The mixture was stirred for 12 hr at 60° C., cooled down to room temperature, and extracted with ethyl acetate and water. The organic layer was washed with brine, dried over anhydrous MgSO$_4$ and concentrated in vacuo. The residue was purified with column chromatography to prepare the title compound (85 mg, 13%).

$^1$H NMR (600 MHz, CDCl$_3$-d1); δ 8.54-8.53 (m, 2H), 7.26-7.25 (m, 2H), 6.16 (s, 1H), 3.74 (s, 3H), 3.18-3.14 (m, 1H), 3.03 (s, 3H), 2.98-2.94 (m, 1H), 2.72-2.46 (m, 4H), 2.32-2.28 (m, 2H), 1.88-1.82 (m, 1H), 1.61 (s, 3H), 1.29-1.24 (m, 1H).

MS (ESI, m/z): 377.1 [M+H]$^+$.

Step 4-6: Synthesis of N-hydroxy-2-methyl-2-(methylsulfonyl)-4-(4-(pyridin-4-ylethynyl)-3,6-dihydropyridin-1(2H)-yl)butanamide The title compound was prepared the procedures described for the synthesis of Example 1, step 2-4 (Synthesis of Hydroxamate) from methyl 2-methyl-2-(methylsulfonyl)-4-(4-(pyridin-4-ylethynyl)-3,6-dihydropyridin-1(2H)-yl)butanoate.

$^1$H NMR (600 MHz, DMSO-d6); δ10.93 (bs, 1H), 9.10 (bs, 1H), 8.55-8.53 (m, 2H), 7.37-7.36 (m, 2H), 6.23 (s, 1H), 3.10-3.04 (m, 2H), 3.03 (s, 3H), 2.60-2.54 (m, 2H), 2.48-2.42 (m, 2H), 2.36-2.18 (m, 3H), 1.82-1.76 (m, 1H), 1.43 (s, 3H).

MS (ESI, m/z): 378.1 [M+H]$^+$.

Example 53: Synthesis of 4-(4-((4-bromophenyl)ethynyl)-3,6-dihydropyridin-1(2H)-yl)-N-hydroxy-2-methyl-2-(methylsulfonyl)butanamide

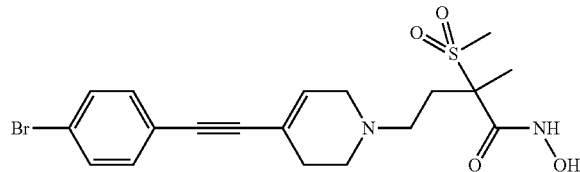 [SMILES: CC(CCN1CC=C(C#Cc2ccc(Br)cc2)CC1)(C(=O)NO)S(C)(=O)=O]

The title compound was prepared the procedures described for the synthesis of Example 52 using 1-bromo-4-iodobenzene.

$^1$H NMR (600 MHz, DMSO-d6); δ10.94 (bs, 1H), 9.10 (bs, 1H), 7.55-7.54 (m, 2H), 7.35-7.34 (m, 2H), 6.14 (s, 1H), 3.06-2.98 (m, 5H), 2.58-2.43 (m, 4H), 2.32-2.16 (m, 3H), 1.80-1.72 (m, 1H), 1.48 (s, 3H).

MS (ESI, m/z): 454.9 [M+H]$^+$.

Example 54: Synthesis of N-hydroxy-4-(4-(7-hydroxyhepta-1,3-diyn-1-yl)-3,6-dihydropyridin-1(2H)-yl)-2-methyl-2-(methylsulfonyl)butanamide

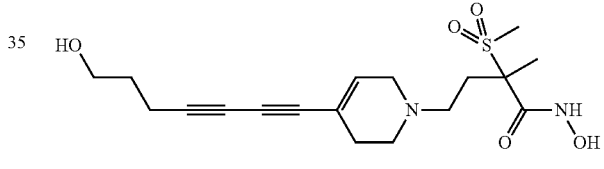

Step 1: Synthesis of tert-butyl 4-(7-hydroxyhepta-1,3-diyn-1-yl)-3,6-dihydropyridine-1(2H)-carboxylate To a solution of tert-butyl 4-ethynyl-3,6-dihydropyridine-1(2H)-carboxylate (5 g, 1 eq) in a mixture of MeOH (60 ml)/pyridine (60 ml) was added with Copper (II) acetate (8.76 g, 2 eq) and pent-4-yn-1-ol (8.12 g, 4 eq). The mixture was stirred for 24 hr at room temperature, and extracted with ethyl acetate and water. The organic layer was dried over anhydrous MgSO$_4$ and concentrated in vacuo. The residue was purified with column chromatography to prepare the title compound (1.8 g, 26%).

$^1$H NMR (600 MHz, CDCl$_3$-d1); δ 6.12 (s, 1H), 3.96-3.94 (m, 2H), 3.76-3.73 (m, 2H), 3.48-3.44 (m, 2H), 2.47-2.44 (m, 2H), 2.22-2.20 (m, 2H), 1.82-1.76 (m, 2H), 1.45 (s, 9H).

Step 2: Synthesis of 7-(1,2,3,6-tetrahydropyridin-4-yl)hepta-4,6-diyn-1-ol hydrochloride To a solution of tert-butyl 4-(7-hydroxyhepta-1,3-diyn-1-yl)-3,6-dihydropyridine-1(2H)-carboxylate (1.8 g, 1 eq) in MeOH (30 ml) was added with acetyl chloride (4.42 ml, 10 eq). The mixture was stirred for 4 hr at 60° C., cooled down to room temperature and diluted in diethyl ether. The precipitated solid was filtered off to prepare the title compound (1 g, 71%).

¹H NMR (600 MHz, CDCl₃-d1); δ 6.17 (m, 1H), 3.76-3.74 (m, 2H), 3.62-3.59 (m, 2H), 3.33-3.29 (m, 2H), 2.48-2.46 (m, 2H), 2.44-2.42 (m, 2H), 1.75-1.70 (m, 2H).

Step 3: Synthesis of methyl 4-(4-(7-hydroxyhepta-1,3-diyn-1-yl)-3,6-dihydropyridin-1(2H)-yl)-2-methyl-2-(methylsulfonyl)butanoate To a solution of 7-(1,2,3,6-tetrahydropyridin-4-yl)hepta-4,6-diyn-1-ol hydrochloride (900 mg, 1 eq) in DMF (20 ml) wad added with N,N-diisopropylethylamine (2.79 ml, 4 eq) and methyl 4-bromo-2-methyl-2-(methylsulfonyl)butanoate (Intermediate 1) (2.18 g, 2 eq). The mixture was stirred for 12 hr at 60° C., cooled down to room temperature, and extracted with ethyl acetate and water. The organic layer was washed with brine, dried over anhydrous MgSO₄ and concentrated in vacuo. The residue was purified with column chromatography to prepare the title compound (300 mg, 19.8%).
MS (ESI, m/z): 382.2 [M+H]⁺.

Step 4-6: Synthesis of N-hydroxy-4-(4-(7-hydroxy-hepta-1,3-diyn-1-yl)-3,6-dihydropyridin-1(2H)-yl)-2-methyl-2-(methylsulfonyl)butanamide The title compound was prepared the procedures described for the synthesis of Example 1, step 2-4 (Synthesis of Hydroxamate) from methyl 4-(4-(7-hydroxyhepta-1,3-diyn-1-yl)-3,6-dihydropyridin-1(2H)-yl)-2-methyl-2-(methylsulfonyl)butanoate.
¹H NMR (600 MHz, DMSO-d6); δ10.90 (bs, 1H), 9.09 (bs, 1H), 6.19 (s, 1H), 4.53 (t, J=5.4 Hz, 1H), 3.43-3.40 (m, 2H), 3.02 (s, 3H), 2.93-2.99 (m, 2H), 2.52-2.50 (m, 1H), 2.44-2.36 (m, 5H), 2.27-2.24 (m, 1H), 2.16-2.07 (m, 2H), 1.77-1.73 (m, 1H), 1.61-1.56 (m, 2H), 1.41 (s, 3H).
MS (ESI, m/z): 383.1 [M+H]⁺.

Example 55: Synthesis of N-hydroxy-2-methyl-2-(methylsulfonyl)-4-(4-(4-(pyridin-4-yl)phenyl)-3,6-dihydropyridin-1(2H)-yl)butanamide

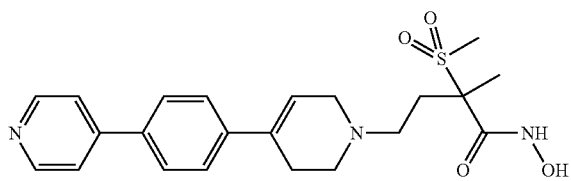 [SMILES: CC(CCN1CC=C(c2ccc(-c3ccncc3)cc2)CC1)(C(=O)NO)S(C)(=O)=O]

Step 1: Synthesis of methyl 2-methyl-2-(methylsulfonyl)-4-(4-(4-(pyridin-4-yl)phenyl)-3,6-dihydropyridin-1(2H)-yl)butanoate To a solution of methyl 4-(4-(4-iodophenyl)-3,6-dihydropyridin-1(2H)-yl)-2-methyl-2-(methylsulfonyl)butanoate (Intermediate 2) (1.27 g. 1 eq) in a mixture of 1,4-dioxane (12 ml)/water (3 ml) was added with Pd(PPh₃)₂Cl₂(0.21 g, 0.1 eq), K₂CO₃(1.27 g, 3 eq) and pyridin-4-ylboronic acid (0.75 g, 2 eq). The mixture was stirred for 2 hr at 110° C., cooled down to room temperature, and extracted with ethyl acetate and water. The organic layer was washed with brine, dried over anhydrous MgSO₄ and concentrated in vacuo. The residue was purified with column chromatography to prepare the title compound (536 mg, 41%).

¹H NMR (600 MHz, CDCl₃-d1); δ8.65 (d, J=6 Hz, 2H), 7.61 (d, J=8.4 Hz, 2H), 7.51-7.49 (m, 4H), 6.16 (s, 1H), 3.70 (s, 3H), 3.28-3.25 (m, 1H), 3.09-3.07 (m, 1H), 3.06 (s, 3H), 2.84-2.82 (m, 1H), 2.70-2.55 (m, 6H), 2.04-2.02 (m, 1H), 2.65 (s, 3H).
MS (ESI, m/z): 429.1 [M+H]⁺.

Step 2: Synthesis of 2-methyl-2-(methylsulfonyl)-4-(4-(4-(pyridin-4-yl)phenyl)-3,6-dihydropyridin-1(2H)-yl)butanoic acid To a solution methyl 2-methyl-2-(methylsulfonyl)-4-(4-(4-(pyridin-4-yl)phenyl)-3,6-dihydropyridin-1(2H)-yl)butanoate (536 mg, 1 eq) in a mixture of THF (8 ml)/MeOH (2 ml) was added with 2N—LiOH (1.88 mL, 3 eq) solution. The mixture was stirred for 2 hr at room temperature. The solvent was removed under reduced pressure. The residue was diluted with water (10 ml) and adjusted the pH to 4.0. The precipitated solid was filtered off to prepare the title compound (476 mg, 92%), which was used for next step without further purification.
MS (ESI, m/z): 415.2 [M+H]⁺.

Step 3: Synthesis of 2-methyl-2-(methylsulfonyl)-4-(4-(4-(pyridin-4-yl)phenyl)-3,6-dihydropyridin-1(2H)-yl)-N-((tetrahydro-2H-pyran-2-yl)oxy)butanamide To a solution of of 2-methyl-2-(methylsulfonyl)-4-(4-(4-(pyridin-4-yl)phenyl)-3,6-dihydropyridin-1(2H)-yl)butanoic acid (476 mg, 1 eq) in DMF (10 ml) was added with HATU (611 mg, 1.4 eq), HOBT (246 mg, 1.4 eq), Et₃N (0.48 ml, 3 eq) and O-(tetrahydro-2H-pyran-2-yl)hydroxylamine hydrochloride (353 mg, 2 eq). The mixture was stirred for 1 hr at room temperature, and extracted with ethyl acetate and water. The organic layer was washed with brine, dried over anhydrous MgSO₄ and concentrated in vacuo. The residue was purified with column chromatography to prepare the title compound (400 mg, 68%).
MS (ESI, m/z): 514.3 [M+H]⁺.

Step 4: Synthesis of N-hydroxy-2-methyl-2-(methylsulfonyl)-4-(4-(4-(pyridin-4-yl)phenyl)-3,6-dihydropyridin-1(2H)-yl)butanamide To a solution of 2-methyl-2-(methylsulfonyl)-4-(4-(4-(pyridin-4-yl)phenyl)-3,6-dihydropyridin-1(2H)-yl)-N-((tetrahydro-2H-pyran-2-yl)oxy)butanamide (400 mg, 1 eq) in MeOH (10 ml) was added with HCl solution in MeOH (1.25N, 1.87 ml, 3 eq). The mixture was stirred for 2 hr at room temperature. The solvent was removed under reduced pressure. The residue was diluted with water (6 ml) and adjusted the pH to 7.0. The water was concentrated in vacuo and the resulting residue was purified with column chromatography to prepare the title compound (91 mg, 27%).
¹H NMR (600 MHz, DMSO-d6); δ 11.02 (bs, 1H), 9.11 (bs, 1H), 8.59 (d, J=6 Hz, 2H), 7.76 (d, J=8.4 Hz, 2H), 7.69 (dd, J=4.8 Hz, 1.8 Hz, 2H), 7.55 (d, J=7.8 Hz, 2H), 6.26 (s, 1H), 3.14-3.09 (m, 2H), 3.05 (s, 3H), 2.67-2.58 (m, 2H), 2.52-2.44 (m, 4H), 2.36-2.30 (m, 1H), 1.84-1.80 (m, 1H), 1.45 (s, 3H).
MS (ESI, m/z): 430.1 [M+H]⁺.

Examples 56-73

The Intermediate 2 as a starting material and boronic acid derivatives listed in the following table were used to prepare compounds of Examples 56-73 in the same manner as Example 55.

| Example | Structure (Name) | Boronic acid |
|---|---|---|
| | 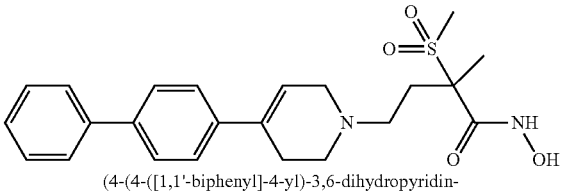<br>(4-(4-([1,1'-biphenyl]-4-yl)-3,6-dihydropyridin-1(2H)-yl)-N-hydroxy-2-methyl-2-(methylsulfonyl)butanamide)<br>¹H NMR (600 MHz, DMSO-d6); δ 11.02 (bs, 1H), 9.10 (bs, 1H), 7.68-7.60 (m, 4H), 7.50-7.48 (m, 2H), 7.45-7.41 (m, 2H), 7.33-7.31 (m, 1H), 6.19 (s, 1H), 3.34-3.28 (m, 6H), 3.15-3.07 (m, 2H), 3.04 (s, 3H), 2.64-2.58 (m, 2H), 1.45 (s, 3H).<br>MS (ESI, m/z): 429.2 [M + H]⁺. | |
| 57 | 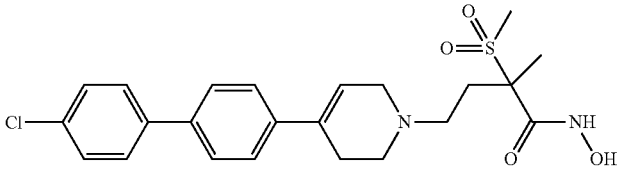 [SMILES: CC(CCN1CC=C(c2ccc(-c3ccc(Cl)cc3)cc2)CC1)(C(=O)NO)S(C)(=O)=O]<br>(4-(4-(4'-chloro-[1,1'-biphenyl]-4-yl)-3,6-dihydropyridin-1(2H)-yl)-N-hydroxy-2-methyl-2-(methylsulfonyl)butanamide)<br>¹H NMR (600 MHz, DMSO-d6); δ 11.02 (bs, 1H), 9.10 (bs, 2H), 7.69-7.66 (m, 2H), 7.62-7.59 (m, 2H), 7.50-7.46 (m, 4H), 6.20 (s, 1H), 3.11-3.08 (m, 2H), 3.04 (s, 3H), 2.65-2.58 (m, 3H), 2.53-2.42 (m, 3H), 2.32-2.28 (m, 1H), 1.85-1.81 (m, 1H), 1.44 (s, 3H).<br>MS (ESI, m/z): 463.1 [M + H]⁺. | 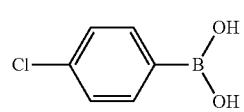 |
| | 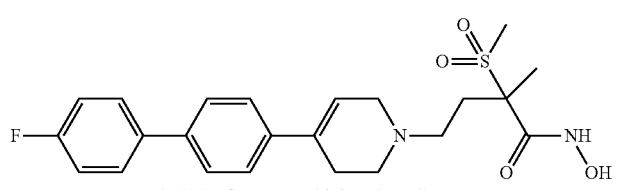<br>(4-(4-(4'-fluoro-[1,1'-biphenyl]-4-yl)-3,6-dihydropyridin-1(2H)-yl)-N-hydroxy-2-methyl-2-(methylsulfonyl)butanamide)<br>¹H NMR (600 MHz, DMSO-d6); δ 11.01 (bs, 1H), 9.10 (bs, 1H), 7.70-7.67 (m, 2H), 7.59-7.58 (m, 2H), 7.49-7.48 (m, 2H), 7.27-7.23 (m, 2H), 6.19 (s, 1H), 3.13-3.05 (m, 2H), 3.04 (s, 3H), 2.66-2.58 (m, 2H), 2.53-2.42 (m, 4H), 2.35-2.28 (m, 2H), 1.45 (s, 3H).<br>MS (ESI, m/z): 447.0 [M + H]⁺. | |
| | 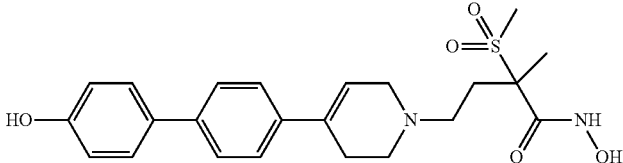<br>(N-hydroxy-4-(4-(4'-hydroxy-[1,1'-biphenyl]-4-yl)-3,6-dihydropyridin-1(2H)-yl)-2-methyl-2-(methylsulfonyl)butanamide)<br>¹H NMR (600 MHz, DMSO-d6); δ 11.04 (bs, 1H), 10.8 (bs, 1H), 7.60-7.48 (m, 6H), 6.84-6.82 (m, 2H), 6.21 (s, 1H), 4.10-4.00 (m, 2H), 3.99-3.63 (m, 2H), 3.10 (s, 3H), 2.66-2.64 (m, 4H), 2.29-2.21 (m, 2H), 1.53 (s, 3H).<br>MS (ESI, m/z): 445.1 [M + H]⁺. | |

| Example | Structure (Name) | Boronic acid |
|---|---|---|
| | 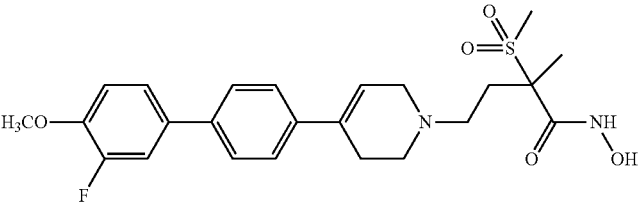 [SMILES: COc1ccc(-c2ccc(C3=CCN(CCC(C)(C(=O)NO)S(C)(=O)=O)CC3)cc2)cc1F]
(4-(4-(3'-fluoro-4'-methoxy-[1,1'-biphenyl]-4-yl)-3,6-dihydropyridin-1(2H)-yl)-N-hydroxy-2-methyl-2-(methylsulfonyl)butanamide)
¹H NMR (600 MHz, DMSO-d6); δ 11.03 (bs, 1H), 9.10 (bs, 1H), 7.60-7.44 (m, 6H), 7.22-7.19 (m, 1H), 6.18 (s, 1H), 3.84 (s, 3H), 3.10-3.08 (m, 2H), 3.04 (s, 3H), 2.66-2.57 (m, 2H), 2.50-2.42 (m, 4H), 2.34-2.30 (m, 1H), 1.84-1.80 (m, 1H), 1.45 (s, 3H).
MS (ESI, m/z): 477.2 [M + H]⁺. | |
| | 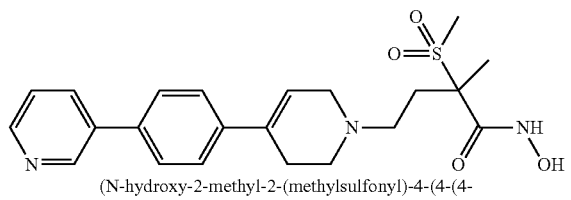
(N-hydroxy-2-methyl-2-(methylsulfonyl)-4-(4-(4-(pyridin-3-yl)phenyl)-3,6-dihydropyridin-1(2H)-yl)butanamide)
¹H NMR (600 MHz, DMSO-d6); δ 11.00 (bs, 1H), 9.12 (bs, 1H), 8.87 (s, 1H), 8.53-8.52 (m, 1H), 8.05-8.04 (m, 1H), 7.68-7.67 (m, 2H), 7.45-7.44 (m, 2H), 7.45-7.44 (m, 1H), 6.22 (s, 1H), 3.10-3.08 (m, 4H), 3.05 (s, 3H), 2.72-2.69 (m, 2H), 2.58-2.35 (m, 4H), 1.45 (s, 3H).
MS (ESI, m/z): 430.1 [M + H]⁺. | |
| 62 | 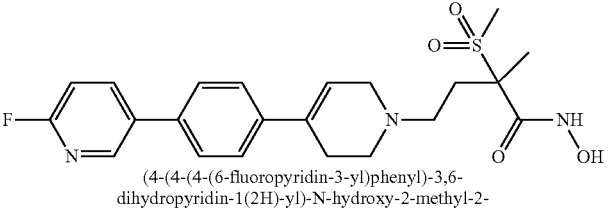
(4-(4-(4-(6-fluoropyridin-3-yl)phenyl)-3,6-dihydropyridin-1(2H)-yl)-N-hydroxy-2-methyl-2-(methylsulfonyl)butanamide)
¹H NMR (600 MHz, DMSO-d6); δ 11.00 (bs, 1H), 9.11 (bs, 1H), 8.54-8.53 (m, 1H), 8.29 (m, 1H), 7.68-7.66 (m, 2H), 7.54-7.50 (m, 2H), 7.27-7.24 (m, 1H), 6.23 (s, 1H), 3.27-3.26 (m, 4H), 3.16-3.09 (m, 2H), 3.05 (s, 3H), 2.67-2.57 (m, 2H), 2.35-2.30 (m, 2H), 1.45 (s, 3H).
MS (ESI, m/z): 448.0 [M + H]⁺. | 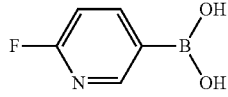 |
| | 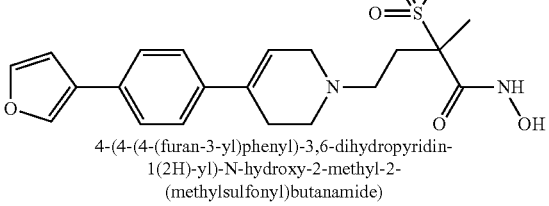
4-(4-(4-(furan-3-yl)phenyl)-3,6-dihydropyridin-1(2H)-yl)-N-hydroxy-2-methyl-2-(methylsulfonyl)butanamide)
1H NMR (600 MHz, DMSO-d6) δ; 11.02 (bs, 1H), 9.08 (bs, 1H), 8.15 (s, 1H), 7.71-7.70 (m, 1H), 7.53-7.51 (m, 2H), 7.42-7.40 (m, 2H), 6.93 (s, 1H), 6.16 (s, 1H), 3.15-3.06 (m, 2H), 3.04 (s, 3H), 2.68-2.54 (m, 3H), 2.44-2.30 (m, 4H), 1.86-1.80 (m, 1H), 1.45 (s, 3H).
MS (ESI, m/z): 419.2 [M + H]⁺. | |

-continued

| Example | Structure (Name) | Boronic acid |
|---|---|---|
| | 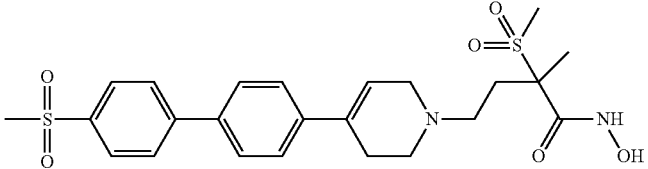 [SMILES: CC(CCN1CC=C(c2ccc(-c3ccc(S(C)(=O)=O)cc3)cc2)CC1)(C(=O)NO)S(C)(=O)=O]<br>(N-hydroxy-2-methyl-2-(methylsulfonyl)-4-(4-(4'-(methylsulfonyl)-[1,1'-biphenyl]-4-yl)-3,6-dihydropyridin-1(2H)-yl)butanamide)<br>$^1$H NMR (600 MHz, DMSO-d6); δ 11.01 (bs, 1H), 9.10 (bs, 1H), 7.98-7.93 (m, 4H), 7.72-7.70 (m, 2H), 7.55-7.54 (m, 2H), 6.24 (s, 1H), 3.25 (s, 3H), 3.07-3.06 (m, 4H), 3.04 (s, 3H), 2.66-2.59 (m, 4H), 2.35-2.31 (m, 2H), 1.45 (s, 3H).<br>MS (ESI, m/z): 506.9 [M + H]$^+$. | |
| | 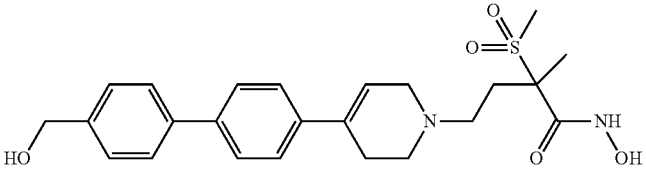 [SMILES: CC(CCN1CC=C(c2ccc(-c3ccc(CO)cc3)cc2)CC1)(C(=O)NO)S(C)(=O)=O]<br>(N-hydroxy-4-(4-(4'-(hydroxymethyl)-[1,1'-biphenyl]-4-yl)-3,6-dihydropyridin-1(2H)-yl)-2-methyl-2-(methylsulfonyl)butanamide)<br>$^1$H NMR (600 MHz, DMSO-d6); δ 11.03 (bs, 1H), 9.12 (bs, 1H), 7.61-7.60 (m, 4H), 7.49-7.48 (m, 2H), 7.37-7.36 (m, 2H), 6.19 (s, 1H), 5.20-5.18 (m, 1H), 4.51-4.50 (m, 2H), 3.16-3.06 (m, 2H), 3.05 (s, 3H), 2.74-2.52 (m, 3H), 2.48-2.38 (m, 4H), 1.86-1.80 (m, 1H), 1.46 (s, 3H).<br>MS (ESI, m/z): 459.2 [M + H]$^+$. | |
| | 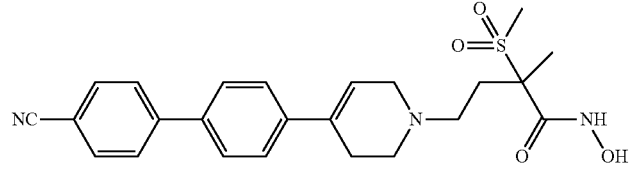<br>(4-(4-(4'-cyano-[1,1'-biphenyl]-4-yl)-3,6-dihydropyridin-1(2H)-yl)-N-hydroxy-2-methyl-2-(methylsulfonyl)butanamide)<br>$^1$H NMR (600 MHz, DMSO-d6); δ 11.02 (bs, 1H), 9.12 (bs, 1H), 7.92-7.86 (m, 4H), 7.71 (d, J = 14.4 Hz, 2H), 7.54 (d, J = 8.4 Hz, 2H), 6.25 (s, 1H), 3.16-3.06 (m, 2H), 3.05 (s, 3H), 2.66-2.57 (m, 2H), 2.54-2.46 (m, 4H), 2.36-2.33 (m, 1H), 1.87-1.83 (m, 1H), 1.45 (s, 3H).<br>MS (ESI, m/z): 454.1 [M + H]$^+$. | |
| 67 | 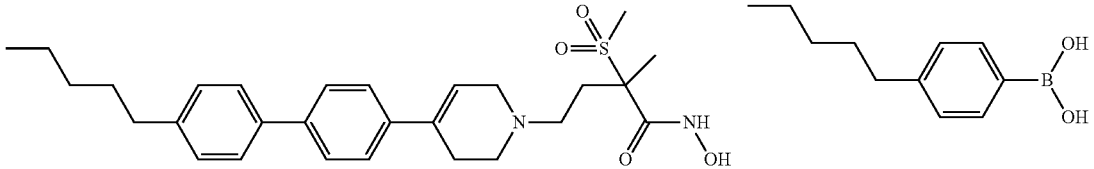<br>(N-hydroxy-2-methyl-2-(methylsulfonyl)-4-(4-(4'-pentyl-[1,1'-biphenyl]-4-yl)-3,6-dihydropyridin-1(2H)-yl)butanamide)<br>$^1$H NMR (600 MHz, DMSO-d6); δ 11.03 (bs, 1H), 9.12 (bs, 1H), 7.58 (d, J = 9.0 Hz, 2H), 7.54 (d, J = 8.4 Hz, 2H), 7.46 (d, J = 9.0 Hz, 2H), 7.23 (d, J = 7.2 Hz, 2H), 6.18 (s, 1H), 3.10-3.07 (m, 2H), 3.04 (s 3H), 2.65-2.53 (m, 4H), 2.46-2.42 (m, | 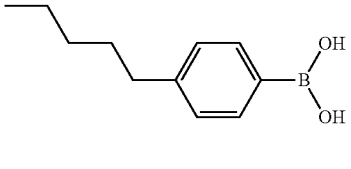 |

2H), 2.35-2.28 (m, 1H), 1.87-1.80 (m, 1H), 1.58-1.53 (m, 3H), 1.44 (s, 3H), 1.31-1.18 (m, 5H), 0.85-0.81 (m, 3H).
MS (ESI, m/z): 499.2 [M + H]⁺.

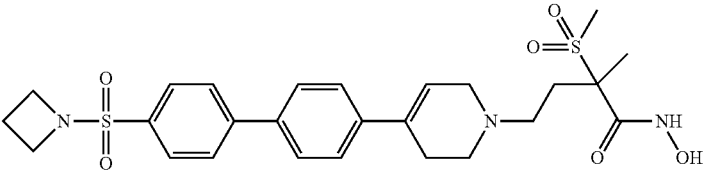 [SMILES: CC(CCN1CC=C(c2ccc(-c3ccc(S(=O)(=O)N4CCC4)cc3)cc2)CC1)(C(=O)NO)S(C)(=O)=O]

(4-(4-(4'-(azetidin-1-ylsulfonyl)-[1,1'-biphenyl]-4-yl)-3,6-dihydropyridin-1(2H)-yl)-N-hydroxy-2-methyl-2-(methylsulfonyl)butanamide)
¹H NMR (600 MHz, DMSO-d6); δ 11.03 (bs, 1H), 9.12 (bs, 1H), 7.98-7.97 (m, 2H), 7.84-7.83 (m, 2H), 7.75-7.74 (m, 2H), 7.57-7.56 (m, 2H), 6.26 (s, 1H), 3.68-3.66 (m, 4H), 3.31-3.30 (m, 2H), 3.13-3.11 (m, 2H), 3.05 (s, 3H), 2.65-2.59 (m, 2H), 2.36-2.32 (m, 2H), 2.01-1.96 (m, 2H), 1.84-1.82 (m, 2H), 1.45 (s, 3H).
MS (ESI, m/z): 548.2 [M + H]⁺.

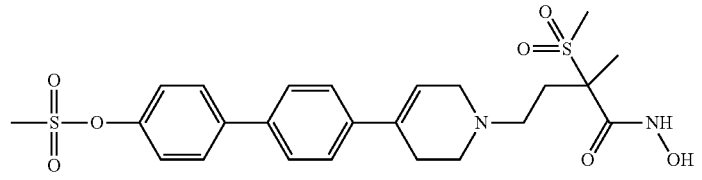 [SMILES: CC(CCN1CC=C(c2ccc(-c3ccc(OS(C)(=O)=O)cc3)cc2)CC1)(C(=O)NO)S(C)(=O)=O]

(4'-(1-(4-(hydroxyamino)-3-methyl-3-(methylsulfonyl)-4-oxobutyl)-1,2,3,6-tetrahydropyridin-4-yl)-[1,1'-biphenyl]-4-yl methanesulfonate)
¹H NMR (600 MHz, DMSO-d6); δ 11.02 (bs, 1H), 9.11 (bs, 1H), 7.97-7.92 (m, 4H), 7.22-7.71 (m, 2H), 7.56-7.54 (m, 2H), 6.25 (s, 1H), 3.28 (s, 3H), 3.13-3.09 (m, 4H), 3.05 (s, 3H), 2.66-2.59 (m, 2H), 2.45-2.31 (m, 2H), 1.85-1.82 (m, 2H), 1.45 (s, 3H).
MS (ESI, m/z): 506.9 [M + H]⁺.

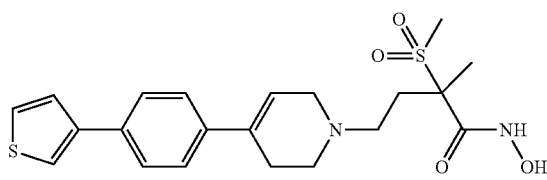 [SMILES: CC(CCN1CC=C(c2ccc(-c3ccsc3)cc2)CC1)(C(=O)NO)S(C)(=O)=O]

(N-hydroxy-2-methyl-2-(methylsulfonyl)-4-(4-(4-(thiophen-3-yl)phenyl)-3,6-dihydropyridin-1(2H)-yl)butanamide)
¹H NMR (600 MHz, DMSO-d6); δ 11.05 (bs, 1H), 9.13 (bs, 1H), 7.87 (s, 1H), 7.68-7.67 (m, 2H), 7.63-7.62 (m, 1H), 7.56-7.55 (m, 1H), 7.46-7.45 (m, 2H), 6.20 (s, 1H), 3.15-3.08 (m, 2H), 3.01 (s, 3H), 2.64-2.60 (m, 2H), 2.49-2.32 (m, 5H), 1.85-1.83 (m, 1H), 1.47 (s, 3H).
MS (ESI, m/z): 435.2 [M + H]⁺.

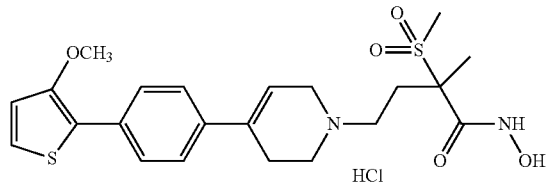 [SMILES: COc1ccsc1-c1ccc(C2=CCN(CCC(C)(C(=O)NO)S(C)(=O)=O)CC2)cc1 ; Cl]

HCl
(N-hydroxy-4-(4-(4-(3-methoxythiophen-2-yl)phenyl)-3,6-dihydropyridin-1(2H)-yl)-2-methyl-2-(methylsulfonyl)butanamide

| Example | Structure (Name) | Boronic acid |
|---|---|---|
| | hydrochloride)<br>¹H NMR (600 MHz, DMSO-d6); δ 11.06 (bs, 1H), 11.11-11.00 (m, 1H), 9.13 (bs, 1H), 7.68-7.67 (m, 2H), 7.51-7.49 (m, 3H), 7.15-7.14 (m, 1H), 6.22 (s, 1H), 4.03-3.97 (m, 2H), 3.90 (s, 3H), 3.77-3.74 (m, 2H), 3.35-3.31 (m, 2H), 3.12 (s, 3H), 3.02-2.85 (m, 2H), 2.74-2.69 (m, 2H), 1.53-1.52 (m, 3H).<br>MS (ESI, m/z): 465.1 [M + H]⁺. | |
| | 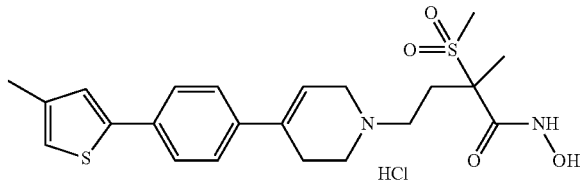 [SMILES: Cc1csc(-c2ccc(C3=CCN(CCC(C)(C(=O)NO)S(C)(=O)=O)CC3)cc2)c1 ; Cl]<br>(N-hydroxy-2-methyl-2-(methylsulfonyl)-4-(4-(4-(4-methylthiophen-2-yl)phenyl)-3,6-dihydropyridin-1(2H)-yl)butanamide hydrochloride)<br>¹H NMR (600 MHz, DMSO-d6); δ 11.06 (bs, 1H), 10.45-10.40 (m, 1H), 9.15 (bs, 1H), 7.63-7.62 (m, 2H), 7.53-7.52 (m, 2H), 7.38 (s, 1H), 7.13 (s, 1H), 6.26 (s, 1H), 4.23-3.70 (m, 2H), 3.42-3.31 (m, 5H), 3.11 (s, 3H), 3.01-2.69 (m, 3H), 2.23 (s, 3H), 1.53-1.52 (m, 3H)<br>MS (ESI, m/z): 449.1 [M + H]⁺. | |
| | 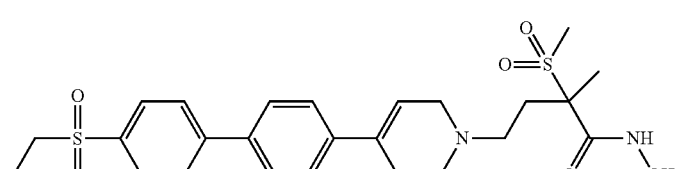<br>(4-(4-(4'-(ethylsulfonyl)-[1,1'-biphenyl]-4-yl)-3,6-dihydropyridin-1(2H)-yl)-N-hydroxy-2-methyl-2-(methylsulfonyl)butanamide hydrochloride)<br>¹H NMR (600 MHz, DMSO-d6); δ 11.06 (m,1H), 10.06 (bs, 1H), 9.31 (s, 1H), 7.99-7.95 (m, 4H), 7.82 (d, J = 7.8 Hz, 2H), 7.66 (d, J = 7.8 Hz, 2H), 6.34 (s, 1H), 4.18-4.06 (m, 1H), 3.92-3.70 (m, 2H), 3.11 (s, 3H), 3.08-3.02 (m, 1H), 2.86-2.82 (m, 2H), 2.72-2.54 (m, 2H), 2.22-2.14 (m, 2H), 2.02-1.98 (m, 2H), 1.52 (s, 3H), 1.12 (t, J = 7.2 Hz, 3H).<br>MS (ESI, m/z): 521.1 [M + H]⁺. | |

Example 74: Synthesis of N-hydroxy-2-methyl-2-(methylsulfonyl)-4-(4-(4'-(morpholinomethyl)-[1,1'-biphenyl]-4-yl)-3,6-dihydropyridin-1(2H)-yl)butanamide

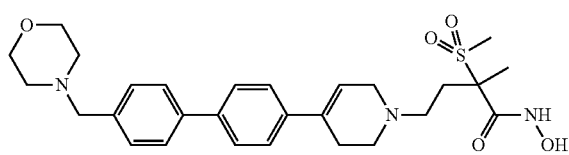 [SMILES: CC(CCN1CC=C(c2ccc(-c3ccc(CN4CCOCC4)cc3)cc2)CC1)(C(=O)NO)S(C)(=O)=O]

Step 1: Synthesis of methyl 4-(4-(4'-formyl-[1,1'-biphenyl]-4-yl)-3,6-dihydropyridin-1(2H)-yl)-2-methyl-2-(methylsulfonyl)butanoate To a solution of methyl 4-(4-(4-iodophenyl)-3,6-dihydropyridin-1(2H)-yl)-2-methyl-2-(methylsulfonyl)butanoate (Intermediate 2) (1.5 g, 1 eq) in a mixture of 1,4-dioxane (12 ml)/water (3 ml) was added with Pd(PPh₃)₂Cl₂(0.37 g, 0.1 eq), K₂CO₃(1.34 g, 3 eq) and (4-formylphenyl)boronic acid (0.97 g, 2 eq). The mixture was stirred for 2 hr at 110° C., cooled down to room temperature, and extracted with ethyl acetate and water. The organic layer was washed with brine, dried over anhydrous MgSO₄ and concentrated in vacuo. The residue was purified with column chromatography to prepare the title compound (1 g, 68%).

¹H NMR (600 MHz, CDCl₃-d1); δ10.04 (S, 1H), 7.94-7.92 (m, 2H), 7.74-7.71 (m, 2H), 7.63-7.60 (m, 2H), 7.49-7.45 (m, 2H), 6.08 (s, 1H), 3.87 (s, 3H), 3.79-76 (m, 2H), 3.66-3.56 (m, 2H), 3.42-3.26 (m, 2H), 3.13 (s, 3H), 2.92-2.72 (m, 4H), 1.74 (s, 3H).
MS (ESI, m/z): 456.2 [M+H]⁺.

Step 2: Synthesis of methyl 2-methyl-2-(methylsulfonyl)-4-(4-(4'-(morpholinomethyl)-[1,1'-biphenyl]-4-yl)-3,6-dihydropyridin-1(2H)-yl)butanoate To a solution of methyl 4-(4-(4'-formyl-[1,1'-biphenyl]-4-yl)-3,6-dihydropyridin-1(2H)-yl)-2-methyl-2-(methylsulfonyl)butanoate (500 mg, 1 eq) in THF (11 ml) was added with morpholine (0.19 ml, 2 eq) and sodium triacetoxyborohydride (930 mg, 4 eq). The mixture was stirred for 2 hr at room temperature, quenched with sat. aq. NaHCO₃, and extracted with dichloromethane and water. The organic layer was dried over anhydrous MgSO₄ and concentrated in vacuo. The residue was purified with column chromatography to prepare the title compound (450 mg, 78%).
¹H NMR (600 MHz, CDCl₃-d1); δ 7.55-7.53 (m, 4H), 7.44-7.43 (m, 2H), 7.40-7.38 (m, 2H), 6.11-6.10 (m, 1H), 3.74-3.72 (m, 4H), 3.69 (s, 3H), 3.55 (s, 2H), 3.28-3.24 (m, 1H), 3.10-3.02 (m, 1H), 3.05 (s, 3H), 2.86-2.78 (m, 1H), 2.68-2.58 (m, 4H), 2.56-2.46 (m, 6H), 2.06-1.98 (m, 1H), 1.64 (s, 3H).

Step 3-5: Synthesis of N-hydroxy-2-methyl-2-(methylsulfonyl)-4-(4-(4'-(morpholinomethyl)-[1,1'-biphenyl]-4-yl)-3,6-dihydropyridin-1(2H)-yl)butanamide The title compound was prepared the procedures described for the synthesis of Example 1, step 2-4 from methyl 2-methyl-2-(methylsulfonyl)-4-(4-(4'-(morpholinomethyl)-[1,1'-biphenyl]-4-yl)-3,6-dihydropyridin-1(2H)-yl)butanoate.
¹H NMR (600 MHz, DMSO-d6); δ11.01 (s, 1H), 9.12 (s, 1H), 7.61-7.60 (m, 4H), 7.50-7.48 (m, 2H), 7.37-7.35 (m, 2H), 6.20 (s, 1H), 3.56-3.55 (m, 4H), 3.10-3.08 (m, 2H), 3.05 (s, 3H), 2.66-2.59 (m, 2H), 2.51-2.43 (m, 4H), 2.37-2.30 (m, 5H), 1.84-1.80 (m, 1H), 1.45 (s, 3H).
MS (ESI, m/z): 528.25 [M+H]⁺.

Example 75: Synthesis of N-hydroxy-4-(6-(3-methoxyprop-1-yn-1-yl)-3',6'-dihydro-[3,4'-bipyridin]-1'(2'H)-yl)-2-methyl-2-(methylsulfonyl)butanamide

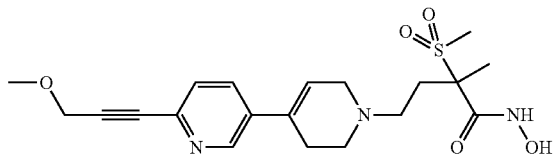 [SMILES: COCC#Cc1ccc(C2=CCN(CCC(C)(C(=O)NO)S(C)(=O)=O)CC2)cn1]

Step 1: Synthesis of 5-bromo-2-(3-methoxyprop-1-yn-1-yl)pyridine

To a solution of 2,5-dibromopyridine (5 g, 1 eq) in toluene (60 ml) was added with CuI (80 mg, 0.02 eq), Pd(PPh₃)₂Cl₂(150 mg, 0.01 eq), Et₃N (5.96 ml, 2 eq) and 3-methoxyprop-1-yne (1.6 g, 1.05 eq). The mixture was stirred for 24 hr at room temperature, and extracted with ethyl acetate and water. The organic layer was washed with brine, dried over anhydrous MgSO₄ and concentrated in vacuo. The residue was purified with column chromatography to prepare the title compound (4.3 g, 90%).
¹H NMR (600 MHz, CDCl₃-d1) δ; 8.62 (s, 1H), 7.78 (m, 1H), 7.73 (d, 1H), 4.32 (s, 2H), 3.45 (s, 3H). MS (ESI, m/z): 228.0 [M+H]⁺.

Step 2: Synthesis of tert-butyl 6-(3-methoxyprop-1-yn-1-yl)-3',6'-dihydro-[3,4'-bipyridine]-1' (2'H)-carboxylate To a solution of 5-bromo-2-(3-methoxyprop-1-yn-1-yl)pyridine (4.3 g, 1 eq) in a mixture of 1,4-dioxane (80 ml)/water (20 ml) was added with Pd(PPh₃)₂Cl₂(1.3 g, 0.1 eq), K₂CO₃ (5.3 g, 2 eq) and tert-butyl 4-(4,4,5,5-tetramethyl-1,3,2-dioxaborolan-2-yl)-3,6-dihydropyridine-1(2H)-carboxylate (7.7 g, 1.3 eq). The mixture was stirred for 2 hr at 110° C., cooled down to room temperature, and extracted with ethyl acetate and water. The organic layer was washed with brine, dried over anhydrous MgSO₄ and concentrated in vacuo. The residue was purified with column chromatography to prepare the title compound (2 g, 32%).
¹H NMR (600 MHz, CDCl₃-d1); δ7.64 (dd, 1H), 7.52 (m, 1H), 7.47 (m, 1H), 4.36 (s, 2H), 4.02 (m, 2H), 3.46-3.45, (m, 2H), 2.82 (m, 1H), 1.26 (s, 9H).
MS (ESI, m/z): 329.1 [M+H]⁺.

Step 3: Synthesis of 6-(3-methoxyprop-1-yn-1-yl)-1',2',3',6'-tetrahydro-3,4'-bipyridine 2,2,2-trifluoroacetate To a solution of tert-butyl 6-(3-methoxyprop-1-yn-1-yl)-3',6'-dihydro-[3,4'-bipyridine]-1'(2'H)-carboxylate (2 g, 1 eq) in dichloromethane (90 ml) was added with trifluoroacetic acid (50 ml, excess) at 0° C. The mixture was stirred for 2 hr at room temperature and concentrated in vacuo to prepare the title compound (2 g, 96%).
MS (ESI, m/z): 229.1 [M+H]⁺.

Step 4: Synthesis of methyl 4-(6-(3-methoxyprop-1-yn-1-yl)-3',6'-dihydro-[3,4'-bipyridin]-1' (2'H)-yl)-2-methyl-2-(methylsulfonyl)butanoate To a solution of 6-(3-methoxyprop-1-yn-1-yl)-1',2',3',6'-tetrahydro-3,4'-bipyridine 2,2,2-trifluoroacetate (1 g, 1 eq) in DMF (15 ml) was added with Et₃N (1.23 ml, 3 eq) and methyl 4-bromo-2-methyl-2-(methylsulfonyl)butanoate (Intermediate 1) (957 mg, 1.2 eq). The mixture was stirred for 12 hr at 60° C., cooled room temperature, and extracted with ethyl acetate and water. The organic layer was washed with brine, dried over anhydrous MgSO₄ and concentrated in vacuo. The residue was purified with column chromatography to prepare the title compound (1.1 g, 89%).
¹H NMR (600 MHz, CDCl₃-d1); δ7.62 (m, 1H), 7.95 (m, 1H), 7.66 (m, 1H), 6.15 (s, 1H), 4.33 (s, 2H), 3.67, (s, 3H), 3.45 (s, 3H), 3.25 (m, 1H), 3.07 (m, 1H), 3.03 (s, 3H), 2.81 (m, 1H) 2.63-2.57 (m, 3H), 2.57 (m, 2H), 1.62 (s, 3H).
MS (ESI, m/z): 421.2 [M+H]⁺.

Step 5-7: Synthesis of N-hydroxy-4-(6-(3-methoxyprop-1-yn-1-yl)-3',6'-dihydro-[3,4'-bipyridin]-1' (2'H)-yl)-2-methyl-2-(methylsulfonyl)butanamide The title compound was prepared the procedures described for the synthesis of Example 1, step 2-4 (Synthesis of Hydroxamate) from methyl 4-(6-(3-methoxyprop-1-yn-1-yl)-3',6'-dihydro-[3,4'-bipyridin]-1' (2'H)-yl)-2-methyl-2-(methylsulfonyl)butanoate.

$^1$H NMR (600 MHz, DMSO-d6); δ11.01 (bs, 1H), 8.72 (bs, 1H), 7.93 (dd, 1H), 7.57 (d, 1H), 6.41 (s, 2H), 4.35, (s, 2H), 4.13 (m, 1H), 4.01 (m, 1H), 3.84 (m, 1H), 3.76 (m, 1H), 3.27 (m, 1H), 3.19 (m, 1H), 3.14 (s, 3H), 2.98 (m, 1H,) 2.87 (m, 1H) 2.68 (m, 1H), 2.25 (m, 1H), 1.50 (s, 3H).

MS (ESI, m/z): 415.1 [M+H]$^+$.

Example 76: Synthesis of 3-(4-([1,1'-biphenyl]-4-yl)-3,6-dihydropyridin-1(2H)-yl)-N-hydroxy-2-methyl-2-(methylsulfonyl)propanamide

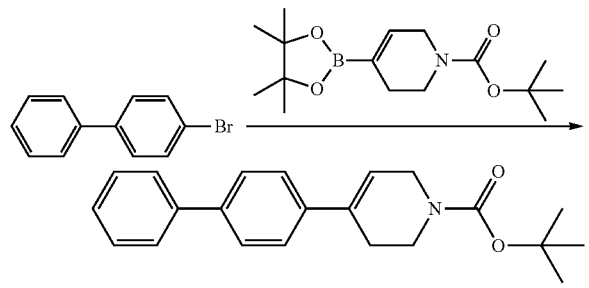

Step 1: Synthesis of tert-butyl 4-([1,1'-biphenyl]-4-yl)-3,6-dihydropyridine-1(2H)-carboxylate

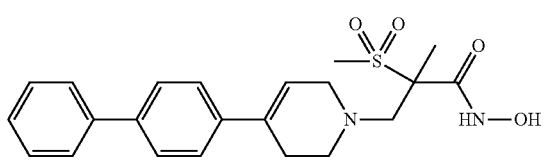 [SMILES: CC(CN1CC=C(c2ccc(-c3ccccc3)cc2)CC1)(C(=O)NO)S(C)(=O)=O]

To a solution of 4-bromo-1,1'-biphenyl (2 g, 1 eq) in a mixture of 1,4-dioxane (24 ml)/water (6 ml) was added with Pd(PPh$_3$)$_2$Cl$_2$(0.6 g, 0.1 eq), K$_2$CO$_3$(2.37 g, 2 eq) and tert-butyl 4-(4,4,5,5-tetramethyl-1,3,2-dioxaborolan-2-yl)-3,6-dihydropyridine-1(2H)-carboxylate (3.45 g, 1.3 eq). The mixture was stirred for 2 hr at 110° C., cooled down to room temperature, and extracted with ethyl acetate and water. The organic layer was washed with brine, dried over anhydrous MgSO$_4$ and concentrated in vacuo. The residue was purified with column chromatography to prepare the title compound (1.65 g, 57%).

$^1$H NMR (600 MHz, DMSO-d6); δ 7.40-7.37 (m, 4H), 7.26-7.16 (m, 4H), 7.08-7.05 (m, 1H), 6.15 (s, 1H), 4.11 (s, 2H), 3.62 (s, 2H), 2.50 (s, 2H), 1.49 (s, 9H).

MS (ESI, m/z): 336.3 [M+H]$^+$.

Step 2: Synthesis of 4-([1,1'-biphenyl]-4-yl)-1,2,3,6-tetrahydropyridine 2,2,2-trifluoroacetate

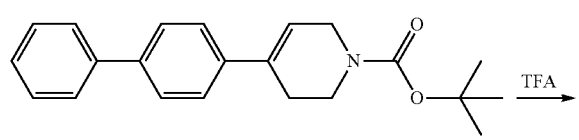

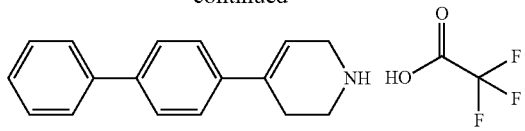

To a solution of tert-butyl 4-([1,1'-biphenyl]-4-yl)-3,6-dihydropyridine-1(2H)-carboxylate (1.1 g, 1 eq) in dichloromethane (10 ml) was added with trifluoroacetic acid (2 ml, 8 eq). The mixture was stirred for 1 hr at room temperature and concentrated in vacuo. The residue was diluted with dichloromethane and poured into excess diethyl ether. The precipitated solid was filtered off to prepare the title compound (1.08 g, 94%).

$^1$H NMR (600 MHz, DMSO-d6); δ8.68 (brs, 2H), 7.52-7.48 (m, 4H), 7.43-7.39 (m, 4H), 7.08-7.05 (m, 1H), 6.15 (s, 1H), 3.76 (s, 2H), 3.25 (s, 2H), 2.65 (s, 2H) MS (ESI, m/z): 236.1 [M+H]$^+$.

Step 3: Synthesis of methyl 3-(4-([1,1'-biphenyl]-4-yl)-3,6-dihydropyridin-1(2H)-yl)-2-methyl-2-(methylsulfonyl)propanoate

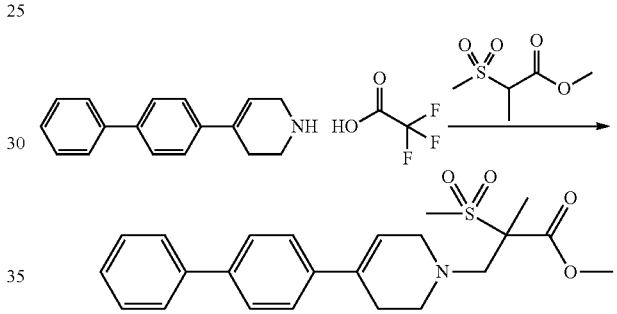

To a solution of 4-([1,1'-biphenyl]-4-yl)-1,2,3,6-tetrahydropyridine 2,2,2-trifluoroacetate (1 g, 1 eq) in a mixture of MeOH (30 ml)/THF (10 ml) was added with Et$_3$N (2 ml, 5 eq), formaldehyde (37% in water, 0.5 ml, 2.2 eq) and methyl 2-(methylsulfonyl)propanoate (0.95 g, 2 eq). The mixture was stirred for 24 hr at room temperature and concentrated in vacuo. The residue was extracted with ethyl acetate and water. The organic layer was washed with brine, dried over anhydrous MgSO$_4$ and concentrated in vacuo. The residue was purified with column chromatography to prepare the title compound (0.25 g, 21%).

$^1$H NMR (600 MHz, CDCl$_3$-d1); δ7.70-7.65 (m, 4H), 7.61-7.58 (m, 2H), 7.48-7.42 (m, 2H), 7.40-7.35 (m, 1H) 6.03 (s, 1H), 3.85 (s, 3H), 3.31 (d, 1H, J=14.4 Hz), 3.26 (s, 2H), 3.18 (s, 3H), 3.05 (d, 1H, J=13.8 Hz), 2.81 (t, 2H, J=6.0 Hz), 2.58-2.46 (m, 2H), 1.69 (s, 3H).

MS (ESI, m/z): 413.2 [M+H]$^+$.

Step 4: Synthesis of 3-(4-([1,1'-biphenyl]-4-yl)-3,6-dihydropyridin-1(2H)-yl)-2-methyl-2-(methylsulfonyl)propanoic acid

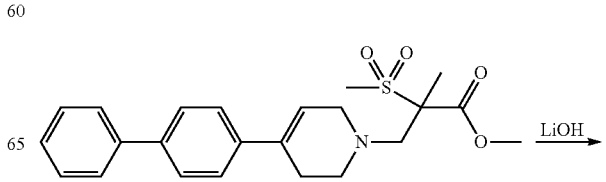

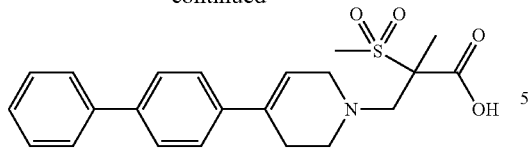

To a solution of methyl 3-(4-([1,1'-biphenyl]-4-yl)-3,6-dihydropyridin-1(2H)-yl)-2-methyl-2-(methylsulfonyl)propanoate (200 mg, 1 eq) in THF (10 ml) was added with 1N—LiOH in MeOH (5 ml, 8.3 eq). The mixture was stirred for 3 hr at room temperature. The solvent was removed under reduced pressure. The residue was acidified with 2N—HCl and extracted ethyl acetate. The organic layer was washed with brine, dried over anhydrous MgSO₄ and concentrated in vacuo to prepare the title compound (200 mg, 83%).

MS (ESI, m/z): 400.10 [M+H]⁺.

Step 5: Synthesis of 3-(4-([1,1'-biphenyl]-4-yl)-3,6-dihydropyridin-1(2H)-yl)-2-methyl-2-(methylsulfonyl)-N-((tetrahydro-2H-pyran-2-yl)oxy)propanamide

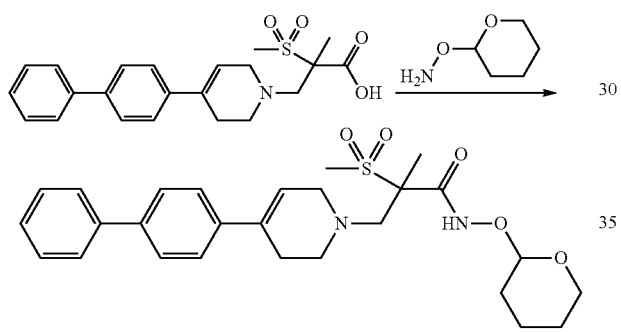

To a solution of methyl 3-(4-([1,1'-biphenyl]-4-yl)-3,6-dihydropyridin-1(2H)-yl)-2-methyl-2-(methylsulfonyl)propanoate (50 mg, 1 eq) in DMF (2 ml) was added with HATU (67 mg, 1.4 eq), HOBT (24 mg, 1.4 eq), Et₃N (0.053 ml, 3 eq) and O-(tetrahydro-2H-pyran-2-yl)hydroxylamine hydrochloride (29 mg, 2 eq). The mixture was stirred for 1 hr at room temperature and extracted with ethyl acetate and water. The organic layer was washed with brine, dried over anhydrous MgSO₄ and concentrated in vacuo. The residue was purified with column chromatography to prepare the title compound (50 mg, 80%).

MS (ESI, m/z): 499.2 [M+H]⁺.

Step 6: Synthesis of 3-(4-([1,1'-biphenyl]-4-yl)-3,6-dihydropyridin-1(2H)-yl)-N-hydroxy-2-methyl-2-(methylsulfonyl)propanamide

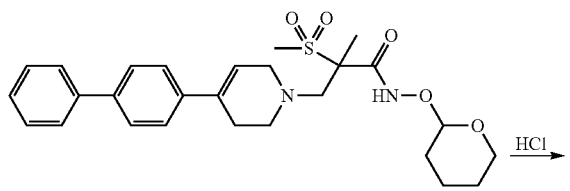

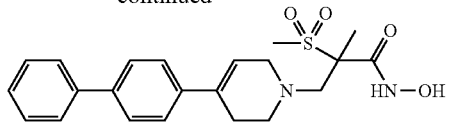

To a solution of 3-(4-([1,1'-biphenyl]-4-yl)-3,6-dihydropyridin-1(2H)-yl)-2-methyl-2-(methylsulfonyl)-N-((tetrahydro-2H-pyran-2-yl)oxy)propanamide (30 mg, 1 eq) in MeOH (1.5 ml) was added with HCl solution in MeOH (1.25N, 0.1 ml, 2 eq). The mixture was stirred for 2 hr at room temperature. The solvent was removed under reduced pressure. The residue was diluted with water (6 ml) and adjusted the pH to 7.0. The water was concentrated and the resulting residue was purified with column chromatography to prepare the title compound (10 mg, 40%).

¹H NMR (600 MHz, DMSO-d6); δ 11.3 (bs, 1H), 9.51 (bs, 1H), 7.70-7.65 (m, 4H), 7.61-7.58 (m, 2H), 7.48-7.42 (m, 2H), 7.40-7.35 (m, 1H) 6.25 (s, 1H), 4.18-3.91 (m, 2H), 3.61-3.49 (m, 4H), 3.15 (s, 3H), 2.47-2.40 (m, 2H), 1.48 (s, 3H).

MS (ESI, m/z): 415.1 [M+H]⁺.

Example 77: Synthesis of 4-(4-(4-(3-(dimethylamino)prop-1-yn-1-yl)-3-methylphenyl)-3,6-dihydropyridin-1(2H)-yl)-N-hydroxy-2-methyl-2-(methylsulfonyl)butanamide

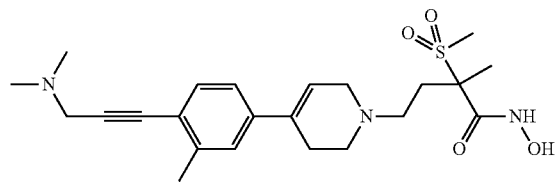 [SMILES: Cc1cc(C2=CCN(CCC(C)(C(=O)NO)S(C)(=O)=O)CC2)ccc1C#CCN(C)C]

The title compound was prepared the procedures described for the synthesis of Example 31 using 4-bromo-1-iodo-2-methylbenzene as a starting material.

¹H NMR (600 MHz, DMSO-d6); δ 11.03 (bs, 1H), 9.13 (bs, 1H), 7.34-7.33 (m, 2H), 7.24-7.23 (m, 1H), 6.20 (s, 1H), 3.50 (s, 2H), 3.12-3.10 (m, 2H), 3.07 (s, 3H), 2.66-2.63 (m, 2H), 2.48-2.44 (m, 4H), 2.39 (s, 3H), 2.25 (s, 6H), 1.84-1.82 (m, 2H), 1.43 (s, 3H).

MS (ESI, m/z): 448.2 [M+H]⁺.

Example 78: Synthesis of 4-(4-(4-(3-(dimethylamino)prop-1-yn-1-yl)-3-(trifluoromethyl)phenyl)-3,6-dihydropyridin-1(2H)-yl)-N-hydroxy-2-methyl-2-(methylsulfonyl)butanamide

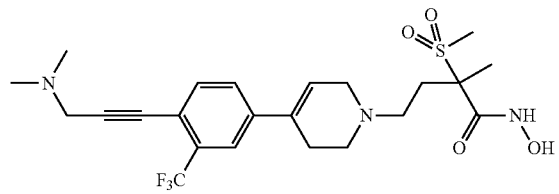 [SMILES: CN(C)CC#Cc1ccc(C2=CCN(CCC(C)(C(=O)NO)S(C)(=O)=O)CC2)cc1C(F)(F)F]

The title compound was prepared the procedures described for the synthesis of Example 31 using 4-bromo-1-iodo-2-(trifluoromethyl)benzene as a starting material.

$^1$H NMR (600 MHz, DMSO-d6); δ 11.03 (bs, 1H), 9.11 (bs, 1H), 7.71-7.69 (m, 2H), 7.63-7.62 (m, 1H), 6.36 (s, 1H), 3.50 (s, 2H), 3.32 (s, 3H), 3.17-3.16 (m, 2H), 2.66-2.57 (m, 2H), 2.46-2.32 (m, 4H), 2.23 (s, 6H), 1.83-1.80 (m, 2H), 1.45 (s, 3H).

MS (ESI, m/z): 502.2 [M+H]$^+$.

Experimental Example 1: In Vitro Test for Antibiotic Activity

To measure the antibiotic activity of the compounds prepared by Examples, antibiotic activity test in vitro was performed by agar dilution method using Mueller-Hinton agar according to the NCCLS (National Committee for Clinical Laboratory Standards. 2000. Methods for dilution antimicrobial susceptibility tests for bacteria that grow aerobiocally. Approved standard, NCCLS document M7-M5, 5$^{th}$ ed, vol 20, no 2. National Committee for Clinical Laboratory Standards, Wayne, Pa.). The test strain was *Escherichia coli* (ATCC 25922), *Klebsiella pneumonia* (ATCC 29665) and *Pseudomonas aeriginosa* (PAO1). Their minimum Inhibitory Concentration (MIC, ug/ml) are summarized in Table 1.

TABLE 1

| Example | MIC for E. coli ATCC 25922 | MIC for K. pneumoniae ATCC 29665 | MIC for P. aeruginosa PAO1 |
|---|---|---|---|
| 1 | D | D | D |
| 2 | A | B | B |
| 3 | D | B | D |
| 4 | A | A | B |
| 5 | B | C | B |
| 6 | A | B | C |
| 7 | B | B | B |
| 8 | D | D | D |
| 9 | A | B | D |
| 10 | B | C | C |
| 11 | A | B | B |
| 12 | C | C | D |
| 13 | A | B | C |
| 14 | A | B | B |
| 15 | B | C | B |
| 16 | B | B | B |
| 17 | D | C | B |
| 18 | A | B | B |
| 19 | A | B | B |
| 20 | B | C | C |
| 21 | C | D | D |
| 22 | B | D | B |
| 23 | A | B | B |
| 24 | B | B | B |
| 25 | B | B | B |
| 26 | B | C | B |
| 27 | A | B | B |
| 28 | A | A | B |
| 29 | A | B | B |
| 30 | A | B | B |
| 31 | A | B | B |
| 32 | A | B | B |
| 33 | B | C | B |
| 34 | A | B | B |
| 35 | D | D | D |
| 36 | A | B | B |
| 37 | A | D | D |
| 38 | A | B | B |
| 39 | C | C | C |
| 40 | B | B | B |
| 41 | B | C | C |
| 42 | A | B | B |
| 43 | A | B | B |
| 44 | A | B | B |
| 45 | A | B | B |
| 46 | A | B | B |
| 47 | A | B | A |
| 48 | A | B | A |
| 49 | A | B | A |
| 50 | A | B | A |
| 51 | D | D | D |
| 52 | C | D | D |
| 53 | B | B | D |
| 54 | C | D | D |
| 55 | B | B | B |
| 56 | A | A | C |
| 57 | B | D | D |
| 58 | A | B | D |
| 59 | A | C | C |
| 60 | A | C | D |
| 61 | B | D | B |
| 62 | A | B | B |
| 63 | A | A | C |
| 64 | A | B | B |
| 65 | A | C | D |
| 66 | A | B | D |
| 67 | C | D | D |
| 68 | A | B | B |
| 69 | A | A | C |
| 70 | A | A | D |
| 71 | A | A | D |
| 72 | A | A | D |
| 73 | A | B | B |
| 74 | A | A | B |
| 75 | D | D | D |
| 76 | D | D | D |

MIC key:
A = MIC's of 1.0 μg/mL or less
B = MIC's of greater than 1.0 μg/mL to 8.0 μg/mL
C = MIC's of greater than 8.0 μg/mL to 16.0 μg/mL
D = MIC's of greater than 16 μg/mL

The invention claimed is:
1. A tetrahydropyridine compound represented by the following formula I, a stereoisomer thereof or a pharmaceutically acceptable salt thereof:

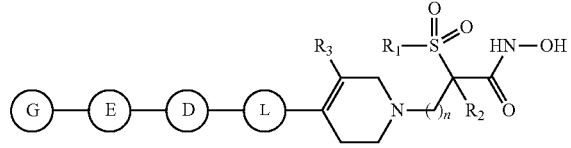

[Formula I]

wherein,
n is 1, 2 or 3;
R$_1$ is C1-C6 alkyl or C1-C6 haloalkyl;
R$_2$ is hydrogen or C1-C6 alkyl;
R$_3$ is hydrogen, C1-C6 alkyl, C1-C6 alkoxy, —OH or halogen;
L is C3-C7 cycloalkyl, aryl, heteroaryl or null, wherein at least one H of C3-C7 cycloalkyl, aryl or heteroaryl may be substituted with halogen, C1-C6 alkyl, C1-C6 haloalkyl, —NR$_A$R$_B$ or —OH;
D is C≡C, C3-C7 cycloalkyl, aryl, heteroaryl or null, wherein at least one H of C3-C7 cycloalkyl, aryl or heteroaryl may be substituted with halogen, C1-C6 alkyl, C1-C6 haloalkyl, —NR$_A$R$_B$ or —OH;
E is C≡C, C3-C7 cycloalkyl, aryl, heteroaryl or null, wherein at least one H of C3-C7 cycloalkyl, aryl or heteroaryl may be substituted with halogen, C1-C6 alkyl, C1-C6 haloalkyl, —NR$_A$R$_B$ or —OH;

G is C1-C6 alkyl, C3-C7 cycloalkyl, 4-6 membered heterocycloalkyl, aryl or heteroaryl,
wherein at least one H of C1-C6 alkyl may be substituted with halogen, —$NR_AR_B$, —OH or —$OR_C$,
at least one H of C3-C7 cycloalkyl or 4-6 membered heterocycloalkyl may be substituted with C1-C6 alkyl, C1-C6 alkyl-$NR_AR_B$, C1-C6 hydroxyalkyl, C1-C6 haloalkyl, C1-C6 alkoxy, C1-C6 alkyl-$OR_C$, —$NR_AR_B$, —OH, —(C=O)—C1-C6 alkyl or —S(=O)$_2$—C1-C6 alkyl,
at least one H of aryl or heteroaryl may be substituted with C1-C6 alkyl, C1-C6 hydroxyalkyl, C1-C6 alkyl-$NR_AR_B$, halogen, nitro, cyano, —$NR_AR_B$, —OH, —$OR_C$, —S(=O)$_2$—C1-C6 alkyl, —S(=O)$_2$—$NR_AR_B$ or —N—S(=O)$_2$—C1-C6 alkyl;
$R_A$ and $R_B$ are each independently hydrogen or C1-C6 alkyl, or $R_A$ and $R_B$ may be linked together to form 4-6 membered ring, wherein the 4-6 membered ring may have O or S atom and at least one H of the 4-6 membered ring may be substituted with halogen, —OH or C1-C6 hydroxyalkyl;
$R_C$ is C1-C6 alkyl, C1-C6 hydroxyalkyl, —(C=O)—$NR_DR_E$ or —S(=O)$_2$—C1-C6 alkyl; and
$R_D$ and $R_E$ are each independently hydrogen or C1-C6 alkyl.

2. The tetrahydropyridine compound, a stereoisomer thereof or a pharmaceutically acceptable salt thereof according to claim 1:
wherein,
n is 1 or 2;
$R_1$ is C1-C6 alkyl;
$R_2$ is C1-C6 alkyl;
$R_3$ is hydrogen;
L is aryl, heteroaryl or null, wherein at least one H of aryl or heteroaryl may be substituted with halogen, C1-C6 alkyl or C1-C6 haloalkyl;
D is C≡C or null;
E is C≡C or null;
G is C1-C6 alkyl, C3-C7 cycloalkyl, 4-6 membered heterocycloalkyl, aryl or heteroaryl,
wherein at least one H of C1-C6 alkyl may be substituted with halogen, —$NR_AR_B$, —OH or —$OR_C$,
at least one H of 4-6 membered heterocycloalkyl may be substituted with C1-C6 alkyl, —(C=O)—C1-C6 alkyl or —S(=O)$_2$—C1-C6 alkyl,
at least one H of aryl or heteroaryl may be substituted with C1-C6 alkyl, C1-C6 hydroxyalkyl, C1-C6 alkyl-$NR_AR_B$, halogen, nitro, cyano, —$NR_AR_B$, —OH, —$OR_C$, —S(=O)$_2$—C1-C6 alkyl or —S(=O)$_2$—$NR_AR_B$;
$R_A$ and $R_B$ are each independently hydrogen or C1-C6 alkyl, or $R_A$ and $R_B$ may be linked together to form 4-6 membered ring, wherein the 4-6 membered ring may have O atom and at least one H of the 4-6 membered ring may be substituted with C1-C6 hydroxyalkyl;
$R_C$ is C1-C6 alkyl, C1-C6 hydroxyalkyl, —(C=O)—$NR_DR_E$ or —S(=O)$_2$—C1-C6 alkyl; and
$R_D$ and $R_E$ are each independently hydrogen.

3. The tetrahydropyridine compound, a stereoisomer thereof or a pharmaceutically acceptable salt thereof according to claim 2:
wherein,
n is 1 or 2;
$R_1$ is C1-C6 alkyl;
$R_2$ is C1-C6 alkyl;
$R_3$ is hydrogen;
L is phenyl, pyridinyl or null, wherein at least one H of phenyl or pyridinyl may be substituted with halogen, C1-C6 alkyl or C1-C6 haloalkyl;
D is C≡C or null;
E is C≡C or null;
G is C1-C6 alkyl, C3-C6 cycloalkyl, 4-6 membered heterocycloalkyl, phenyl, pyridinyl, furanyl, thiophenyl or imidazolyl,
wherein at least one H of C1-C6 alkyl may be substituted with halogen, —$NR_AR_B$, —OH or —$OR_C$,
at least one H of 4-6 membered heterocycloalkyl may be substituted with C1-C6 alkyl, —(C=O)—C1-C6 alkyl or —S(=O)$_2$—C1-C6 alkyl,
at least one H of phenyl, pyridinyl, furanyl, thiophenyl or imidazolyl may be substituted with C1-C6 alkyl, C1-C6 hydroxyalkyl, C1-C6 alkyl-$NR_AR_B$, halogen, nitro, cyano, —$NR_AR_B$, —OH, —$OR_C$, —S(=O)$_2$—C1-C6 alkyl or —S(=O)$_2$—$NR_AR_B$;
$R_A$ and $R_B$ are each independently hydrogen or C1-C6 alkyl, or $R_A$ and $R_B$ may be linked together to form 4-6 membered ring, wherein the 4-6 membered ring may have O atom and at least one H of the 4-6 membered ring may be substituted with C1-C6 hydroxyalkyl;
$R_C$ is C1-C6 alkyl, C1-C6 hydroxyalkyl, —(C=O)—$NR_DR_E$ or —S(=O)$_2$—C1-C6 alkyl; and
$R_D$ and $R_E$ are each independently hydrogen.

4. The tetrahydropyridine compound, a stereoisomer thereof or a pharmaceutically acceptable salt thereof according to claim 3, wherein the compound is selected from the group consisting of compounds described in the following table:
1) 4-(4-(4-((4-(dimethylamino)phenyl) ethynyl)phenyl)-3,6-dihydropyridin-1(2H)-yl)-N-hydroxy-2-methyl-2-(methylsulfonyl)butanamide;
2) N-hydroxy-2-methyl-2-(methylsulfonyl)-4-(4-(4-(phenylethynyl)phenyl)-3,6-dihydropyridin-1(2H)-yl)butanamide;
3) N-hydroxy-4-(4-(4-((4-methoxyphenyl)ethynyl)phenyl)-3,6-dihydropyridin-1(2H)-yl)-2-methyl-2-(methylsulfonyl)butanamide;
4) 4-(4-(4-(cyclopropylethynyl)phenyl)-3,6-dihydropyridin-1(2H)-yl)-N-hydroxy-2-methyl-2-(methylsulfonyl)butanamide;
5) N-hydroxy-4-(4-(4-(4-hydroxybut-1-yn-1-yl)phenyl)-3,6-dihydropyridin-1(2H)-yl)-2-methyl-2-(methylsulfonyl)butanamide;
6) 4-(4-(4-(hex-1-yn-1-yl)phenyl)-3,6-dihydropyridin-1(2H)-yl)-N-hydroxy-2-methyl-2-(methylsulfonyl)butanamide;
7) 4-(4-(4-(3-(dimethylamino)prop-1-yn-1-yl)phenyl)-3,6-dihydropyridin-1(2H)-yl)-N-hydroxy-2-methyl-2-(methylsulfonyl)butanamide;
8) N-hydroxy-4-(4-(4-(3-hydroxybut-1-yn-1-yl)phenyl)-3,6-dihydropyridin-1(2H)-yl)-2-methyl-2-(methylsulfonyl)butanamide;
9) 4-(4-(4-(cyclopentylethynyl)phenyl)-3,6-dihydropyridin-1(2H)-yl)-N-hydroxy-2-methyl-2-(methylsulfonyl)butanamide;
10) 4-(4-(4-(cyclohexylethynyl)phenyl)-3,6-dihydropyridin-1(2H)-yl)-N-hydroxy-2-methyl-2-(methylsulfonyl)butanamide;
11) N-hydroxy-2-methyl-2-(methylsulfonyl)-4-(4-(4-(pent-1-yn-1-yl)phenyl)-3,6-dihydropyridin-1(2H)-yl)butanamide;
12) 4-(4-(4-(3-cyclohexylprop-1-yn-1-yl)phenyl)-3,6-dihydropyridin-1(2H)-yl)-N-hydroxy-2-methyl-2-(methylsulfonyl) butanamide;

13) N-hydroxy-2-methyl-4-(4-(4-(4-methylpent-1-yn-1-yl)phenyl)-3,6-dihydropyridin-1(2H)-yl)-2-(methylsulfonyl) butanamide;
14) 4-(4-(4-(5-chloropent-1-yn-1-yl)phenyl)-3,6-dihydropyridin-1(2H)-yl)-N-hydroxy-2-methyl-2-(methylsulfonyl) butanamide;
15) N-hydroxy-2-methyl-2-(methylsulfonyl)-4-(4-(4-(3-(pyrrolidin-1-yl)prop-1-yn-1-yl)phenyl)-3,6-dihydropyridin-1(2H)-yl)butanamide;
16) 4-(4-(4-(3-(diethylamino)prop-1-yn-1-yl)phenyl)-3,6-dihydropyridin-1(2H)-yl)-N-hydroxy-2-methyl-2-(methylsulfonyl) butanamide;
17) N-hydroxy-4-(4-(4-(3-((S)-2-(hydroxymethyl)pyrrolidin-1-yl)prop-1-yn-1-yl)phenyl)-3,6-dihydropyridin-1(2H)-yl)-2-methyl-2-(methylsulfonyl) butanamide;
18) N-hydroxy-4-(4-(4-(5-hydroxypent-1-yn-1-yl)phenyl)-3,6-dihydropyridin-1(2H)-yl)-2-methyl-2-(methylsulfonyl)butanamide;
19) 5-(4-(1-(4-(hydroxyamino)-3-methyl-3-(methylsulfonyl)-4-oxobutyl)-1,2,3,6-tetrahydropyridin-4-yl)phenyl)pent-4-yn-1-yl methanesulfonate;
20) 4-(4-(4-(5-(dimethylamino)pent-1-yn-1-yl)phenyl)-3,6-dihydropyridin-1(2H)-yl)-N-hydroxy-2-methyl-2-(methylsulfonyl)butanamide;
21) 4-(4-(4-(5-aminopent-1-yn-1-yl)phenyl)-3,6-dihydropyridin-1(2H)-yl)-N-hydroxy-2-methyl-2-(methylsulfonyl)butanamide;
22) N-hydroxy-4-(4-(4-(3-hydroxyprop-1-yn-1-yl)phenyl)-3,6-dihydropyridin-1(2H)-yl)-2-methyl-2-(methylsulfonyl)butanamide;
23) N-hydroxy-4-(4-(4-(3-methoxyprop-1-yn-1-yl)phenyl)-3,6-dihydropyridin-1(2H)-yl)-2-methyl-2-(methylsulfonyl)butanamide;
24) N-hydroxy-4-(4-(4-(3-(3-hydroxypropoxy)prop-1-yn-1-yl)phenyl)-3,6-dihydropyridin-1(2H)-yl)-2-methyl-2-(methylsulfonyl)butanamide;
25) N-hydroxy-2-methyl-2-(methylsulfonyl)-4-(4-(4-(3-morpholinoprop-1-yn-1-yl)phenyl)-3,6-dihydropyridin-1(2H)-yl)butanamide;
26) 3-(4-(1-(4-(hydroxyamino)-3-methyl-3-(methylsulfonyl)-4-oxobutyl)-1,2,3,6-tetrahydropyridin-4-yl)phenyl)prop-2-yn-1-yl carbamate;
27) 5-(4-(1-(4-(hydroxyamino)-3-methyl-3-(methylsulfonyl)-4-oxobutyl)-1,2,3,6-tetrahydropyridin-4-yl)phenyl) pent-4-yn-1-yl carbamate;
28) N-hydroxy-4-(4-(4-(5-methoxypent-1-yn-1-yl)phenyl)-3,6-dihydropyridin-1(2H)-yl)-2-methyl-2-(methylsulfonyl)butanamide;
29) N-hydroxy-4-(4-(4-(6-hydroxyhex-1-yn-1-yl)phenyl)-3,6-dihydropyridin-1(2H)-yl)-2-methyl-2-(methylsulfonyl)butanamide;
30) N-hydroxy-2-methyl-2-(methylsulfonyl)-4-(4-(4-(6-morpholinohex-1-yn-1-yl)phenyl)-3,6-dihydropyridin-1(2H)-yl)butanamide;
31) 4-(4-(4-(3-(dimethylamino)prop-1-yn-1-yl)-3-fluorophenyl)-3,6-dihydropyridin-1(2H)-yl)-N-hydroxy-2-methyl-2-(methylsulfonyl) butanamide;
32) 4-(4-(4-(3-(dimethylamino)prop-1-yn-1-yl)-3,5-difluorophenyl)-3,6-dihydropyridin-1(2H)-yl)-N-hydroxy-2-methyl-2-(methylsulfonyl)butanamide;
33) 4-(4-(4-(3-(dimethylamino)prop-1-yn-1-yl)-2-fluorophenyl)-3,6-dihydropyridin-1(2H)-yl)-N-hydroxy-2-methyl-2-(methylsulfonyl)butanamide;
34) N-hydroxy-2-methyl-2-(methylsulfonyl)-4-(4-(4-(thiophen-2-ylethynyl)phenyl)-3,6-dihydropyridin-1(2H)-yl)butanamide;
35) N-hydroxy-2-methyl-2-(methylsulfonyl)-4-(4-(4-((4-nitrophenyl)ethynyl)phenyl)-3,6-dihydropyridin-1(2H)-yl)butanamide;
36) N-hydroxy-2-methyl-2-(methylsulfonyl)-4-(4-(4-(pyridin-3-ylethynyl)phenyl)-3,6-dihydropyridin-1(2H)-yl)butanamide;
37) N-hydroxy-4-(4-(4-((4-hydroxyphenyl)ethynyl)phenyl)-3,6-dihydropyridin-1(2H)-yl)-2-methyl-2-(methylsulfonyl)butanamide;
38) N-hydroxy-2-methyl-4-(4-(4-((1-methyl-1H-imidazol-4-yl)ethynyl)phenyl)-3,6-dihydropyridin-1(2H)-yl)-2-(methylsulfonyl)butanamide;
39) N-hydroxy-2-methyl-4-(4-(4-((1-methylazetidin-3-yl) ethynyl)phenyl)-3,6-dihydropyridin-1(2H)-yl)-2-(methylsulfonyl)butanamide;
40) 4-(4-(4-((1-acetylazetidin-3-yl)ethynyl)phenyl)-3,6-dihydropyridin-1(2H)-yl)-N-hydroxy-2-methyl-2-(methylsulfonyl)butanamide;
41) N-hydroxy-2-methyl-2-(methylsulfonyl)-4-(4-(4-((1-(methylsulfonyl)azetidin-3-yl)ethynyl)phenyl)-3,6-dihydropyridin-1(2H)-yl)butanamide;
42) 4-(4-(3-fluoro-4-(7-hydroxyhepta-1,3-diyn-1-yl)phenyl)-3,6-dihydropyridin-1(2H)-yl)-N-hydroxy-2-methyl-2-(methylsulfonyl)butanamide;
43) 4-(4-(3-fluoro-4-(6-hydroxyhexa-1,3-diyn-1-yl)phenyl)-3,6-dihydropyridin-1(2H)-yl)-N-hydroxy-2-methyl-2-(methylsulfonyl)butanamide;
44) 4-(4-(4-(cyclopropylbuta-1,3-diyn-1-yl)-3-fluorophenyl)-3,6-dihydropyridin-1(2H)-yl)-N-hydroxy-2-methyl-2-(methylsulfonyl)butanamide;
45) 4-(4-(4-(5-(dimethylamino)penta-1,3-diyn-1-yl)-3-fluorophenyl)-3,6-dihydropyridin-1(2H)-yl)-N-hydroxy-2-methyl-2-(methylsulfonyl) butanamide;
46) N-hydroxy-4-(4-(4-(7-hydroxyhepta-1,3-diyn-1-yl) phenyl)-3,6-dihydropyridin-1(2H)-yl)-2-methyl-2-(methylsulfonyl)butanamide;
47) N-hydroxy-4-(4-(4-(6-hydroxyhexa-1,3-diyn-1-yl) phenyl)-3,6-dihydropyridin-1(2H)-yl)-2-methyl-2-(methylsulfonyl)butanamide;
48) N-hydroxy-4-(4-(4-(5-hydroxypenta-1,3-diyn-1-yl) phenyl)-3,6-dihydropyridin-1(2H)-yl)-2-methyl-2-(methylsulfonyl)butanamide;
49) 4-(4-(4-(5-(dimethylamino)penta-1,3-diyn-1-yl)phenyl)-3,6-dihydropyridin-1(2H)-yl)-N-hydroxy-2-methyl-2-(methylsulfonyl)butanamide;
50) N-hydroxy-4-(4-(4-(5-methoxypenta-1,3-diyn-1-yl) phenyl)-3,6-dihydropyridin-1(2H)-yl)-2-methyl-2-(methylsulfonyl)butanamide;
51) N-hydroxy-2-methyl-2-(methylsulfonyl)-4-(4-(4-(phenylbuta-1,3-diyn-1-yl)phenyl)-3,6-dihydropyridin-1(2H)-yl)butanamide;
52) N-hydroxy-2-methyl-2-(methylsulfonyl)-4-(4-(pyridin-4-ylethynyl)-3,6-dihydropyridin-1(2H)-yl)butanamide;
53) 4-(4-((4-bromophenyl)ethynyl)-3,6-dihydropyridin-1(2H)-yl)-N-hydroxy-2-methyl-2-(methylsulfonyl)butanamide;
54) N-hydroxy-4-(4-(7-hydroxyhepta-1,3-diyn-1-yl)-3,6-dihydropyridin-1(2H)-yl)-2-methyl-2-(methylsulfonyl) butanamide;
55) N-hydroxy-2-methyl-2-(methylsulfonyl)-4-(4-(4-(pyridin-4-yl)phenyl)-3,6-dihydropyridin-1(2H)-yl)butanamide;
56) 4-(4-([1,1'-biphenyl]-4-yl)-3,6-dihydropyridin-1(2H)-yl)-N-hydroxy-2-methyl-2-(methylsulfonyl)butanamide;

57) 4-(4-(4'-chloro-[1,1'-biphenyl]-4-yl)-3,6-dihydropyridin-1(2H)-yl)-N-hydroxy-2-methyl-2-(methylsulfonyl)butanamide;

58) 4-(4-(4'-fluoro-[1,1'-biphenyl]-4-yl)-3,6-dihydropyridin-1(2H)-yl)-N-hydroxy-2-methyl-2-(methylsulfonyl)butanamide;

59) N-hydroxy-4-(4-(4'-hydroxy-[1,1'-biphenyl]-4-yl)-3,6-dihydropyridin-1(2H)-yl)-2-methyl-2-(methylsulfonyl)butanamide;

60) 4-(4-(3'-fluoro-4'-methoxy-[1,1'-biphenyl]-4-yl)-3,6-dihydropyridin-1(2H)-yl)-N-hydroxy-2-methyl-2-(methylsulfonyl)butanamide;

61) N-hydroxy-2-methyl-2-(methylsulfonyl)-4-(4-(4-(pyridin-3-yl)phenyl)-3,6-dihydropyridin-1(2H)-yl)butanamide;

62) 4-(4-(4-(6-fluoropyridin-3-yl)phenyl)-3,6-dihydropyridin-1(2H)-yl)-N-hydroxy-2-methyl-2-(methylsulfonyl)butanamide;

63) 4-(4-(4-(furan-3-yl)phenyl)-3,6-dihydropyridin-1(2H)-yl)-N-hydroxy-2-methyl-2-(methylsulfonyl)butanamide;

64) N-hydroxy-2-methyl-2-(methylsulfonyl)-4-(4-(4'-(methylsulfonyl)-[1,1'-biphenyl]-4-yl)-3,6-dihydropyridin-1(2H)-yl)butanamide;

65) N-hydroxy-4-(4-(4'-(hydroxymethyl)-[1,1'-biphenyl]-4-yl)-3,6-dihydropyridin-1(2H)-yl)-2-methyl-2-(methylsulfonyl)butanamide;

66) 4-(4-(4'-cyano-[1,1'-biphenyl]-4-yl)-3,6-dihydropyridin-1(2H)-yl)-N-hydroxy-2-methyl-2-(methylsulfonyl)butanamide;

67) N-hydroxy-2-methyl-2-(methylsulfonyl)-4-(4-(4'-pentyl-[1,1'-biphenyl]-4-yl)-3,6-dihydropyridin-1(2H)-yl)butanamide;

68) 4-(4-(4'-(azetidin-1-ylsulfonyl)-[1,1'-biphenyl]-4-yl)-3,6-dihydropyridin-1(2H)-yl)-N-hydroxy-2-methyl-2-(methylsulfonyl)butanamide;

69) 4'-(1-(4-(hydroxyamino)-3-methyl-3-(methylsulfonyl)-4-oxobutyl)-1,2,3,6-tetrahydropyridin-4-yl)-[1,1'-biphenyl]-4-yl methanesulfonate;

70) N-hydroxy-2-methyl-2-(methylsulfonyl)-4-(4-(4-(thiophen-3-yl)phenyl)-3,6-dihydropyridin-1(2H)-yl)butanamide;

71) N-hydroxy-4-(4-(4-(3-methoxythiophen-2-yl)phenyl)-3,6-dihydropyridin-1(2H)-yl)-2-methyl-2-(methylsulfonyl)butanamide;

72) N-hydroxy-2-methyl-2-(methylsulfonyl)-4-(4-(4-(4-methylthiophen-2-yl)phenyl)-3,6-dihydropyridin-1(2H)-yl)butanamide;

73) 4-(4-(4'-(ethylsulfonyl)-[1,1'-biphenyl]-4-yl)-3,6-dihydropyridin-1(2H)-yl)-N-hydroxy-2-methyl-2-(methylsulfonyl)butanamide;

74) N-hydroxy-2-methyl-2-(methylsulfonyl)-4-(4-(4'-(morpholinomethyl)-[1,1'-biphenyl]-4-yl)-3,6-dihydropyridin-1(2H)-yl)butanamide;

75) N-hydroxy-4-(6-(3-methoxyprop-1-yn-1-yl)-3',6'-dihydro-[3,4'-bipyridin]-1' (2'H)-yl)-2-methyl-2-(methylsulfonyl)butanamide;

76) 3-(4-([1,1'-biphenyl]-4-yl)-3,6-dihydropyridin-1(2H)-yl)-N-hydroxy-2-methyl-2-(methylsulfonyl)propanamide;

77) 4-(4-(4-(3-(dimethylamino)prop-1-yn-1-yl)-3-methylphenyl)-3,6-dihydropyridin-1(2H)-yl)-N-hydroxy-2-methyl-2-(methylsulfonyl)butanamide; and 78) 4-(4-(4-(3-(dimethylamino)prop-1-yn-1-yl)-3-(trifluoromethyl)phenyl)-3,6-dihydropyridin-1(2H)-yl)-N-hydroxy-2-methyl-2-(methylsulfonyl)butanamide.

5. A method for inhibiting UDP-3-O—(R-3-hydroxymyristoyl)-N-acetylglucosamine deacetylase (LpxC), comprising administering to a patient in need thereof a therapeutically effective amount of the compound represented by formula I, stereoisomer thereof or pharmaceutically acceptable salt thereof according to claim 1.

6. A method for treating bacterial infections, comprising administering to a patient in need thereof a therapeutically effective amount of the compound represented by formula I, stereoisomer thereof or pharmaceutically acceptable salt thereof according to claim 1.

7. The method of claim 6, wherein the bacterial infections are caused by Gram-negative bacteria.

8. The method of claim 7, wherein the bacterial infections are selected from the group consisting of nosocomial pneumonia, urinary tract infections, systemic infections, skin and soft tissue infections, surgical infections, intraabdominal infections, lung infections, endocarditis, diabetic foot infection, osteomyelitis, and central nervous system infections.

\* \* \* \* \*

UNITED STATES PATENT AND TRADEMARK OFFICE
CERTIFICATE OF CORRECTION

PATENT NO. : 10,160,724 B2
APPLICATION NO. : 15/718474
DATED : December 25, 2018
INVENTOR(S) : Sun-Ho Choi et al.

It is certified that error appears in the above-identified patent and that said Letters Patent is hereby corrected as shown below:

In the Specification

Column 11, Line 57:
Delete "*pneumonia*" and insert -- *pneumoniae* -- therefor.

Column 12, Line 32:
Delete "*pneumonia*" and insert -- *pneumoniae* -- therefor.

Column 97, Line 20:
Delete "*pneumonia*" and insert -- *pneumoniae* -- therefor.

Column 97, Line 21:
Delete "*aeriginosa*" and insert -- *aeruginosa* -- therefor.

Column 97, Line 21:
Delete "minimum" and insert -- Minimum -- therefor.

In the Claims

Column 99, Line 9:
In Claim 1, delete "—S(=)$_2$—" and insert -- —S(=O)$_2$— -- therefor.

Column 100, Line 32:
In Claim 4, delete "phenyl) ethynyl)" and insert -- phenyl)ethynyl) -- therefor.

Column 100, Lines 66-67:
In Claim 4, delete "(methylsulfonyl) butanamide;" and insert -- (methylsulfonyl)butanamide; -- therefor.

Signed and Sealed this
Twelfth Day of March, 2019

Andrei Iancu
*Director of the United States Patent and Trademark Office*

CERTIFICATE OF CORRECTION (continued)
U.S. Pat. No. 10,160,724 B2

Column 101, Lines 2-3:
In Claim 4, delete "(methylsulfonyl) butanamide;" and insert -- (methylsulfonyl)butanamide; -- therefor.

Column 101, Lines 5-6:
In Claim 4, delete "(methylsulfonyl) butanamide;" and insert -- (methylsulfonyl)butanamide; -- therefor.

Column 101, Line 12:
In Claim 4, delete "(methylsulfonyl) butanamide;" and insert -- (methylsulfonyl)butanamide; -- therefor.

Column 101, Line 15:
In Claim 4, delete "(methylsulfonyl) butanamide;" and insert -- (methylsulfonyl)butanamide; -- therefor.

Column 101, Lines 45-46:
In Claim 4, delete "phenyl) pent" and insert -- phenyl)pent -- therefor.

Column 101, Line 58:
In Claim 4, delete "(methylsulfonyl) butanamide;" and insert -- (methylsulfonyl)butanamide; -- therefor.

Column 102, Line 34:
In Claim 4, delete "(methylsulfonyl) butanamide;" and insert -- (methylsulfonyl)butanamide; -- therefor.

Column 104, Line 13:
In Claim 4, delete "1' (2'H)" and insert -- 1'(2'H) -- therefor.